United States Patent
Ikeuchi

(10) Patent No.: US 7,431,707 B2
(45) Date of Patent: Oct. 7, 2008

(54) SUPPORT MOMENT CONTROL METHOD FOR LEG MOTION SUPPORT ORTHOSIS

(75) Inventor: Yasushi Ikeuchi, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 480 days.

(21) Appl. No.: 11/304,051

(22) Filed: Dec. 15, 2005

(65) Prior Publication Data

US 2006/0130594 A1 Jun. 22, 2006

(30) Foreign Application Priority Data

Dec. 17, 2004 (JP) ............................. 2004-366911

(51) Int. Cl.
*A61F 5/00* (2006.01)
(52) U.S. Cl. .......................... 602/16; 602/19
(58) Field of Classification Search ...... 602/5, 602/16, 19, 23, 24, 26, 27; 482/51, 66; 601/33–35
See application file for complete search history.

(56) References Cited

U.S. PATENT DOCUMENTS

| 5,658,242 | A * | 8/1997 | McKay et al. | 602/16 |
| 5,961,476 | A * | 10/1999 | Betto et al. | 602/16 |
| 7,278,979 | B2 * | 10/2007 | Shimada et al. | 602/16 |
| 2005/0177080 | A1 * | 8/2005 | Yasuhara et al. | 602/16 |

FOREIGN PATENT DOCUMENTS

| JP | 2003-089083 | 3/2003 |
| JP | 2003-220102 | 8/2003 |
| JP | 2004-314247 | 11/2004 |

* cited by examiner

*Primary Examiner*—Michael A. Brown
(74) *Attorney, Agent, or Firm*—Rankin, Hill & Clark LLP

(57) ABSTRACT

Target joint support moments of each leg are determined by estimating joint moments of the each leg necessary for the person A wearing a leg motion support orthosis (1) to make a motion independently and according to the estimated joint moments. Moreover, floor reaction forces for the support orthosis (1) to make a motion independently are estimated, and then estimated values of actual joint support moments actually applied from the support orthosis (1) to the joints of the each leg of the person (A) are found by using the estimated floor reaction forces and outputs of the force sensor (22) provided in a leg link portion (4) of the support orthosis (1). Torque generation units (15) and (16) of the support orthosis (1) are controlled in such a way that the estimated values of the actual joint support moments are coincident with the target joint support moments. Thereby, the leg motion of the person can be supported. Moreover, it effectively prevents forces other than the necessary forces to support the leg motion of the person from acting on the person and enables the person to make a leg motion with feeling as if the person were not wearing the leg motion support orthosis as fully as possible.

5 Claims, 27 Drawing Sheets

SUPPORT MOMENT CONTROL METHOD FOR LEG MOTION SUPPORT ORTHOSIS

BACKGROUND OF THE INVENTION

1. Field of the Invention

The present invention relates to a support moment control method for a leg motion support orthosis put on a person to support the motion (walking or the like) of his or her legs.

2. Related Background Art

Conventionally, there is an already known leg motion support orthosis disclosed in Japanese Patent Laid-Open No. 2003-220102 (hereinafter, referred to as "patent document 1") as this type of leg motion support orthosis. In the support orthosis in the patent document 1, a waist support belt to be put on a person's waist is coupled to each foot support portion where the person's foot portion is placed, via a waist moment generator corresponding to a hip joint, a thigh support beam corresponding to a thigh, a knee moment generator corresponding to a knee joint, a shank support beam corresponding to a crus portion, and a heel moment generating section corresponding to an ankle joint in this order from the waist side of the support orthosis. Moreover, in the support orthosis of the patent document 1, the foot support portion, the shank support beam, and the thigh support beam are connected to the foot portion, the crus portion, and the thigh portion of the person's leg by using belts, respectively. Then, external forces acting on the person's leg are calculated from detected values of a load sensor provided on the bottom face of the foot support portion and force sensors provided in the belts, and moments generated at the joints of the person's leg are calculated based on the calculated external forces. Moreover, target moments are determined by multiplying a predetermined reduction ratio by the calculated moments to control the moment generators in such a way that forces satisfying the target moments are applied from the support orthosis to the person's leg.

Incidentally, the leg motion support orthosis put on a person is desirably capable of supporting the person's leg motion in such a way that the person is not aware of an inertia force generated by the weight of the support orthosis or a motion thereof. For example, supposing that the target support moments to be applied from the support orthosis to the joints of each leg are each zero, it is desirable that the person can make his or her leg motion in the same manner as when the person is not wearing the support orthosis. In other words, supposing that the target support moments are each zero, the support orthosis is desirably capable of making a motion in such a way as to follow the person's leg motion autonomously (independently) without the need for the person to consciously generate forces to move the respective portions of the support orthosis. On that basis, it is desirable that the support orthosis is capable of making a part of the moments of the leg joints kinetically required to make a desired leg motion that the person is supposing when the person is not wearing the support orthosis.

In the support orthosis of the patent document 1, however, no consideration is given to the external forces applied to the support orthosis 1 necessary for the support orthosis to autonomously follow the person's leg motion and joint moments of the support orthosis. Therefore, when using the support orthosis of the patent document 1, the person receives inertia forces (inertia forces other than support forces) generated by the weight of the support orthosis or the motion of the support orthosis in various situations while the person is moving. Thus, the person wearing the support orthosis often encounters a situation where he or she have to make a leg motion with being aware of the weight of the support orthosis or the like. Consequently, the support orthosis is susceptible to a difference between the actual leg motion pattern and the motion pattern supposed by the person. Furthermore, it leads to causing a jerky leg motion or to making it hard to make a smooth leg motion disadvantageously.

Moreover, since the support orthosis of the patent document 1 has a lot of force sensors provided on the bottom face of the each foot support portion and on the bands fixed to the person's leg, it is disadvantageous in cost and has a problem that it is susceptible to noise included in outputs of the force sensors synergistically. Particularly, the output of the load sensor on the bottom face of the foot support portion is directly susceptible to the influence of the floor shape or the like and the load sensor is easily damaged by an impact on the foot support portion, by which it is hard to secure high reliability. As a result, the moments generated by the moment generators of the support orthosis are easily disordered, which could lead to an abrupt change in the support forces applied to the person's legs.

SUMMARY OF THE INVENTION

In view of the above background, the present invention has been provided. Therefore, it is an object of the present invention to provide a support moment control method for a leg motion support orthosis capable of effectively reducing forces applied to a person other than forces necessary to support the person's leg motion, such as the weight of the leg motion support orthosis put on the person and thereby enabling the person to feel like as if he or she were not wearing the leg motion support orthosis while making the leg motion. Furthermore, it is another object of the present invention to provide a support moment control method for a leg motion support orthosis capable of controlling a torque generation unit of the support orthosis to generate appropriate torques without providing a force sensor on the bottom face of a foot attachment portion of the leg motion support orthosis.

To achieve these objects, according to a first feature of the present invention, there is provided a support moment control method for a leg motion support orthosis, which controls torques generated by a torque generation unit for the leg motion support orthosis having at least a waist attachment portion fixed to the waist of a person, a pair of foot attachment portions fixed to the feet of the person and provided in such a way as to be put in contact with the ground with bearing the weight of the person during a landing period of the feet, and a pair of leg link portions extending substantially along the legs of the person between the waist attachment portion and the foot attachment portions by coupling the waist attachment portion and each of the foot attachment portions, wherein each of the leg link portions has a plurality of joint regions including at least three joint regions corresponding to the person's hip joint, knee joint, and ankle joint, respectively, and the torque generation unit capable of generating torques at the joint regions corresponding to at least the hip joint and the knee joint of the plurality of joint regions, the method comprising: during the motion of both legs of the person wearing the leg motion support orthosis, a first step of sequentially estimating human-side joint moments, which are moments to be generated at the knee joint and the hip joint of the each leg, respectively, supposing that the person is making the motion of the both legs with the leg motion support orthosis removed from the person; a second step of sequentially estimating floor reaction forces acting on the foot attachment portions of the leg motion support orthosis, supporting that the leg motion support orthosis is independently making a motion of the leg motion support orthosis following the motion of the person's legs; a third step of sequentially measuring reaction forces each of a resultant force between a force applied from the person via the foot attachment portion coupled to the leg link portion of each leg link portion of the leg motion support orthosis and the floor reaction force applied to the foot attachment portion, supposing that the leg motion support orthosis is independently making the motion of the leg motion support orthosis following the motion of the person's legs, on the basis of an output of a force sensor provided in the leg link portion in the area closer to the foot attachment portion than to the knee joint region of the each leg link portion so that the resultant force can be detected; a fourth step of measuring at least the amount of rotation of the knee joint of the joints of the person's each leg; a fifth step of sequentially calculating estimated values of actual joint support moments, which are support moments actually generated at the knee joint and the hip joint of the person's each leg due to the torques generated by the torque generation unit by using at least the amount of rotation of the knee joint measured in the fourth step, the reaction forces of the resultant forces measured in the third step, and the floor reaction forces estimated in the second step; a sixth step of sequentially determining target joint support moments, each of which is a target support moment to be generated at each of the knee joint and the hip joint of the person's each leg by means of the torque generated by the torque generation unit according to at least the human-side joint moments of the knee joint and the hip joint of the each leg estimated in the first step; and a seventh step of controlling the torques generated by the torque generation unit in such a way that the estimated values of the actual joint support moments of the knee joint and the hip joint of the person's each leg calculated in the fifth step are substantially coincident with the respective target joint support moments of the knee joint and the hip joint determined in the sixth step.

According to the first feature of the present invention, the floor reaction forces estimated in the second step are the floor reaction forces applied to the foot attachment portions of the leg motion support orthosis, supporting that the leg motion support orthosis is independently making a motion of the leg motion support orthosis following the motion of the person's legs, in other words, floor reaction forces kinetically required for the leg motion support orthosis to independently make a motion of the leg motion support orthosis following the motion of the person's legs. Moreover, the reaction forces each of the resultant force measured in the third step are the reaction forces each of the resultant force between the force applied from the person via the foot attachment portion coupled to the leg link portion of the each leg link portion of the leg motion support orthosis and the floor reaction force applied to the foot attachment portion, supposing that the leg motion support orthosis is independently making the motion of the leg motion support orthosis following the motion of the person's legs.

Therefore, the value obtained by subtracting the force opposite in sign (direction) to the floor reaction force estimated in the second step from the measured reaction force of the resultant force indicates the force applied to the person's foot portion via the foot attachment portion from the support orthosis.

The resultant force can be detected by the force sensor provided in the leg link portion in the area closer to the foot attachment portion than to the knee joint region of the each leg link portion. In this instance, the leg link portion is not directly put into contact with the ground during the landing period, and therefore the outputs of the force sensor are very stable and reliable. More specifically, the floor reaction force necessary for the person to make a motion act on the person via the each foot attachment portion put on the foot portion of the person's leg during the landing period of the person's leg and the floor reaction force is not basically transmitted to the leg link portion.

Therefore, in the fifth step, it is possible to obtain appropriately the estimated values of the actual joint support moments actually generated at the person's knee joint and hip joint due to the torques of the torque generation unit of the support orthosis by using at least the amount of rotation of the knee joint measured in the fourth step, the reaction forces of the resultant forces measured in the third step, and the floor reaction forces estimated in the second step. For example, if the support orthosis is fixed only to the person's waist and foot portion, the value of the force (translational force) opposite in sign (direction) to the floor reaction force estimated in the second step may be transformed to the actual joint support moment of the person's knee joint and the actual joint support moment of the person's hip joint by performing a geometric operation from the measured reaction force of the resultant force. In that case, a measured value of the amount of rotation at the person's knee joint is necessary to obtain the estimated value of the actual joint support moment of the hip joint.

In the first feature of the present invention, the torques generated by the torque generation units are controlled so that the estimated values of the actual joint support moments at the person's knee joint and hip joint obtained in this manner are substantially coincident with the target joint support moments of the knee joint and the hip joint determined in the sixth step. In this instance, the estimated values of the actual joint support moments are obtained as described above. Moreover, the target joint support moments are determined according to the human-side joint moments, which should be generated at the knee joint and the hip joint of the each leg, supposing that the motion of the person's legs are being made with the leg motion support orthosis removed from the person. For example, they are determined to be a part of the human-side joint moments (a predetermined proportion of the human-side joint moments at the knee joint and the hip joint).

Therefore, the torques generated by the torque generation unit are torques enabling the leg motion support orthosis to generate the target joint support moments at the person's knee joint and hip joint while maintaining torques enabling the support orthosis to make the motion of the support orthosis following the person's leg motion by itself (independently). For example, supposing that the target joint support moments are each zero, the torques generated by the torque generation unit are torques zeroing the actual joint support moments generated at the person's knee joint and hip joint and these torques enable the support orthosis to make the motion of the support orthosis following the person's leg motion by itself (independently).

Therefore, according to the first feature of the present invention, it is possible to effectively reduce forces applied to the person other than forces necessary to support the person's leg motion, such as the weight of the leg motion support orthosis put on the person, thereby enabling the person to make the leg motion with feeling as if he or she were not wearing the leg motion support orthosis.

In the first feature of the present invention, preferably the each foot attachment portion is provided, for example, in such a way as to abut against the bottom face of the person's each foot portion. Moreover, the each leg link portion is preferably extending substantially along the lateral surface of the each leg in a stand-up position relative to the foot attachment portion. Moreover, in the first feature of the present invention, the torque generation unit may be caused to generate a torque at the ankle joint region or a joint region other than the ankle joint region provided in the area closer to the foot attachment portion than to the knee joint region of the each leg link portion. In this instance, it is recommended that the force sensor is provided in the area further closer to the foot attachment portion (the area of the leg link portion) than to the joint region closest to the foot attachment portion of the joint regions where the torque generation unit generates the torque.

In the first feature of the present invention, preferably the first step includes the steps of: estimating a floor reaction force applied to the each leg, supposing that the motion of the person's legs is being made with the leg motion support orthosis removed from the person, by using at least an output of an acceleration sensor provided in the leg motion support orthosis, an output of a joint displacement sensor provided in the each joint region in such a way as to be capable of detecting the amount of rotation of the each joint region of the each leg link portion of the leg motion support orthosis, and a rigid link model in which the person is represented by a link body made of a plurality of rigid elements and a plurality of joint elements; and estimating the human-side joint moments in arithmetic processing of an inverse dynamics model by using the estimated floor reaction force (a second feature of the present invention).

According to the second feature of the present invention, it is possible to estimate the floor reaction force applied to the each leg, supposing that the motion of the person's legs is being made with the leg motion support orthosis removed from the person, without attachment of the force sensor on the bottom face of the foot attachment portion. Therefore, it becomes possible to estimate the floor reaction force applied to the each leg with eliminating the effect of a floor shape or the like. As a result, stability can be enhanced in change of the estimated value of the floor reaction force and thus the estimated values of the human-side joint moments.

Moreover, in the first feature of the present invention, preferably the second step includes estimating a floor reaction force applied to the each foot attachment portion of the leg motion support orthosis, supposing that the leg motion support orthosis is independently making the motion of the leg motion support orthosis following the motion of the person's legs, by using at least an output of an acceleration sensor provided in the leg motion support orthosis, an output of a joint displacement sensor provided in the joint region in such a way as to be capable of detecting the amount of rotation of the each joint region of the each leg link portion of the leg motion support orthosis, and a rigid link model in which the leg motion support orthosis is represented by a link body made of a plurality of rigid elements and a plurality of joint elements (a third feature of the present invention).

According to the third feature of the present invention, it is possible to estimate the floor reaction force applied to the each foot attachment portion of the leg motion support orthosis, supposing that the leg motion support orthosis is independently making the motion of the leg motion support orthosis following the motion of the person's legs, without attachment of the force sensor on the bottom face of the foot attachment portion in the same manner as for the second feature of the present invention. Therefore, it becomes possible to estimate the floor reaction force applied to the each foot attachment portion with eliminating the effect of a floor shape or the like. As a result, stability can be enhanced in change of the estimated value of the floor reaction force. Thus, the torque generation unit of the support orthosis put on the person can be controlled to generate appropriate torques.

The third feature of the present invention may be combined with the second feature of the present invention. In this instance, the acceleration sensor and the joint displacement sensor can be the same as those of the second feature of the present invention.

Moreover, in the first to third features of the present invention, if the each leg link portion of the leg motion support orthosis is coupled to the person's leg corresponding to the leg link portion in at least one or more places (for example, places corresponding to the thigh and a crus), preferably the method includes an eighth step of measuring the reaction forces of the forces applied from the person to the leg motion support orthosis in the coupled places on the basis of the output of the force sensor provided in the leg motion support orthosis in such a way as to be capable of detecting the force, and the fifth step includes calculating estimated values of the actual joint support moments by using at least the reaction forces of the force measured in the eighth step, the amount of rotation of the knee joint measured in the fourth step, the reaction forces of the resultant forces measured in the third step, and the floor reaction forces estimated in the second step (a fourth feature of the present invention).

According to the fourth feature of the present invention, measurements are obtained regarding the reaction forces of the forces applied from the person to the leg motion support orthosis in the coupled places for coupling the leg link portion and the person's legs, and therefore the estimated values of the actual joint support moments can be accurately obtained by using the measured reaction forces in the fifth step further. In the coupled places, there is no need for the leg link portion of the leg motion support orthosis to be completely fixed to the person's leg. For example, the region (the thigh, the crus, etc.) of the person's leg in the coupled place may be relatively movable to the region of the leg link portion in the coupled place substantially in the central axis direction of the region of the leg and be coupled in such a way as to be immovable in the direction substantially perpendicular to the central axis direction.

Moreover, in the first to fourth features of the present invention, the method preferably includes a ninth step of sequentially estimating orthosis-side joint moments, which are moments to be generated in the knee joint region and the hip joint region of the each leg link portion of the leg motion support orthosis, supposing that the leg motion support orthosis is independently making the motion of the leg motion support orthosis following the motion of the person's legs, by performing arithmetic processing of the inverse dynamics model using the floor reaction forces estimated in the second step, and the seventh step includes the steps of: determining a feedback control input of the torques generated by the torque generation unit according to a feedback control law in such a way as to approximate the difference between the estimated value of each of the actual joint support moments of the knee joint and the hip joint of the person's each leg calculated in the fifth step and each of the target joint support moments of the knee joint and the hip joint determined in the sixth step to zero; and determining a feedforward control input of the torques generated by the torque generation unit at least according to each of the orthosis-side joint moments of the knee joint region and the hip joint region of the each leg link portion of the leg motion support orthosis estimated in the ninth step, to control the torque generated by the torque generation unit according to the determined feedback control input and the feedforward control input (a fifth feature of the present invention).

According to the fifth feature of the present invention, the orthosis-side joint moments estimated in the ninth step by using the floor reaction forces estimated in the second step are moments to be generated in the knee joint region and the hip joint region of the each leg link portion of the leg motion support orthosis, supposing that the leg motion support orthosis is independently making the motion of the leg motion support orthosis following the motion of the person's legs. In the fifth feature of the present invention, there is determined the feedback control input to approximate the difference between the estimated value of each of the actual joint support moments of the knee joint and the hip joint of the person's each leg and each of the target joint support moments of the knee joint and the hip joint to zero, in other words, the control input of a torque of the torque generation unit (for example, an indicator current of an electric motor) to cause the difference to converge to zero. Moreover, the feedforward control input is determined at least according to each of the estimated orthosis-side joint moments of the knee joint region and the hip joint region. Therefore, the feedforward control input includes a control input component to cause the torque generation unit to generate torques enabling the knee joint region and the hip joint region of the support orthosis to generate the joint moments necessary for the support orthosis to make the motion of the leg motion support orthosis following the motion of the person's leg independently (by itself). Therefore, by controlling the torques generated by the torque generation unit according to the feedback control input and the feedforward control input, the estimated values of the actual joint support moments of the knee joint and the hip joint of the each leg can be quickly controlled to the target joint support moments of the knee joint and the hip joint. Moreover, it is possible to effectively reduce forces applied to the person other than forces required to support the motion of the person's legs, such as the weight of the leg motion support orthosis put on the person.

The feedforward control input may be determined according to not only the orthosis-side joint moments, but also the orthosis-side joint moments of the knee joint region and the hip joint region of the each leg link portion and the target joint support moments of the knee joint and the hip joint determined in the sixth step.

BRIEF DESCRIPTION OF THE DRAWINGS

The above and other objects, features and advantages of the present invention will become apparent from the following detailed description when taken with the accompanying drawings in which.

DETAILED DESCRIPTION OF THE PREFERRED EMBODIMENTS

Figure 1:
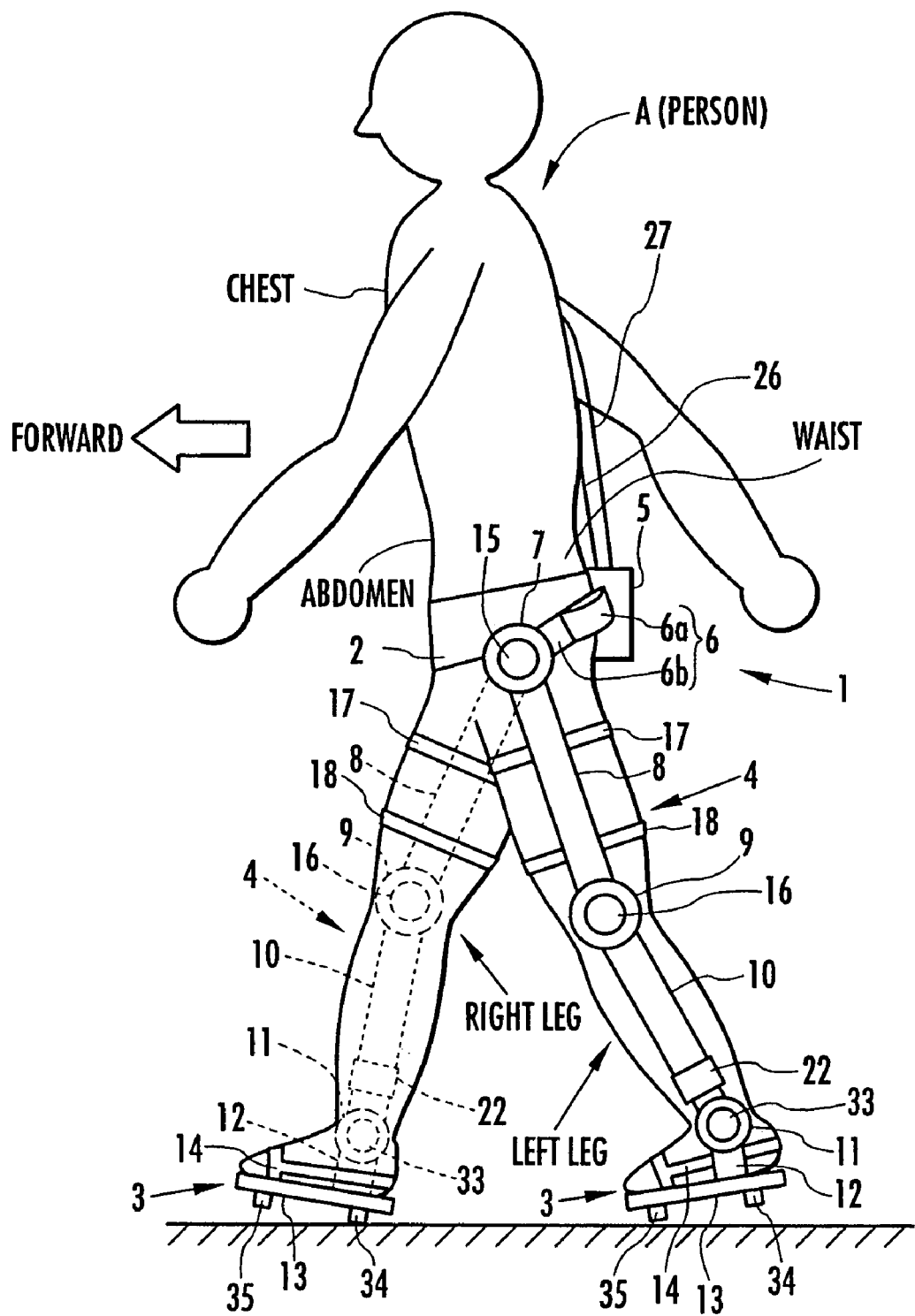
FIG. 1 is a side view showing a person wearing a leg motion support orthosis according to one embodiment of the present invention.
Figure 2:
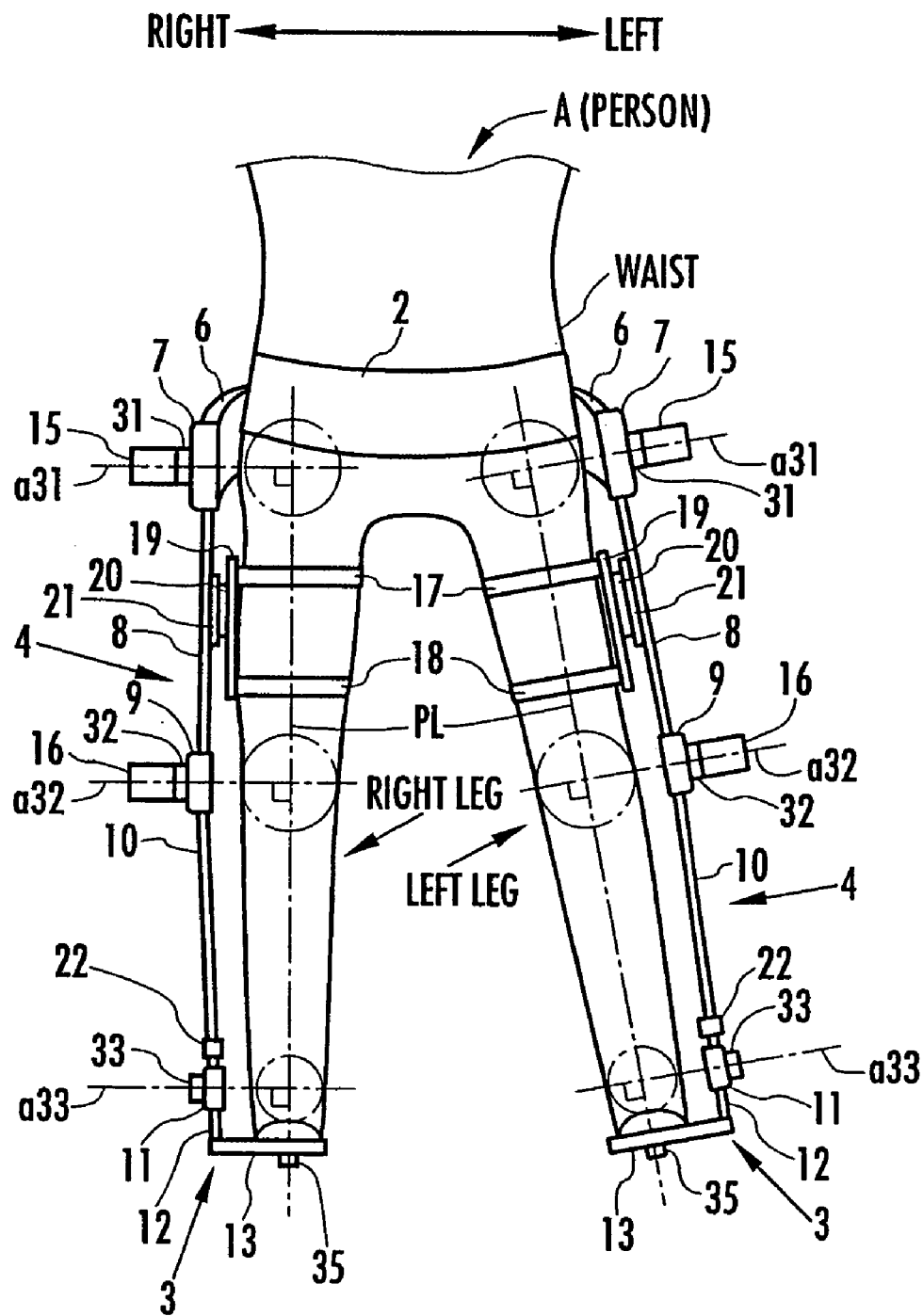
FIG. 2 is a front view of the lower part of the body of the person wearing the leg motion support orthosis.

One embodiment of the present invention will now be described by referring to FIG. 1 to FIG. 26. FIG. 1 shows a state in which a leg motion support orthosis 1 according to this embodiment is put on a person A in the form of a side view. FIG. 2 shows the lower part of the body of the person A wearing the leg motion support orthosis 1 in the form of a front view. In FIG. 2, the hip joint, the knee joint, and the ankle joint of each leg of the person A are each represented by a chain-line circle for convenience of explanation.

In FIG. 1 and FIG. 2, the leg motion support orthosis 1 (hereinafter, simply referred to as the support orthosis 1) includes a waist attachment portion 2 fixed to the waist of the person A, a pair of right and left foot attachment portions 3, 3 fixed to the foot portions of the right and left legs of the person A, respectively, and a pair of right and left leg link portions 4, 4 for coupling the waist attachment portion 2 to the right and left foot attachment portions 3, 3, respectively. The term "right and left" means right and left of the person A facing forward.

The waist attachment portion 2 is formed by a belt member placed around and fixed to the waist and a sensor box 5 containing sensors and the like described later is fixed to the rear of the waist attachment portion 2.

The each leg link portion 4 includes a waist link member 6 extended from the sensor box 5 to the lateral place of the hip joint of the each leg of the person A, a thigh link member 8 extended from the end of the waist link member 6 substantially to the lateral place of the knee joint of the person A via a joint region 7 corresponding to the hip joint (hereinafter, referred to as the hip joint region 7), a crus link member 10 extended from the end (bottom end) of the thigh link member 8 to the lateral place of each ankle joint of the person A via a joint region 9 corresponding to the knee joint (hereinafter, referred to as the knee joint region 9), and a foot link member 12 extended from the end (bottom end) of the crus link member 10 toward the bottom face of the foot portion of the person A via the joint region 11 corresponding to the ankle joint (hereinafter, referred to as the ankle joint region 11). In this instance, the each leg link portion 4 is extending generally along the leg on the lateral surface side of the each leg (on the left side of the left leg or the right side of the right leg) of the person A.

The main body of the each foot attachment portion 3 is formed by a foot base 13 substantially in the form of plate abutting against the bottom face of the each foot portion of the person A and is fixed to the foot portion by tying the foot base 13 to the foot portion of the person A by using a belt member 14. Then, in the foot attachment portion 3, the foot base 13 is fixed to the bottom end of the foot link member 12 of the leg link portion 4 and fixed to the foot link member 12 via the belt member 14, thereby being coupled to the leg link portion 4. In FIG. 2, the belt member 14 is omitted.

In the foot attachment portion 3, the foot base 13 lands while receiving the weight of the person A with the foot portion of the leg put on the foot base 13 of the foot attachment portion 3 in the landing period (a period during which the floor reaction force is applied to the foot portion of the each leg) of the each leg of the person A. Therefore, the floor reaction force, which should act on the each foot portion during the landing period of the person A, mostly (mainly the component balanced with the weight (gravity) of the person A) acts on the foot portion of the person A via the foot base 13 of the foot attachment portion 3, but does not act on the leg link portion 4. The foot attachment portion 3 may be formed by a member, for example, having the shape of a shoe to be put on the foot portion of the person A and may be fixed to the foot link member 12.

The hip joint region 7, the knee joint region 9, and the ankle joint region 11 of the each leg link portion 4 are assumed to be capable of making a rotary motion (a rotary motion around an axis almost perpendicular to the surface of the page of FIG. 1 (more specifically, around an axis substantially perpendicular to a leg plane described later) accompanying a bending and stretching motion of the leg of the person A corresponding to the leg link portion 4. Moreover, in the waist link member 6, a portion 6a relatively close to the sensor box 5 is formed by a hard rigid member and a portion 6b relatively close to the hip joint region 7 is formed by an elastic material such as rubber. The elastic portion 6b is elastically deformed according to an outward or inward swing motion (a motion of rotating the thigh of the leg substantially in the anteroposterior axial direction at the hip joint of the person A) and a slewing motion (a motion of rotating the thigh of the leg around the central axis substantially in the vertical direction at the hip joint of the person A) of the leg of the person A. Thereby, the hip joint region 7 of the each leg link portion 4 (consequently, the lower part than the hip joint region 7 of the each leg link portion 4) is capable of not only rotating according to the bending and stretching motion of the leg of the person A corresponding to the leg link portion 4, but also moving according to the outward or inward swing motion and the slewing motion of the leg of the person A. Moreover, the crus link member 10 is formed in such a way as to be capable of making the motion of the foot attachment portion 3 accompanying the slewing motion around the ankle joint of the foot portion of the person A (a motion of rotating the foot portion around the central axis of the crus), though the detailed description of the structure is omitted here.

In FIG. 1, the central axis of the thigh link member 8 of the each leg link portion 4 and the central axis of the thigh of the person A face the same direction and the central axis of the crus link member 10 and the central axis of the crus of the person A face the same direction for convenience in the illustration. It is not always necessary, however. More specifically, the position of the knee joint region 9 of the each leg link portion 4 may be out of alignment to some extent in an anteroposterior direction or a vertical direction from the lateral place of (at a right angle to) the knee joint of the person A.

Electric motors 15, 16 as torque generation units for generating torques in the joint regions 7, 9 are attached to the hip joint region 7 and the knee joint region 9 of the each leg link portion 4, respectively. These electric motors 15, 16 are disposed on the lateral surface side of the each leg link portion 4. In this instance, the electric motor 15 can generate a torque for rotating the thigh link member 8 around the central axis of the rotation of the hip joint region 7 relative to the waist link member 6, and the electric motor 16 can generate a torque for rotating the crus link member 10 around the central axis of the rotation of the knee joint region 9 relative to the thigh link member 8. The torque generation unit may be formed by, for example, a pneumatic actuator or the like, instead of the electric motor.

As shown in FIG. 2, a plate member 19 fixed to the thigh is disposed via belt members 17, 18 put around the upper part and the lower part of the thigh between the medial surface side of the thigh link member 8 (the facial region facing the thigh of the person A) of the each leg link portion 4 and the thigh of the person A. The plate member 19 is attached to the thigh link member 8 via a sliding mechanism (not shown) and is assumed to be freely movable relative to the thigh link member 8 in the central axis direction of the thigh link member 8 (in the segment direction between the hip joint region 7 and the knee joint region 9). Therefore, the thigh link member 8 is coupled to the thigh of the person A via the plate member 19 and the belt members 17, 18. Moreover, between the plate member 19 and the thigh link member 8, there are disposed a force sensor 20 for detecting a translational force applied from the thigh of the person A to the thigh link member 8 via the plate member 19 (a translational force in a direction perpendicular to the central axis direction of the thigh link member 8) or the reaction force thereof and a displacement sensor 21 for detecting a moving distance of the plate member 19 to the thigh link member 8.

In addition, the force sensor 22 is disposed at the bottom end of the crus link member 10 and the crus link member 10 is coupled to the ankle joint region 11 via the force sensor 22. The force sensor 22 is for use in detecting a resultant force between a floor reaction force applied from the floor to the each leg link portion 4 via the foot attachment portion 3 (more specifically, a floor reaction force applied to the each leg link portion 4 of the support orthosis 1, supposing that the support orthosis 1 is independently making the motion of the support orthosis 1 following the motion of the legs of the person A) and the translational force applied from the foot portion of the person A to the leg link portion 4 via the foot attachment portion 3 or a reaction force of the resultant force, after the resultant force is transmitted via the foot link member 12 and the ankle joint region 11.

Additionally, during the landing period of the each leg of the person A, the weight of the person A acts on the foot base 13 of the foot attachment portion 3, which lands with the foot portion of the person A put thereon, and therefore the weight of the person A does not act on the force sensor 22. More specifically, supposing that the motion of the person A wearing the support orthosis 1 is being made with the support orthosis 1 removed from the person A, most of the floor reaction force (the reaction force kinetically necessary for the person A to make the motion of the person A independently. The total sum of the reaction forces of the both legs is balanced with the total sum of the gravity acting on the single person A and an inertia force generated by the motion of the person A) applied to the each leg of the person A directly acts on the leg of the person A via the foot base 13 and therefore it is hardly transmitted to the each link portion 4. In this embodiment, the ankle joint region 11 of the each leg link portion 4 is not provided with an electric motor or other unit generating torques therein and thus the ankle joint region 11 is free to rotate. Therefore, the resultant force is transmitted to the force sensor 22. In this embodiment, the force sensor 22 may be basically provided in a portion closer to the foot attachment portion 3 than to the knee joint region 9 of the each leg link portion 4: for example, it may be disposed in the foot link member 12 of the each leg link portion 4.

Figure 3:
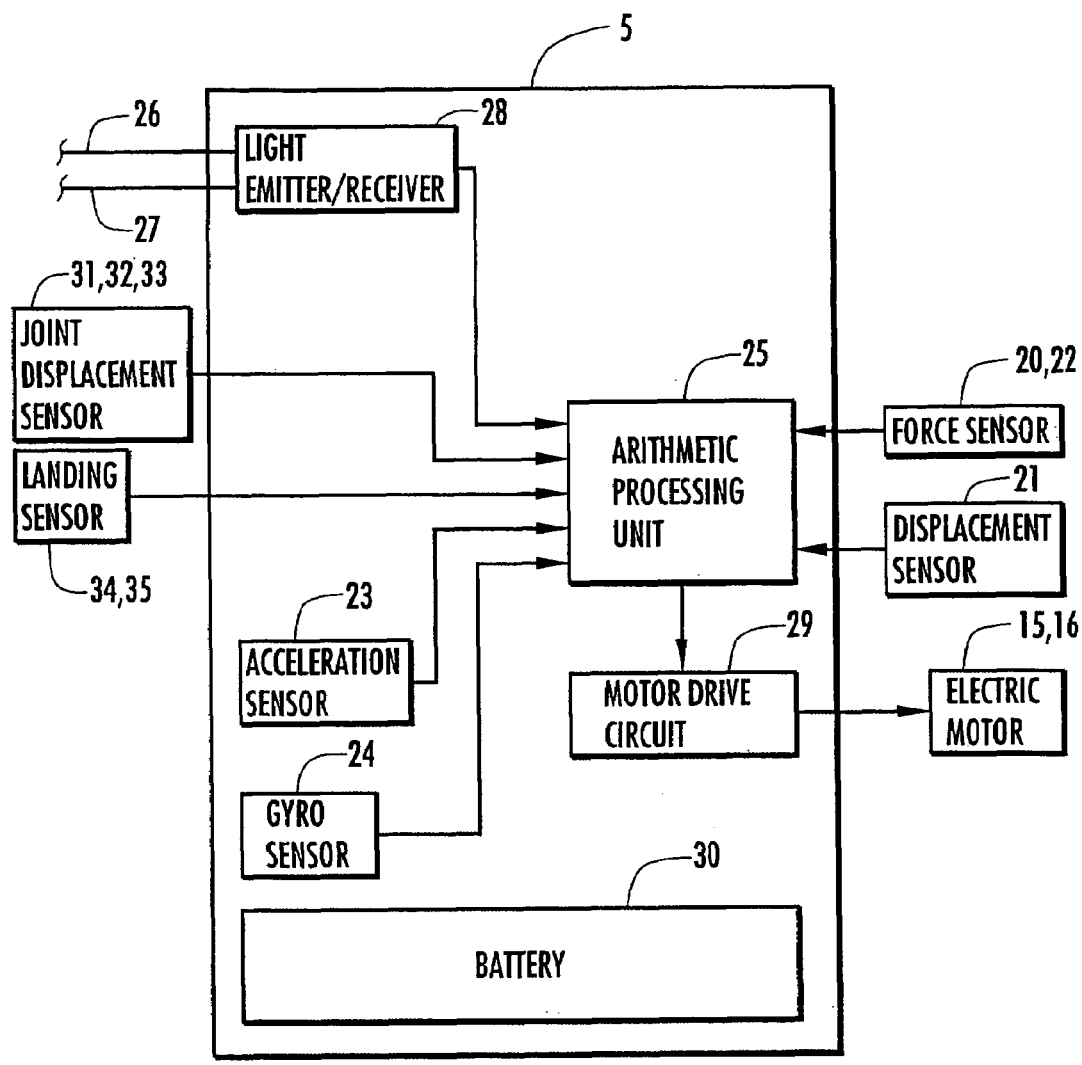
FIG. 3 is a block diagram showing the configuration of the inside of a sensor box of the leg motion support orthosis.

As shown in the block diagram of FIG. 3, the sensor box 5 contains an acceleration sensor 23 for detecting 3-axis acceleration (translation acceleration), a gyro sensor (an angular velocity sensor) 24 for detecting a 3-axis angular velocity, an arithmetic processing unit 25 configured using a microcomputer, an light emitter/receiver 28 for emitting a light to be introduced to optical fibers 26, 27 described later or receiving a feedback light, a motor drive circuit 29 for controlling torques generated by the electric motors 15, 16 upon receiving a command of the arithmetic processing unit 25, and a battery (capacitor) 30 as a power supply for each electrical equipment such as the arithmetic processing unit 25. Detected outputs of the light emitter/receiver 28, the acceleration sensor 23, and the gyro sensor 24 are input to the arithmetic processing unit 25. The sensor box 5 is fixed to the waist of the person A via the waist attachment portion 2 and therefore the acceleration sensor 23 and the gyro sensor 24 move integrally with the waist of the person A.

The support orthosis 1 has a sensing structure as described below, in addition to the displacement sensor 21, the force sensors 20, 22, the acceleration sensor 23, and the gyro sensor 24.

Specifically, as shown in FIG. 2, the hip joint region 7, the knee joint region 9, and the ankle joint region 11 of the each leg link portion 4 are provided with the joint displacement sensors 31, 32, and 33 for detecting displacements (rotation angles) of the respective joint regions, respectively. Detected outputs of the joint displacement sensors 31 to 33 are input to the arithmetic processing unit 25 of the sensor box 5 via signal lines (not shown). Detected outputs of the displacement sensor 21 and the force sensors 20, 22 are also input to the arithmetic processing unit 25 of the sensor box 5 via signal lines (not shown).

The displacement detected by the joint displacement sensor 31 of the hip joint region 7 among the joint displacement sensors 31 to 33 is a 3-axis rotation angle of the hip joint region 7 (three-dimensional amount made of a combination of rotation angles around three axes), the displacement detected by the joint displacement sensor 32 of the knee joint region 9 is a single-axis rotation angle of the knee joint region 9, and the displacement detected by the joint displacement sensor 33 of the ankle joint region 11 is a single-axis rotation angle of the ankle joint region 11. In this instance, the rotation axis of one of the rotation angles detected by the joint displacement sensor 31 and the rotation axes of the rotation angles detected by the joint displacement sensors 32, 33 are, as shown in FIG. 2, axes a31, a32, and a33 substantially perpendicular to the leg plane PL (a plane perpendicular to the surface of the page of FIG. 2) as a plane passing through substantially the center of the hip joint, the knee joint, and the ankle joint of the leg of the person A corresponding to the joint displacement sensors 31 to 33, respectively. These axes a31, a32, and a33 are rotation axes of the hip joint region 7, the knee joint region 9, and the ankle joint region 11, respectively. The joint displacement sensors 31 to 33 detect the rotation angles around the rotation axes a31, a32, and a33 of the hip joint region 7, the knee joint region 9, and the ankle joint region 11, respectively, by using a potentiometer or a rotary encoder.

In this regard, the leg plane PL is supplementarily described. The leg plane PL is a plane where the center points of the hip joint, the knee joint, and the ankle joint of the leg of the person A exist when the person A bends and stretches the corresponding leg by bending the leg at the knee joint. In other words, the each leg is bent and stretched with the center points of the hip joint, the knee joint, and the ankle joint positioned substantially on the leg plane PL. In addition, for example, in a state where the left leg is abducted by a rotary motion around the anteroposterior axis of the hip joint like the left leg shown in FIG. 2, the leg plane PL corresponding to the left leg inclines relative to the vertical direction.

Rotation angles around other two axes detected by the joint displacement sensor 31 of the hip joint region 7 are rotation angles around two axes parallel to the leg plane PL of the corresponding leg, but not parallel to each other (more specifically, rotation angles of the posture of the hip joint region 7 accompanying the outward or inward swing or the slewing of the leg). The rotation angles are detected by using outputs of a strain sensor for detecting a volume of deformation of the elastic portion 6b of the waist link member 6 or a sensor using optical fibers described later.

As shown in FIG. 1, two optical fibers 26, 27 introduced from the sensor box 5 are extended upward along the back face (back) of the body of the person A and their points are fixed to the back face of the abdomen and the back face of the chest of the person A, respectively, via a band or other member (not shown). The optical fibers 26, 27 are components of a detection unit for detecting tilt angles of the abdomen and the chest relative to the waist. The tilt angles of the abdomen and the chest are measured using the optical fibers 26, 27 in the method described below. The method of measuring the tilt angle of the abdomen using the optical fiber 26 will now be typically described. A light having a predetermined intensity is introduced from the light emitter/receiver 28 in the sensor box 5 to the optical fiber 26 and the introduced light is reflected on the end of the optical fiber 26 and returns to the sensor box 5 side. The light emitter/receiver 28 then detects the feedback amount of the light (the intensity of the feedback light). The optical fiber 26 is provided with a plurality of notches (not shown) allowing subtle light leakage disposed at intervals in the longitudinal direction. Light of the amount according to the tilt angle of the abdomen relative to the waist leaks from the optical fiber 26 via the notches, out of the light introduced into the optical fiber 26. Therefore, the feedback amount of the light to the sensor box 5 side depends upon the tilt angle of the abdomen and the tilt angle of the abdomen relative to the waist is measured by detecting the feedback amount. In other words, the detected outputs of the light emitter/receiver 28 according to the feedback amount of the light of the optical fiber 26 depends upon the tilt angle of the abdomen relative to the waist and it is input to the arithmetic processing unit 25 as a signal indicating the tilt angle. The same applies to the method of measuring the tilt angle of the chest using the optical fiber 27. In this embodiment, the tilt angles of the abdomen and the chest detected as described above by using the optical fibers 26, 27 are those on the sagittal plane (side view) of the person A.

As supplementary information, the rotation angles of the hip joint region 7, the knee joint region 9, and the ankle joint region 11 detected by the joint displacement sensors 31 to 33 are measured with reference (zero point) to a condition where the each leg link portion 4 of the support orthosis 1 is extended substantially in the vertical direction and the foot base 13 of the foot attachment portion 3 is put in the substantially horizontal position (the condition is hereinafter referred to as a reference posture condition of the support orthosis 1). Moreover, the tilt angles of the abdomen and the chest detected by using the optical fibers 26, 27 are measured with reference to a condition where the person A wearing the support orthosis 1 stands up with a standing posture (the posture of the person A directing the each leg and the body substantially in the vertical direction) on a horizontal floor (the condition is hereinafter referred to as a reference posture condition of the person A).

Moreover, as shown in FIG. 1 the support orthosis 1 has two landing sensors 34, 35 on the bottom face of the foot base 13 of the each foot attachment portion 3. Regarding the landing sensors 34, 35, the landing sensor 34 is disposed in the part (heel) just under the ankle joint of the person A and the landing sensor 35 is disposed in the part (tiptoe) just under the metatarsophalangeal joint of the foot portion (a joint at the root of the big toe of the foot portion) of the person A. These landing sensors 34, 35 output ON/OFF signals indicating whether the parts where they are disposed are in contact with the ground. Incidentally, detected outputs of the landing sensors 34, 35 are input to the arithmetic processing unit 25 of the sensor box 5 via signal lines (not shown).

The configuration of the support orthosis 1 according to this embodiment has been described hereinabove.

Figure 4:
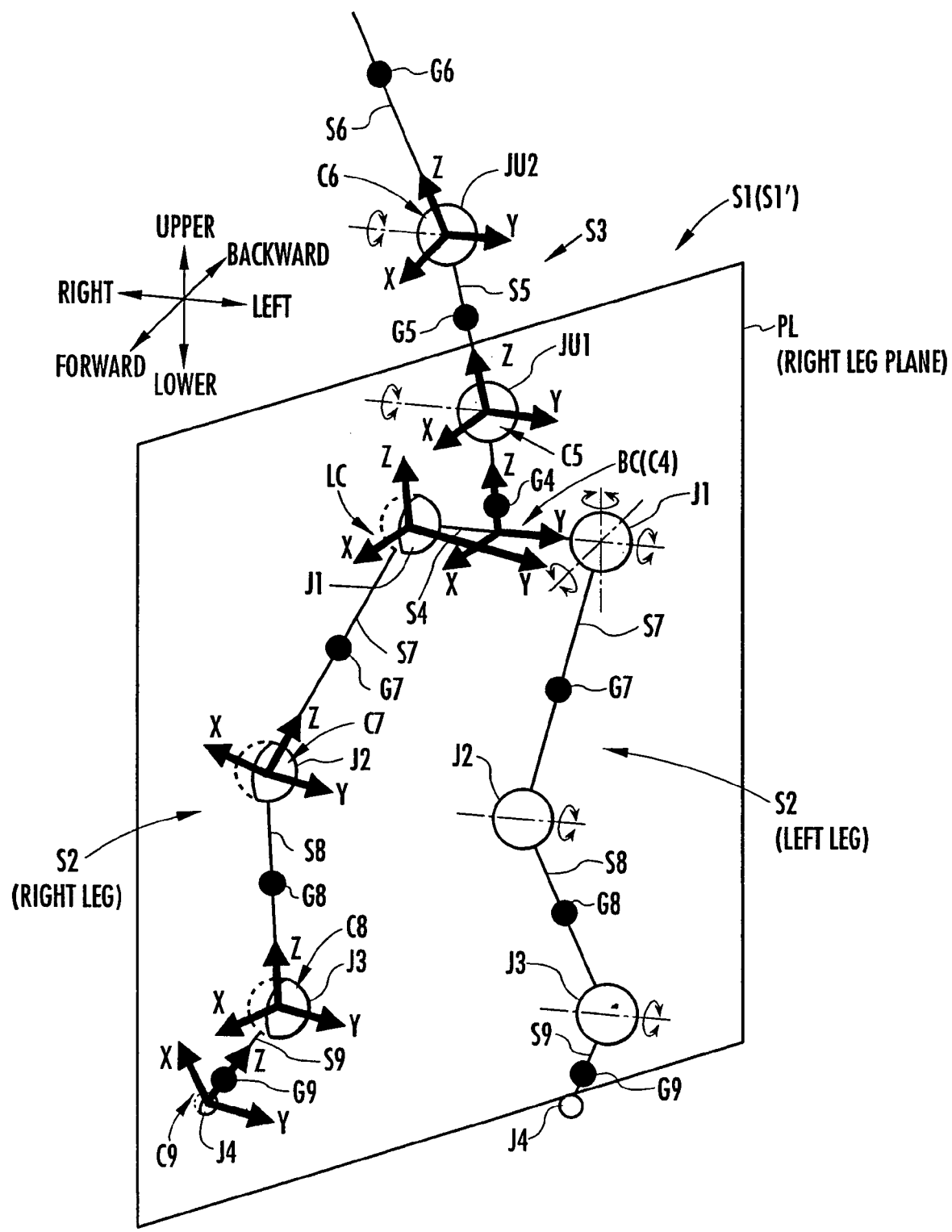
FIG. 4 is a diagram showing the structure of a human-side rigid link model and an orthosis-side rigid link model for use in the control processing of the leg motion support orthosis.

The following describes a rigid link model (geometric model) of the person A, a rigid link model (geometric model) of the support orthosis 1, and coordinate systems used in this embodiment. Referring to FIG. 4, there is shown a structure and a coordinate system for the rigid link model S1 of the person A. As described later, the basic structure of the rigid link model of the support orthosis 1 is assumed to be the same as that of the rigid link model S1 of the person A in this embodiment. Therefore, FIG. 4 shows the structure of the rigid link model of the support orthosis 1, too. Accordingly, the reference symbol S1' indicating the rigid link model of the support orthosis 1 is put in parentheses in FIG. 4.

As shown in FIG. 4, the rigid link model S1 of the person A is represented as a link body formed of nine rigid elements and eight joint elements in this embodiment. In FIG. 4, each rigid element is represented by a line segment and each joint element is represented by a circle (except one indicated by the reference character J4). More specifically, the rigid link model S1 includes roughly a pair of legs S2, S2 corresponding to the legs of the person A and an upper body S3 corresponding to the upper part of the body (the upper part from the waist) of the person A. The upper body S3 is configured as a link body wherein a rigid element S4 corresponding to the waist of the person A is coupled to a rigid element S5 corresponding to the abdomen of the person A via a joint element JU1 and further the rigid element S5 is coupled to a rigid element S6 corresponding to the chest via a joint element JU2. Hereinafter, the rigid elements S4 to S6 are respectively referred to as a waist element S4, an abdomen element S5, and a chest element S6 in some cases, and the joint elements JU1 and JU2 are respectively referred to as a lower joint of the upper body JU1 and an upper joint of the upper body JU2 in some cases.

In this instance, the lower joint of the upper body JU1 is disposed at the upper end of the waist element S4 and a pair of joint elements J1, J1 corresponding to a pair of hip joints of the person A (hereinafter, simply referred to as the hip joint J1 in some cases) are disposed at both right and left ends of the lower part of the waist element S4. Moreover, the lower joint of the upper body JU1 corresponds to a joint supposed on the backbone of the person A in the vicinity of the border between the waist and the abdomen of the person A, and the upper joint of the upper body JU2 corresponds to a joint supposed on the backbone of the person A in the vicinity of the border between the abdomen and the chest. In the rigid link model S1, the bending motion of the upper body S3 corresponding to the bending motion of the body of the person A is made by two joint elements of the lower joint of the upper body JU1 and the upper joint of the upper body JU2.

The each leg S2 of the rigid link model S1 is configured as a link body wherein a thigh element S7 as a rigid element corresponding to the thigh of the person A is coupled to the waist element S4 via the hip joint J1, a crus element S8 as a rigid element corresponding to the crus is coupled to the thigh element S7 via a joint element J2 corresponding to the knee joint, and a foot element S9 as a rigid element corresponding to the foot portion is coupled to the crus element S8 via a joint element J3 corresponding to the ankle joint. Hereinafter, the joint elements J2, J3 are simply referred to as a knee joint J2 and an ankle joint J3, respectively, in some cases.

In FIG. 4, the part indicated by the reference character J4 at the tip of the foot element S9 corresponds to the metatarsophalangeal joint (hereinafter, referred to as the MP joint), which is a joint at the root of the big toe of the foot portion of the person. In the rigid link model S1, the part J4 does not function as a joint, but hereinafter the part J4 is referred to as the MP joint J4 for convenience.

The rigid elements and the joint elements of the rigid link model S1 of the person A configured as described above are capable of making motions in such a way that the mutual positional relationship and posture relationship (directional relationship) of the elements are coincident with the mutual positional relationship and posture relationship of the portions of the person corresponding to the rigid elements and the joint elements by means of the rotary motions of the joint elements. In this instance, the lower joint of the upper body JU1 and the upper joint of the upper body JU2 can rotate around three axes. By using one of the three axes as a measurement axis, a rotation around the measurement axis (See arrows (rotation arrows) corresponding to the joint elements JU1, JU2 shown in FIG. 4) is measured. In this embodiment, the measurement axis is parallel to a line segment connecting the centers of the pair of hip joints J1, J1 (parallel to the Y axis of a body coordinate system BC described later). The hip joint J1 of the each leg S2 can rotate around three axes as indicated by arrows (rotation arrows) typically shown in FIG. 4 regarding the hip joint J1 of the left leg S2. The knee joint J2 and the ankle joint J3 of the each leg S2 can rotate around a single axis as indicated by the arrows (rotation arrows) typically shown in FIG. 4 regarding the joint elements J2, J3 of the left leg S2. The rotation axis of the knee joint J2 and that of the ankle joint J3 are perpendicular to the leg plane PL passing through the centers of the hip joint J1, the knee joint J2, and the ankle joint J3 (not shown for the left leg S2 in FIG. 4). The rotating motion of the hip joint J1, the knee joint J2, and the ankle joint J3 of the right leg S2 is the same as in the left leg S2. In. this instance, the each rotation axis (a single axis) of the knee joint J2 and the ankle joint J3 of the right leg S2 is perpendicular to the leg plane PL shown correspondingly to the right leg S2. The each hip joint J1 can rotate around the three axes regarding the both legs S2 and therefore can rotate around the axis perpendicular to the leg plane PL corresponding to the each leg S2.

In the rigid link model S1, the weight, the length (the length in the segment direction in FIG. 4), and the moment of inertia of the each rigid element and the center of gravity location of the each rigid element (the position in the element coordinate system fixed to the each rigid element described later) are predetermined and then stored in a memory (not shown) in the arithmetic processing unit 25. Black dots G6, G5, G4, G7, G8, and G9 shown in FIG. 4 illustratively indicate the centers of gravity of the chest element S6, the abdomen element S5, the waist element S4, the thigh element S7, the crus element S8, and the foot element S9, respectively. As supplementary information, the waist element S4 is coupled to the three joint elements JU1, J1, and J1 and therefore the length of the waist element S4 includes the length of a line segment between the both hip joints J1, J1 and the length of a line segment between the midpoint of the above line segment and the lower joint of the upper body JU1. Instead of the length of the each rigid element, the positions of the both endpoints of the rigid element in the element coordinate system fixed to the rigid element may be previously stored in the arithmetic processing unit 25.

The weight, the length, the moment of inertia, and the center of gravity location of the each rigid element of the rigid link model S1 are basically set so as to be substantially coincident with the weight, the length, the moment of inertia, and the center of gravity location of the region (rigid equivalent part) of the person A corresponding to the each rigid element. For example, the weight, the length, the moment of inertia, and the center of gravity location of the thigh element S7 are substantially the same as the actual weight, length, moment of inertia, and center of gravity of the thigh of the person A. The weight, the length, the moment of inertia, and the center of gravity location of the each rigid element of the rigid link model S1 are the weight, the length, the moment of inertia, and the center of gravity location in the condition where the person A is not wearing the support orthosis 1 (only of the person A). Moreover, the weight, the moment of inertia, and the center of gravity location of the chest element S6 are the weight, the moment of inertia, and the center of gravity location of the chest, and both arms, and the head of the person A included. As supplementary information, the change in the center of gravity location of the chest element S6 accompanying the motion of the both arms (the motion of swinging the arms back and forth) of the person A when walking is relatively small and therefore the center of gravity location is maintained at a substantially fixed position of the chest element S6.

While the weight, the length, the moment of inertia, and the center of gravity location of the each rigid element of the rigid link model S1 may be basically determined based on the actual measurements of the size or the weight of each part of the person A, it is also possible to estimate them on the basis of average statistical data of a human being from the height and the weight of the person A. In general, the center of gravity location, the weight, the length, and the moment of inertia of the rigid equivalent part of the person A corresponding to the each rigid element have a correlation with the height and the weight (the entire weight) of a human being, and it is possible to estimate the center of gravity location, the weight, the length, and the moment of inertia of the rigid equivalent part of the person A corresponding to the each rigid element relatively precisely from measurement data of the height and the weight of the person A on the basis of the correlation.

Although centers of gravity G4 to G9 are located on the central axis of the rigid elements corresponding to them respectively (on the shown line segments) in FIG. 4 for convenience, they are not necessarily located on the central axis, but can exist in the positions deviating from the central axis.

In this embodiment, a coordinate system as described below is preset for the rigid link model S1. More specifically, as shown in FIG. 4 the body coordinate system BC is set with being fixed to the waist element S4. The body coordinate system BC is established as a three-dimensional coordinate system (XYZ coordinate system) whose origin is defined as being the midpoint of a line segment between the centers of the pair of hip joints J1, J1, whose Y axis is defined as being in the direction of the line segment, whose Z axis is defined as being in the direction from the origin to the center of the lower joint of the upper body JU1, and whose X axis is defined as being in the direction perpendicular to the Y axis and the Z axis. In the reference posture condition of the person A, the X axis, the Y axis, and the Z axis of the body coordinate system BC are oriented in the forward/backward direction, the horizontal direction, and the vertical direction of the person A, respectively, and the XY plane is a horizontal plane.

A leg coordinate system LC is fixed to and set at one joint element of the each leg S2 such as, for example, the hip joint J1. In FIG. 4, only the leg coordinate system LC corresponding to the right leg S2 is typically shown for convenience. The leg coordinate system LC is a three-dimensional coordinate system where one of its coordinate axes is perpendicular to a leg plane PL of the leg S2 corresponding to the leg coordinate system LC. In this embodiment, specifically the leg coordinate system LC is defined as a coordinate system whose origin is the center of the hip joint J1, whose Y axis is in the direction perpendicular to the leg plane PL, whose Z axis is in the direction parallel to the axis generated by projecting the Z axis of the body coordinate system BC onto the leg plane PL, and whose X axis is in the direction perpendicular to the Y axis and the Z axis. Therefore, the leg coordinate system LC is, in other words, a coordinate system where the XZ plane matches the leg plane PL.

Moreover, an element coordinate system is fixedly set at the each rigid element as indicated by the reference characters C4 to C9, for example. In this embodiment, the element coordinate system C4 of the waist element S4 is defined as being coincident with the body coordinate system BC. Moreover, the element coordinate systems C6, C5, C7, C8, and C9 of the chest element S6, the abdomen element S5, the each thigh element S7, the each crus element S8, and the each foot element S9 are defined as being three-dimensional coordinate systems (XYZ coordinate systems) whose origins are at the center of the upper joint of the upper body JU2, the lower joint of the upper body JU1, the knee joint J11, the ankle joint J13, and the MP joint J4, respectively.

The element coordinate systems C4 to C9 need not be necessarily set as described above only if they are fixed to the corresponding rigid elements, but can be set with an arbitrary origin or arbitrary directions of axes. Moreover, the origin of the leg coordinate system LC may be deviated from the center of the hip joint J1 or the body coordinate system BC may be fixed to or set at a region different from the waist element S4. How to set the coordinate systems may be basically arbitrary and thus a wide variety of setting methods can be employed. Therefore, how to set the coordinate systems in this embodiment is illustrative only.

Subsequently, the rigid link model of the support orthosis 1 is described below. In this embodiment, the coupling structure of the rigid link model of the support orthosis 1 is the same as that of the rigid link model S1 of the person A (hereinafter, referred to as the "human rigid link model S1"), having the structure shown in FIG. 4. Therefore, the rigid link model of the support orthosis 1 is described by using FIG. 4. Hereinafter, the rigid link model of the support orthosis 1 is represented by a reference character S1' with parentheses as shown in FIG. 4 and referred to as the orthosis rigid link model S1'.

In this instance, the joint elements J1 to J3 of the each leg S2 of the orthosis rigid link model S1' correspond to the hip joint region 7, the knee joint region 9, and the ankle joint region 11 of the support orthosis 1, respectively. Moreover, the joint elements JU1 and JU2 of the upper body S3 correspond to joints supposed on the backbone of the person A in the same manner as for the person A. In this embodiment, the rotations that can be made by the joint elements J1 to J3, JU1, and JU2 of the orthosis rigid link model S1' are the same as those of the human rigid link model S1.

The rigid elements S4 to S9 of the orthosis rigid link model S1' correspond to portions put on the regions of the person A corresponding to the rigid elements or portions integrally movable with the regions in the support orthosis 1. For example, the waist element S4 of the orthosis rigid link model S1' corresponds to the portion formed of the waist attachment portion 2, the sensor box 5, and the waist link member 6 of the support orthosis 1. Moreover, for example, the each thigh element S5 of the orthosis rigid link model S1' corresponds to a portion between the hip joint region 7 and the knee joint region 9 of the each leg link portion 4 of the support orthosis 1 (the portion formed of the thigh link member 8, a slide mechanism (not shown), the plate member 19, the belt members 17 and 18, the displacement sensor 21, and the force sensor 20). The same applies to other rigid elements. Regarding the joint regions 7, 9, and 11 of the each leg link portion 4 and the attachments (the electric motors 15, 16 and the joint displacement sensors 31 to 33) to the joint regions of the support orthosis 1, half bodies of the joint regions 7, 9, and 11 and those of the attachments to the joint regions are assumed to be included in the rigid elements coupled via the joint elements corresponding to the joint regions, respectively. For example, regarding the hip joint region 7 of the support orthosis 1 and the joint displacement sensor 31 and the electric motor 15 attached to the hip joint region 7, their half bodies are assumed to be included in the waist element S4 and the thigh element S7.

The weight, the length, the moment of inertia, and the center of gravity location (the location on the element coordinate system fixed to the each rigid element) of the rigid elements S4 to S9 of the orthosis rigid link model S1' are previously stored in the memory of the arithmetic processing unit 25. In this instance, the element coordinate system of the each rigid element is set in the same manner as for the human rigid link model S1, for example. Moreover, the weight, the moment of inertia, and the center of gravity location of the rigid elements S4 to S9 of the orthosis rigid link model S1' are the weight, the moment of inertia, and the center of gravity location of the support orthosis 1 itself (the support orthosis 1 removed from the person A).

Moreover, regarding the coordinate system of the orthosis rigid link model S1', the element coordinate system C4 of the waist element S4 of the orthosis rigid link model S1' is assumed to be the same as the element coordinate system C4 (=the body coordinate system BC) of the waist elements S4 of the human rigid link model S1 in this embodiment. Furthermore, the leg coordinate system LC of the left leg S2 of the orthosis rigid link model S1' is defined as a coordinate system whose origin is the center of the left hip joint J1 of the orthosis rigid link model S1' and whose XZ plane is parallel to the left leg plane PL (whose Y axis is perpendicular to the left leg plane PL) in the same manner as for the leg coordinate system LC of the left leg S2 of the human rigid link model S1. The same applies to the leg coordinate system LC of the right leg S2 of the orthosis rigid link model S1'. Moreover, since the foot attachment portion 3 of the support orthosis 1 is fixed to the foot portion of the person A, the element coordinate system C9 of the each foot element S9 of the orthosis rigid link model S1' is assumed to be the same as the element coordinate system C9 of the each foot element S9 of the human rigid link model S1 in this embodiment. Incidentally, the positional relationship between the center of the hip joint of the person A and the center of the hip joint region 7 of the support orthosis 1 with the support orthosis 1 put on the person A is substantially fixed, and therefore the leg coordinate system LC in the orthosis rigid link model S1' may be the same as the leg coordinate system LC in the human rigid link model S1.

Figure 5:
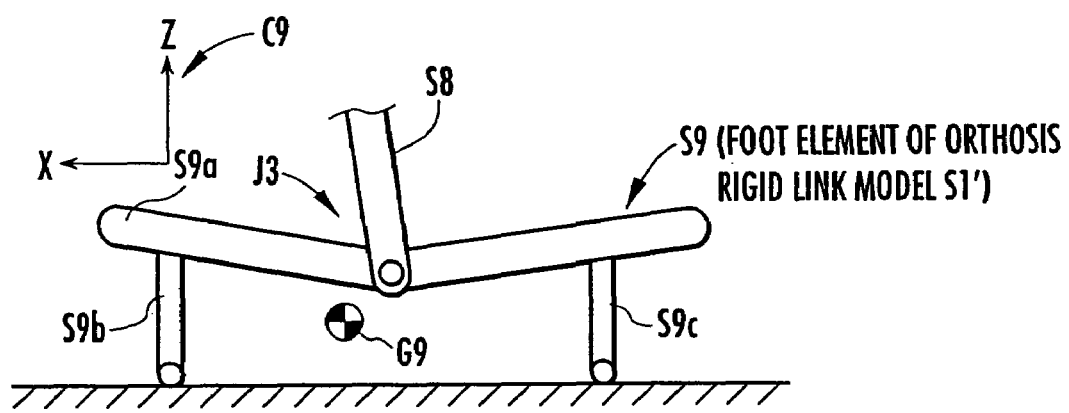
FIG. 5 is a diagram showing the structure of a foot portion of the orthosis-side rigid link model.

As supplementary information, the each foot element S9 is assumed to have more specifically a structure shown in FIG. 5 in the orthosis rigid link model S1' in this embodiment. In other words, a foot base S9a substantially in the form of flat plate is coupled to the ankle joint J3 and support members S9b, S9c put in contact with the floor are respectively provided on the under surface of the front part (the part relatively close to the toe) and the rear part (the part relatively close to the heel) of the foot base S9a. Moreover, regarding the foot element S9 of the orthosis rigid link model S1', the positions of the support members S9b, S9c (the positions of the bottom edges of the support members S9b, S9c) on the element coordinate system C9 of the foot element S9 are stored in the memory of the arithmetic processing unit 25, instead of the length.

In this embodiment, the positions and the postures of the lower joint of the upper body JU1, the upper joint of the upper body JU2, the abdomen element S5, and the chest element S6 of the orthosis rigid link model S1' on the body coordinate BC are assumed to be coincident with the positions and the postures of the lower joint of the upper body JU1, the upper joint of the upper body JU2, the abdomen element S5, and the chest element S6 of the human rigid link model S1, respectively. The weight and the moment of inertia of the portions of the support orthosis 1 corresponding to the abdomen and the chest of the person A are sufficiently low in comparison with the weight and the moment of inertia of other portions, and therefore there is no problem to assume them to be zero. Therefore, the upper elements than the waist element S4 of the orthosis rigid link model S1' or the lower joint of the upper body JU1, the abdomen element S5, the upper joint of the upper body JU2, and the chest element S6 may be omitted.

The human rigid link model S1 and the orthosis rigid link model S1' are assumed to have the similar momentary postures (positional and posture relations between the elements) to those of the person A and the support orthosis 1, respectively. Therefore, in the following description, the elements of the human rigid link model S1 are often identified with the regions of the person A corresponding to the elements and then the elements of the human rigid link model S1 are sometimes used as equivalents to the regions of the person A corresponding to the elements. For example, the each leg S2 of the human rigid link model S1 is sometimes used as an equivalent to the each leg of the person A. It is assumed that the same applies to the relation between the elements of the orthosis rigid link model S1' and the regions of the support orthosis 1 corresponding to the elements. For example, the each leg S2, the thigh element S7, the crus element S8, and the foot element S9 of the orthosis rigid link model S1' are sometimes used as equivalents to the each leg link portion 4 (including the foot attachment portion 3 in this case), the thigh link member 8, the crus link member 10, and the foot attachment portion 3 of the support orthosis 1, respectively.

Figure 6:
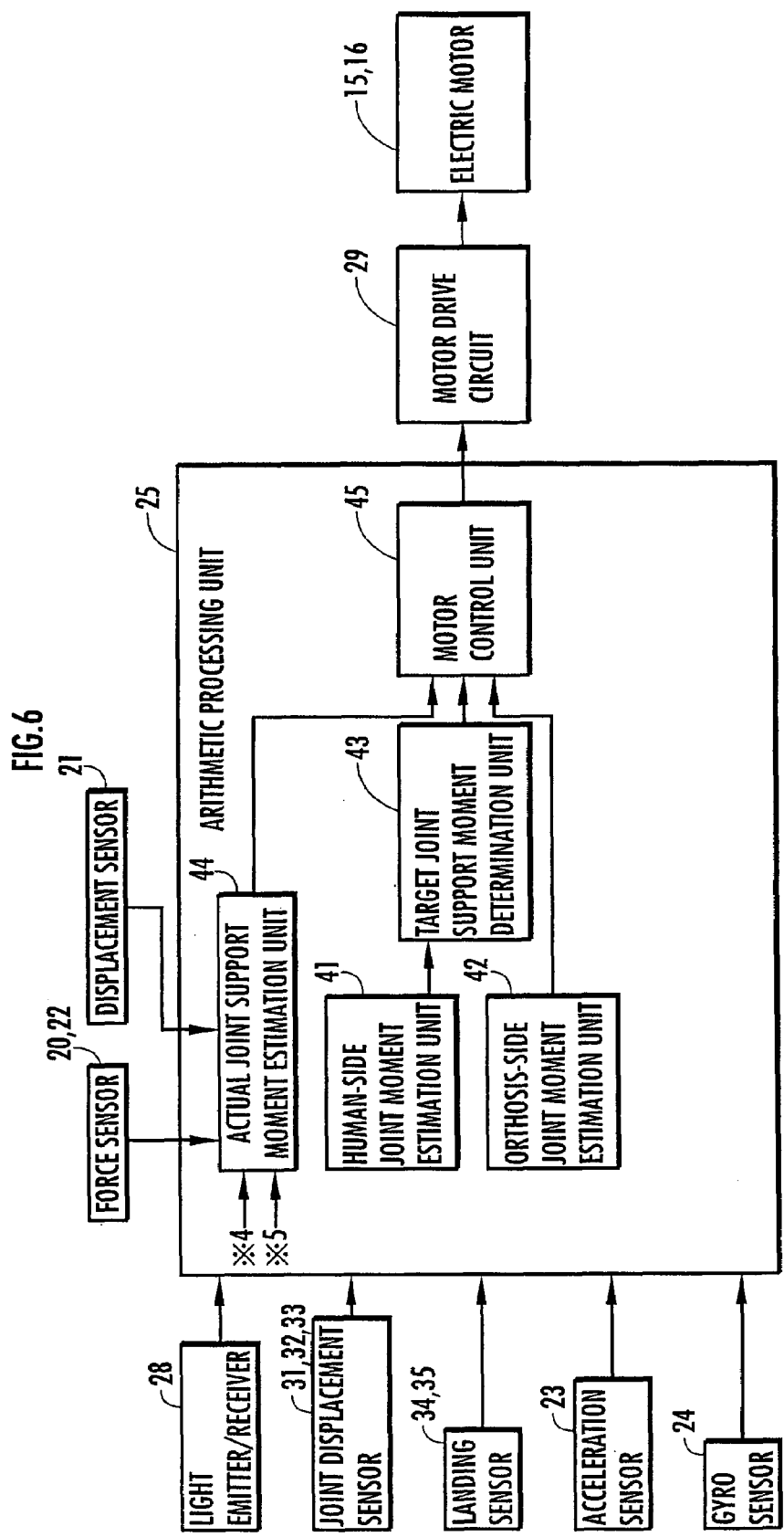
FIG. 6 is a block diagram showing an outline of a processing function of an arithmetic processing unit shown in FIG. 3.
Figure 7:
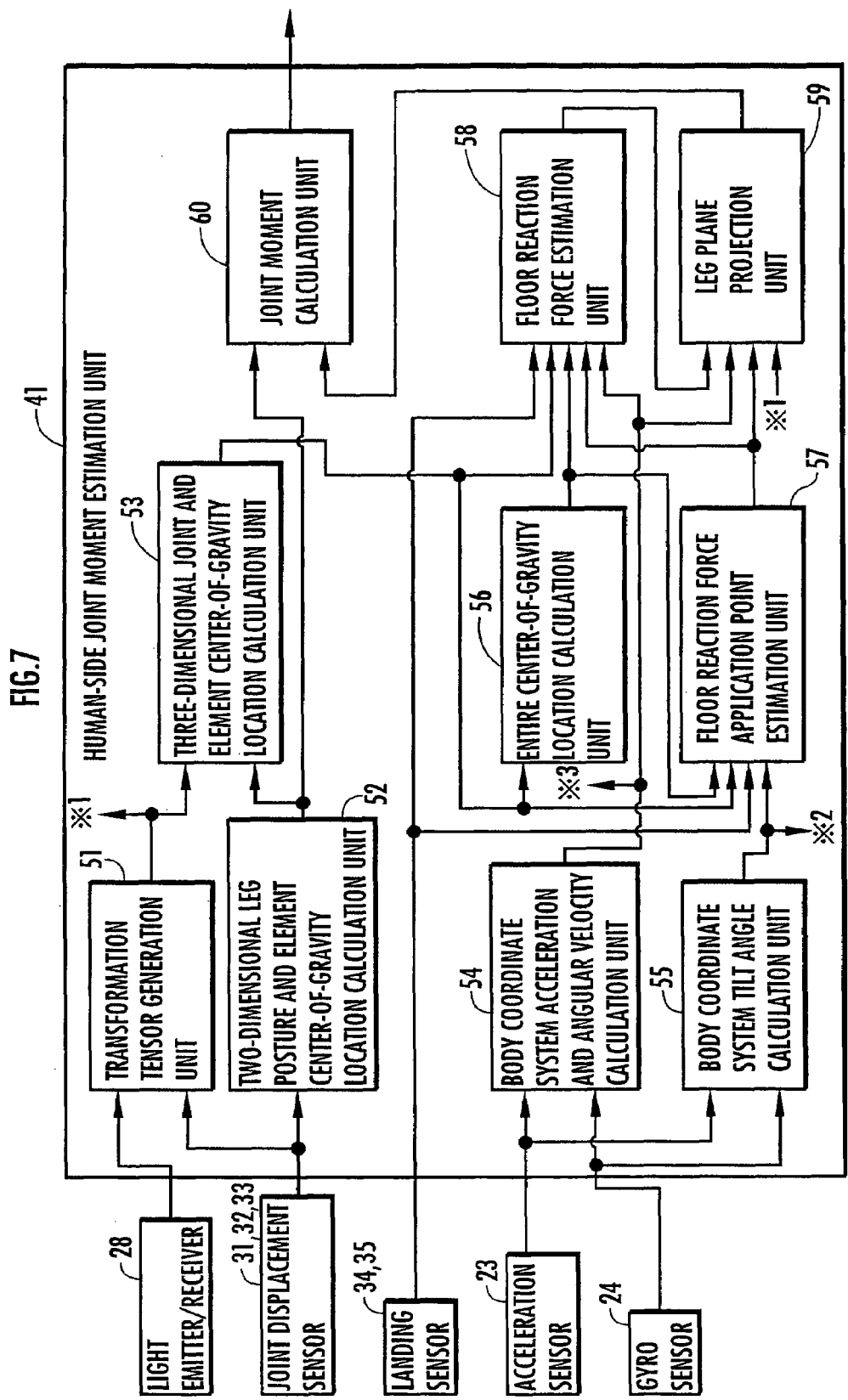
FIG. 7 is a block diagram showing detailed functions of a human-side joint moment estimation unit shown in FIG. 6.
Figure 8:
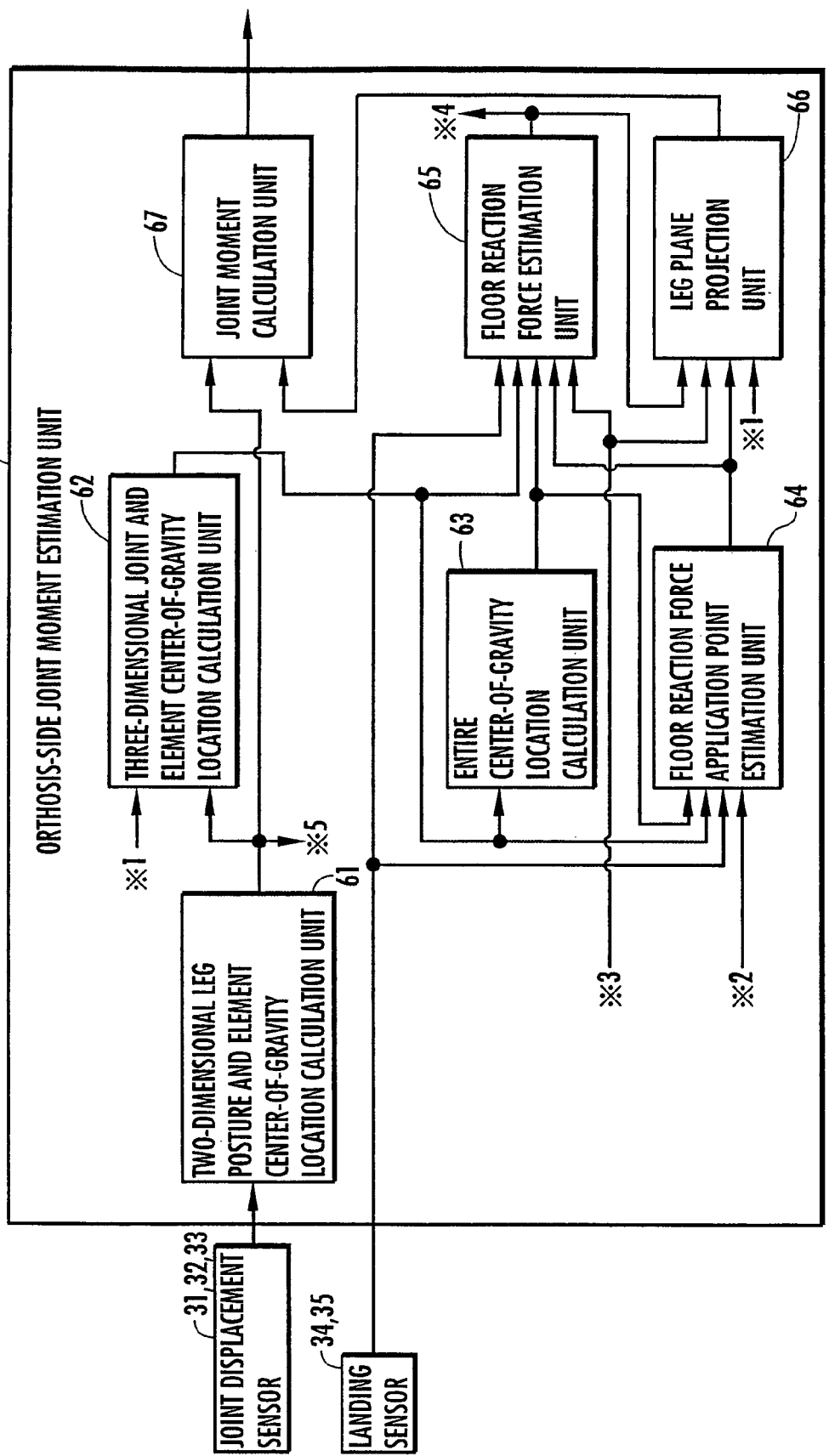
FIG. 8 is a block diagram showing detailed functions of an orthosis-side joint moment estimation unit shown in FIG. 6.

The following describes an outline of processing functions of the arithmetic processing unit 25. FIG. 6 is a block diagram schematically showing the entire processing functions of the arithmetic processing unit 25. FIG. 7 and FIG. 8 are block diagrams showing processing functions of the essential parts of the arithmetic processing unit 25.

The processing functions of the arithmetic processing unit 25 can be roughly classified into as follows: a human-side joint moment estimation unit 41 for sequentially estimating joint moments to be generated at the joints (the ankle joint, the knee joint, and the hip joint) of the each leg of the person A, supposing that the leg motion is being made with the support orthosis 1 removed from the person A (supposing that the person A is making a desired motion of the each leg by him or herself without wearing the support orthosis 1) during the leg motion of the person A (such as walking of the person A); an orthosis-side joint moment estimation unit 42 for sequentially estimating joint moments to be generated at the joint regions 7, 9, 11 of the support orthosis 1, supposing that the support orthosis 1 is independently making the motion of the support orthosis 1 following the leg motion of the person A (the support orthosis 1 removed from the person A is making the motion by itself); a target joint support moment determination unit 43 for determining target joint support moments, which are target moments that should be generated at the hip joint and the knee joint of the each leg by operating the electric motors 15 and 16 of the support orthosis 1, according to the joint moments estimated by the human-side joint moment estimation unit 41; an actual joint support moment estimation unit 44 for sequentially calculating estimated values of actual joint support moments, which are joint moments actually generated at the hip joint and the knee joint of the person A by operating the electric motors 15, 16 of the support orthosis 1, on the basis of outputs of the force sensors 20, 22 and the displacement sensor 21 or the like; and a motor control unit 45 for feedback-controlling the electric motors 15, 16 via the motor drive circuit 29 in such a way that the estimated values of the actual joint support moments of the hip joint and the knee joint are coincident with the target joint support moments by using the estimated values of the joint moments of the joint regions 7, 9, and 11 estimated by the orthosis-side joint moment estimation unit 42, the target joint support moments of the hip joint and the knee joint determined by the target joint support moment determination unit 43, and the actual joint support moments of the knee joint and the hip joint estimated by the actual joint support moment estimation unit 44.

In this instance, more specifically as shown in FIG. 7, the human-side joint moment estimation unit 41 includes: a transformation tensor generation unit 51 for generating a transformation tensor for use in a coordinate transformation described later on the basis of detected outputs of the joint displacement sensor 31 and the light emitter/receiver 28 in the each hip joint region 7; a two-dimensional leg posture and element center-of-gravity location calculation unit 52 for calculating locations of the joint elements, postures (tilt angles) of the rigid elements, and the center of gravity locations of the rigid elements on the leg plane PL of the each leg S2 of the human rigid link model S1 on the basis of detected outputs of the joint displacement sensors 31, 32, and 33; a three-dimensional joint and element center-of-gravity location calculation unit 53 for calculating three-dimensional position vector values (coordinate component values) on the body coordinate system BC of the centers of gravity of the joint elements and the rigid elements of the human rigid link model S1 by using the transformation tensor generated by the transformation tensor generation unit 51 and the locations and postures calculated by the two-dimensional leg posture and element center-of-gravity location calculation unit 52; a body coordinate system acceleration and angular velocity calculation unit 54 for calculating values of an acceleration vector (translation acceleration) and the angular velocity vector of the origin of the body coordinate system BC (coordinate component values on the body coordinate system BC) on the basis of detected outputs of the acceleration sensor 23 and the gyro sensor 24; and a body coordinate system tilt angle calculation unit 55 for calculating a tilt angle relative to the vertical direction of the body coordinate system BC on the basis of detected outputs of the acceleration sensor 23 and the gyro sensor 24. The position vector calculated by the three-dimensional joint and element center-of-gravity location calculation unit 53 includes a position vector on the body coordinate system BC of the MP joint J4 of the each foot element S9 of the human rigid link model S1.

Moreover, the human-side joint moment estimation unit 41 includes an entire center-of-gravity location calculation unit 56 for calculating a value of the position vector of the entire center of gravity (the entire center of gravity of the person A) of the human rigid link model S1 on the body coordinate system BC by using the position vectors of the centers of gravity of the rigid elements of the human rigid link model S1 calculated by the three-dimensional joint and element center-of-gravity location calculation unit 53.

Moreover, the human-side joint moment estimation unit 41 includes: a floor reaction force application point estimation unit 57 for calculating a value on the body coordinate system BC of the position vector of the application point of the floor reaction (a vector of a translation floor reaction force) (hereinafter, simply referred to as the floor reaction force application point) acting on the each leg (the each leg S2) by using the position vector values of the each ankle joint J3 and the each MP joint J4 calculated by the three-dimensional joint and element center-of-gravity location calculation unit 53, the tilt angle of the body coordinate system BC calculated by the body coordinate system tilt angle calculation unit 55, the position vector value of the entire center of gravity calculated by the entire center-of-gravity location calculation unit 56, and the detected outputs of the landing sensors 34, 35; and a floor reaction force estimation unit 58 for estimating a value (a coordinate component value) on the body coordinate system BC of the floor reaction force (a vector of the translation floor reaction force) applied to the each leg of the person A by using the position vector values of the centers of gravity of the joint elements and of the rigid elements calculated by the three-dimensional joint and element center-of-gravity location calculation unit 53, the position vector value of the entire center of gravity calculated by the entire center-of-gravity location calculation unit 56, the values of the acceleration vector and the angular velocity vector of the origin of the body coordinate system BC calculated by the body coordinate system acceleration and angular velocity calculation unit 54, detected outputs of the landing sensors 34, 35, and the position vector value of the floor reaction force application point calculated by the floor reaction force application point estimation unit 57. The floor reaction force estimated by the floor reaction force estimation unit 58 is, more specifically, a floor reaction force applied to the each leg of the person A, supposing that the motion of the person A is being made with the support orthosis 1 removed from the person A.

The human-side joint moment estimation unit 41 further includes: a leg plane projection unit 59 for projecting the floor reaction force value calculated by the floor reaction force estimation unit 58, the position vector value of the floor reaction force application point calculated by the floor reaction force application point estimation unit 57, and the acceleration vector and angular velocity vector values calculated by the body coordinate system acceleration and angular velocity calculation unit 54 onto the leg plane PL corresponding to the each leg by using the transformation tensor generated by the transformation tensor generation unit 51; and a joint moment calculation unit 60 for calculating estimated values of the joint moments to be generated at the ankle joint, the knee joint, and the hip joint of the person A by using the values obtained by the projection (two-dimensional quantities) and the locations and the postures calculated by the two-dimensional leg posture and element center-of-gravity location calculation unit 52.

Although the details are described later, the human-side joint moment estimation unit 41 sequentially performs the arithmetic processing of the aforementioned units 51 to 60 each in a predetermined arithmetic processing period and finally calculates the estimated values of the joint moments sequentially by using the joint moment calculation unit 60 in each arithmetic processing period.

On the other hand, as shown in FIG. 8 the orthosis-side joint moment estimation unit 42 includes: a two-dimensional leg posture and element center-of-gravity location calculation unit 61 for calculating positions of the joint elements, the postures (tilt angles) of the rigid elements, and the centers of gravity location of the rigid elements on the XZ plane of the leg coordinate system LC of the each leg S2 of the orthosis rigid link model S1' on the basis of detected outputs of the joint displacement sensors 31, 32, and 33; a three-dimensional joint and element center-of-gravity location calculation unit 62 for calculating three-dimensional position vector values (coordinate component values) on the body coordinate system BC of the centers of gravity of the joint elements and the rigid elements of the orthosis rigid link model S1' by using the positions and the postures calculated by the two-dimensional leg posture and element center-of-gravity location calculation unit 61 and the transformation tensor generated by the transformation tensor generation unit 51 (See *1 in FIG. 7 and FIG. 8) of the human-side joint moment estimation unit 41; and an entire center-of-gravity location calculation unit 63 for calculating a value of the position vector of the entire center of gravity (the entire center of gravity of the support orthosis 1) of the orthosis rigid link model S1' on the body coordinate system BC by using the position vectors of the centers of gravity of the joint elements of the orthosis rigid link model S1' calculated by the three-dimensional joint and element center-of-gravity location calculation unit 62. The position vectors calculated by the three-dimensional joint and element center-of-gravity location calculation unit 62 include position vectors of the bottom edges of the support members S9b, S9c of the each foot element S9 of the orthosis rigid link model S1' (See FIG. 5).

Moreover, the orthosis-side joint moment estimation unit 42 includes: a floor reaction force application point estimation unit 64 for calculating a value on the body coordinate system BC of the position vector of the application point (the floor reaction force application point) of a floor reaction force (a translation floor reaction force) applied to the each leg link portion 4 of the support orthosis 1 by using the position vector values of the support members S9b, S9c of the each foot element S9 of the orthosis rigid link model S1' calculated by the three-dimensional joint and element center-of-gravity location calculation unit 62, the tilt angle of the body coordinate system BC calculated by the body coordinate system tilt angle calculation unit 55 (See *2 in FIG. 7 and FIG. 8) of the human-side joint moment estimation unit 41, the position vector value of the entire center of gravity calculated by the entire center-of-gravity location calculation unit 63, and detected outputs of the landing sensors 34, 35; and a floor reaction force estimation unit 65 for estimating a value on the body coordinate system BC (a coordinate component value) of a floor reaction force (a vector of a translation floor reaction force) applied to the each leg link portion 4 of the support orthosis 1 by using the position vector values of the centers of gravity of the joint elements and the rigid elements of the orthosis rigid link model S1' calculated by the three-dimensional joint and element center-of-gravity location calculation unit 62, the position vector value of the entire center of gravity calculated by the entire center-of-gravity location calculation unit 63, the values of the acceleration vector and the angular velocity vector of the origin of the body coordinate system BC calculated by the body coordinate system acceleration and angular velocity calculation unit 54 (See *3 in FIG. 7 and FIG. 8) of the human-side joint moment estimation unit 41, detected outputs of the landing sensors 34, 35, and the position vector value of the floor reaction force application point calculated by the floor reaction force application point estimation unit 64. The floor reaction force estimated by the floor reaction force estimation unit 65, more specifically, means a floor reaction force applied to the each leg link portion 4 of the support orthosis 1, supposing that the support orthosis 1 is making the motion of the support orthosis 1 following the motion of the legs of the person A independently (by itself).

Furthermore, the orthosis-side joint moment estimation unit 42 includes: a leg plane projection unit 66 for projecting the floor reaction force value estimated by the floor reaction force estimation unit 65, the position vector value of the floor reaction force application point estimated by the floor reaction force application point estimation unit 64, and the values of the acceleration vector and the angular velocity vector calculated by the body coordinate system acceleration and angular velocity calculation unit 54 of the human-side joint moment estimation unit 41 onto the leg plane PL corresponding to the each leg (projecting them onto the XZ plane of the leg coordinate system LC of the orthosis rigid link model S1') by using the transformation tensor generated by the transformation tensor generation unit 51 (See *1 in FIG. 7 and FIG. 8) of the human-side joint moment estimation unit 41; and a joint moment calculation unit 67 for calculating estimated values of joint moments to be generated at the joint regions 7, 9, and 11 of the support orthosis 1 by using the values (two-dimensional quantities) obtained by the projection and the positions and postures calculated by the two-dimensional leg posture and element center-of-gravity location calculation unit 61.

Although the details are described later, the orthosis-side joint moment estimation unit 42 sequentially performs arithmetic processing of the aforementioned units 61 to 67 each in a predetermined arithmetic processing period in parallel with the processing of the human-side joint moment estimation unit 41 and finally calculates the estimated values of the joint moments sequentially by using the joint moment calculation unit 67 in each arithmetic processing period.

Moreover, as shown in FIG. 6, the actual joint support moment estimation unit 44 receives inputs of the floor reaction force on the leg plane PL obtained by the leg plane projection unit 66 (the floor reaction force on the XZ plane of the leg coordinate system LC of the orthosis rigid link model S1'. See *4 in FIG. 6 and FIG. 8) of the orthosis-side joint moment estimation unit 42, the detected outputs of the force sensors 20, 22 and the displacement sensor 21, and the postures of the each leg S2 (the tilt angle on the leg plane PL of the thigh element S7 or the like. See *5 in FIG. 6 and FIG. 8) of the orthosis rigid link model S1' calculated by the two-dimensional leg posture and element center-of-gravity location calculation unit 61 of the orthosis-side joint moment estimation unit 42. Then, the actual joint support moment estimation unit 44 calculates actual joint support moment estimated values as described below by using these input values.

The following describes the operation of the apparatus of this embodiment in conjunction with the detailed arithmetic processing of the respective units of the arithmetic processing unit 25. In the following description, generally the transformation tensor for coordinate-converting a vector quantity from a certain coordinate system Ca to another coordinate system Cb, namely a tensor for converting a vector quantity represented by a component value of the coordinate system Ca to a vector quantity represented by a component value of the coordinate system Cb is denoted by R(Ca→Cb) Furthermore, a position vector of a point P or a region P viewed on the coordinate system Ca is denoted by U(P/Ca). Still further, a vector A of an applied force, an acceleration, or other physical quantity of an object Q or a region Q, which is represented by a coordinate component value of the coordinate system Ca is denoted by A(Q/Ca). In this case, when representing a coordinate component value on the coordinate system Ca of the position vector U(P/Ca) or the physical quantity vector A(Q/Ca), the name of each coordinate axis x, y, or z is added in the denotation. For example, the X coordinate component of the position vector U(P/Ca) is denoted by U(P/Ca)x. Furthermore, when representing a pair of two coordinate component values (two-dimensional vector) on the coordinate system Ca of the position vector U(P/Ca) or the physical quantity vector A(Q/Ca), the names of the two coordinate axes are added in the denotation. For example, a two-dimensional vector made of a pair of an X-axis component and a Z-axis component of the vector A(Q/Ca) (a component vector on the plane perpendicular to the Y axis (the Y axis of the coordinate system Ca) of the vector A(Q/Ca)) is denoted by A(Q/Ca)x,z. If the coordinate system focused on is obvious, the denotation of the coordinate system Ca may be omitted in some cases.

Moreover, the element coordinate systems C4 to C9 are sometimes referred to as C_waist, C_abdomen, C_chest, C_thigh, C_crus, and C_foot by using the names of the regions of the person A corresponding to C4 to C9, respectively. It is assumed that the same applies to the rigid elements S4 to S9 of the human rigid link model S1 and the centers of gravity G4 to G9 of the rigid elements S4 to S9. For example, the waist element S4 of the human rigid link model S1 and its center of gravity G4 are sometimes denoted by S_waist and G_waist, respectively.

Furthermore, the rigid elements S4 to S9 of the orthosis rigid link model S1' are sometimes referred to as S_waist orthosis, S_abdomen orthosis, S_chest orthosis S_thigh orthosis, S_crus orthosis, and S_foot orthosis, respectively, by using the names of the corresponding regions of the person A. It is assumed that the same applies to the centers of gravity of the rigid elements S4 to S9 of the orthosis rigid link model S1'. For example, the center of gravity G4 of the waist element S4 of the orthosis rigid link model S1' is sometimes denoted by G_waist orthosis.

Regarding denotations related to the leg of the person A or related to the leg link portion 4 of the support orthosis 1, "right" or "left" is added in the denotation if the difference between right and left need be indicated. For example, the right thigh element S7 is sometimes referred to as an S_right thigh or S_right thigh orthosis.

Moreover, the hip joint J1, the knee joint J2, the ankle joint J3, and the MP joint J4 of the human rigid link model S1 are sometimes referred to as J_hip, J_knee, J_ankle, and J_MP, respectively, and the hip joint J1, the knee joint J2, and the ankle joint J3 of the orthosis rigid link model S1' are sometimes referred to as J_hip orthosis, J_knee orthosis, and J_ankle orthosis, respectively. If there is a need for indicating the difference between right and left, the term "right" or "left" is added in the denotation similarly to the above.

The arithmetic processing unit 25 accepts detected outputs of the joint displacement sensors 31, 32, and 33, the light emitter/receiver 28, the acceleration sensor 23, the gyro sensor 24, the force sensors 20, 22, and the displacement sensor 21 via an A/D converter, not shown, and accepts detected outputs (ON/OFF signals) of the landing sensors 34, 35 each in a predetermined arithmetic processing period. It then performs the arithmetic processing of the human-side joint moment estimation unit 41 and the orthosis-side joint moment estimation unit 42 in parallel, first.

The arithmetic processing of the human-side joint moment estimation unit 41 is described in detail below. It should be noted here that the rigid element, the joint element, the leg coordinate system, and the element coordinate system are assumed to mean the rigid element, the joint element, the leg coordinate system, and the element coordinate system of the human rigid link model S1, respectively, unless otherwise specified, hereinafter until the description of the human joint moment estimation unit 41 is completed.

First, the arithmetic processing operations of the transformation tensor generation unit 51, the two-dimensional leg posture and element center-of-gravity location calculation unit 52, and the three-dimensional joint and element center-of-gravity location calculation unit 53 are sequentially performed.

The arithmetic processing of the transformation tensor generation unit 51 includes generating a transformation tensor R(LC→BC) for performing a coordinate transformation of a vector quantity between the each leg coordinate system LC and the body coordinate system BC and transformation tensors R(C_abdomen→BC) and R(C_chest→BC) for performing a coordinate transformation of a vector quantity between the each of the element coordinate system C5 of the abdomen element S5 and the element coordinate system C6 of the chest element S6 and the body coordinate system BC.

The transformation tensor R(LC→BC) is determined from rotation angles around two axes except the rotation angle around a rotation axis a31 perpendicular to the leg plane PL among the rotation angles around three axes of the hip joint region 7 detected by the joint displacement sensor 31 of the hip joint region 7 of the support orthosis 1. In this embodiment, if the rotation angles of the hip joint region 7 around two axes except the rotation axis a31 perpendicular to the leg plane PL (rotation angles of the hip joint region 7 accompanying an outward or inward swing and slewing around the hip joint of the leg of the person A) are determined, the posture relationship between the leg coordinate system LC and the body coordinate system BC of the human rigid link model S1 is integrally determined. Therefore, the transformation tensor R(LC→BC) can be obtained from the detected values of the rotation angles around two axes except the rotation angle around the rotation axis a31 perpendicular to the leg plane PL out of the rotation angles around three axes of the hip joint. Incidentally, the transformation tensor R(LC→BC) is obtained for each of the right and left legs.

The transformation tensors R(C_abdomen→BC) and the R(C_chest→BC) are generated as described below. First, tilt angles of the abdomen element S5 and the chest element S6 relative to the waist element S4 of the human rigid link model S1 (more specifically, the tilt angles on the sagittal plane (XZ plane) relative to the Z axis direction of the body coordinate system BC) are grasped based on the detected outputs of the light emitter/receiver 28. Then, the transformation tensor R(C_abdomen→BC) is determined as one having the coordinate system C_abdomen tilting on the sagittal plane relative to the body coordinate system BC by the tilt angle of the abdomen element S5 relative to the waist element S4. Similarly, the transformation tensor R(C_abdomen→BC) is determined as one having the coordinate system C_chest tilting on the sagittal plane relative to the body coordinate system BC by the tilt angle of the chest element S6 relative to the waist element S4.

As supplementary information, although measurement has been made only for the tilt angles relative to the waist element S4 of the abdomen element S5 and the chest element S6 caused by the rotation around a single axis (around the Y axis of the C_abdomen and C_chest) of the lower joint of the upper body JU1 and the upper joint of the upper body JU2 of the human rigid link model S1 in this embodiment, it is also possible to measure tilt angles around two axes of the abdomen element S5 and the chest element S6, supposing that the lower joint of the upper body JU1 and the upper joint of the upper body JU2 can rotate around two axes, for example (for example, around two axes of the Y axis and the X axis of the C_abdomen and the C_chest). Then, the transformation tensors R(C_abdomen→BC) and R(C_chest→BC) may be calculated based on the tilt angles around the two axes.

Incidentally, the transpositions of the aforementioned transformation tensors R(LC→BC), R(C_abdomen→BC), and R(C_chest→BC) are transformation tensors for performing inverse transformations therefor. Therefore, R(BC→LC)=R(LC→BC)$^T$, R(BC→C_abdomen)=R(C_abdomen→BC)$^T$, R(BC→C_chest)=R(C_chest→BC)$^T$ (T designates a transposition).

In the arithmetic processing of the two-dimensional leg posture and element center-of-gravity location calculation unit 52, first, tilt angles θ_thigh, θ_crus, and θ_foot of the thigh element S7, the crus element S8, and the foot element S9 of the human rigid link model S1 are respectively calculated by using rotation angles around axes (rotation axes a31, a32, and a33 in FIG. 2) perpendicular to the leg plane PL of the hip joint region 7, the knee joint region 9, and the ankle joint region 11 of the leg link portion 4, which are grasped from the detected outputs of the joint displacement sensors 31 to 33 of the each leg link portion 4 of the support orthosis 1. Note here that the tilt angles θ_thigh, θ_crus, and θ_foot are those relative to the Z axis direction of the leg coordinate system LC.

In this instance, for example, if the position of the knee joint region 9 of the each leg link portion 4 deviates from the lateral place (just beside) of the knee joint of the person A (in this case, the length of the thigh of the person A is not coincident with the length of the thigh link member 8 of the support orthosis 1, or the length of the crus of the person A is not coincident with the length of the crus link member 10 of the support orthosis 1), the rotation angles around the axis perpendicular to the leg plane PL of the hip joint region 7, the knee joint region 9, and the ankle joint region 11 of the each leg link portion 4 differ from the rotation angles around the axis perpendicular to the leg plane PL of the hip joint, the knee joint, and the ankle joint of the person A in general.

Figure 9:
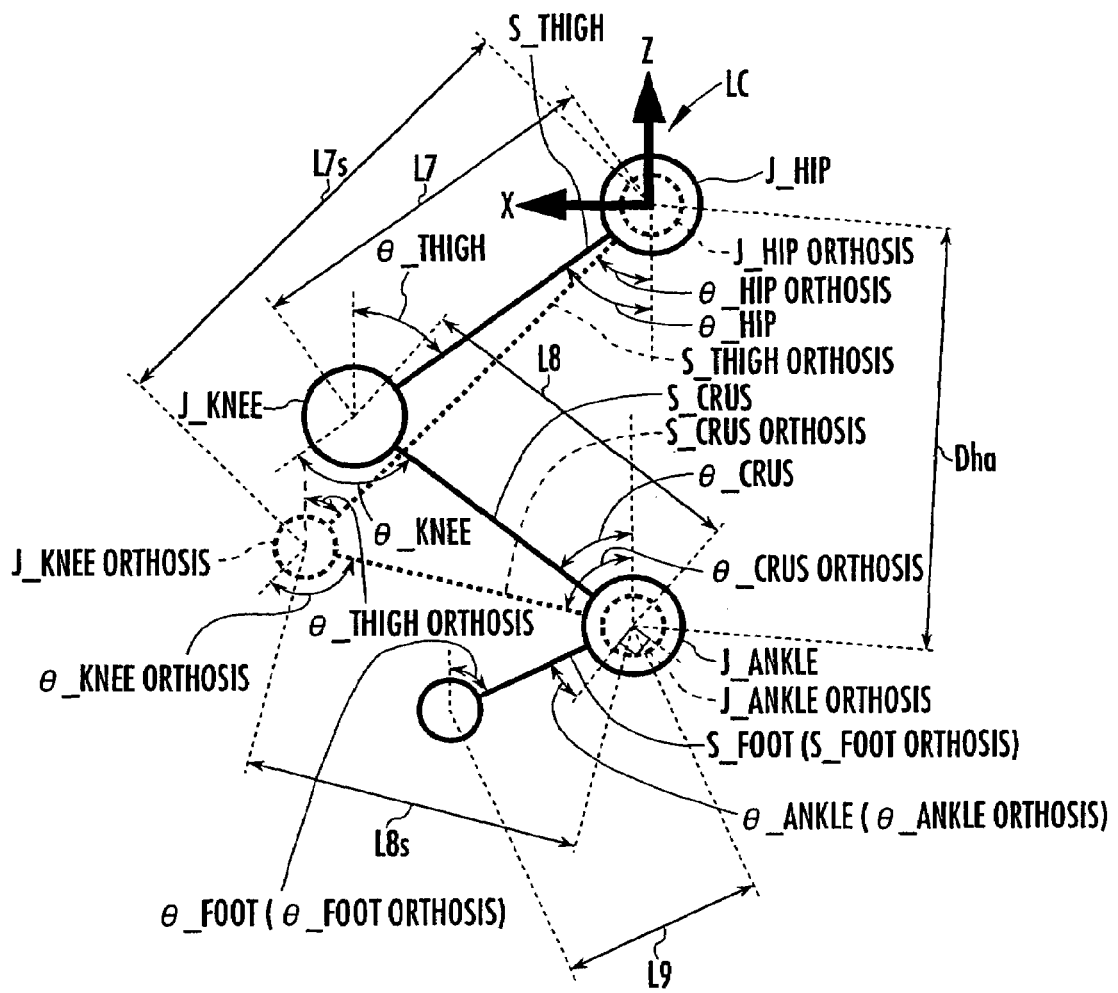
FIG. 9 is a diagram for explaining elements of a person's leg and processing for finding a position and a posture of a leg link portion of the leg motion support orthosis on the leg plane.

Accordingly, in this embodiment, the rotation angles around the axis perpendicular to the leg plane PL of the hip joint, the knee joint, and the ankle joint of the person A (the rotation angles around the axis perpendicular to the leg plane PL of the joint J_hip (J1), J_knee (J2), and J_ankle (J3) of the each leg S2 of the human rigid lnk model S1) are obtained by a geometric operation on the basis of the detected values of the rotation angles around the axis perpendicular to the leg plane PL of the hip joint region 7, the knee joint region 9, and the ankle joint region 11 of the each leg link portion 4, and then the tilt angles θ_thigh, θ_crus, θ_foot are calculated on the basis of the obtained rotation angles. The calculation method is described hereinafter by referring to FIG. 9. FIG. 9 shows a geometric relation in the leg S2 between the human rigid link model S1 and the orthosis rigid link model S1' viewed on the leg plane PL. The elements of the leg S2 of the orthosis rigid link model S1' are indicated by dashed lines.

In FIG. 9, θ_hip orthosis, θ_knee orthosis, and θ_ankle orthosis are rotation angles (rotation angles from the aforementioned reference posture condition of the support orthosis 1) of the hip joint region 7, the knee joint region 9, and the ankle joint region 11 of the support orthosis 1 detected by the joint displacement sensors 31, 32, and 33, respectively. In this embodiment, the hip joint region 7 and the ankle joint region 11 are disposed in the lateral places (just beside) of the hip joint and the ankle joint of the person A, respectively, and therefore the position of J_hip of the human rigid link model S1 viewed on the leg plane PL is coincident with the position of J_hip orthosis of the orthosis rigid link model S1' and the position of J_ankle is coincident with the position of J_ankle orthosis. Moreover, the rotation angle θ_ankle orthosis of the ankle joint region 11 of the support orthosis 1 detected by the joint displacement sensor 33 is coincident with the rotation angle θ_ankle of the ankle joint of the person A. In this embodiment, θ_hip orthosis, θ_knee orthosis, and θ_ankle orthosis detected when the person A wearing the support orthosis 1 squats down from the reference posture condition are assumed to be positive values. Accordingly, in the shown example, θ_hip orthosis>0, θ_knee orthosis>0, and θ_ankle orthosis>0. Moreover, in this embodiment, tilt angle θ_thigh of the S_thigh (the thigh element S7) is assumed to be a negative value when the J_knee of the human rigid link model S1 is located on the positive side (the forward side) of the X axis of the leg coordinate system LC relative to the J_hip, tilt angle θ_crus of the S_crus (the crus element S8) is assumed to be a negative value when the J_ankle is located on the positive side of the X axis of the leg coordinate system LC relative to the J_knee, and tilt angle θ_foot of the S_foot (the foot element S9) is assumed to be a negative value when the J_MP (the tow of the foot element S9) is located on the positive side of the X axis of the leg coordinate system LC relative to the J_ankle. In the shown example, θ_thigh<0, θ_crus>0, and θ_foot<0. The same applies to the tilt angle θ_thigh orthosis, the θ_crus orthosis, and the θ_foot orthosis of the S_thigh orthosis, the S_crus orthosis, and the S_foot orthosis of the orthosis rigid link model S1', respectively.

In this instance, the rotation angles θ_knee and the θ_hip of the J_knee and the J_hip of the human rigid link model S1 are calculated by the following formulas (1a) and (1b) in order:

$$\theta\_knee = \pi - \cos^{-1}((L7^2 + L8^2 - Dha^2)/(2 \times L7 \times L8)) \quad (1a)$$

$$\theta\_hip = \theta\_hip\ orthosis - \sin^{-1}((L8s^2/Dha) \times \sin(\pi - \theta\_knee\ orthosis)) + \sin^{-1}((L8/Dha) \times \sin(\pi - \theta\_knee)) \quad (1b)$$

In the above, L7 and L8 are the lengths of the S_thigh and S_crus of the human rigid link model S1, respectively, and L8s is the length of the S_crus of the orthosis rigid link model S1'. Moreover, Dha is a distance between the J_hip and the J_ankle of the human rigid link model S1 (the distance equals the distance between the J_hip orthosis and the J_ankle orthosis of the orthosis rigid link model S1'), and it is calculated by the following formula (1c):

$$Dha = \sqrt{(L7s^2 + L8s^2 - 2 \times L7s \times L8s \times \cos(\pi - \theta\_knee\ orthosis))} \quad (1c)$$

In the above, L7s is the length of the S_thigh of the orthosis rigid link model S1'.

Then, the tilt angles θ_thigh, θ_crus, and θ_foot are found from the detected values of the θ_knee, the θ_hip, and the θ_ankle (=the detected value of the θ_ankle orthosis), which are obtained using the detected values of the θ_knee orthosis and the θ_hip orthosis by the above formulas (1a) to (1c), respectively, by using the following formulas (1d) to (1f):

$$\theta\_thigh = -\theta\_hip \quad (1d)$$

$$\theta\_crus = \theta\_thigh + \theta\_knee \quad (1e)$$

$$\theta\_foot = \theta\_crus - \theta\_ankle + (\pi/2) \quad (1f)$$

The θ_thigh, θ_crus, and θ_foot are calculated for each of the legs S2 individually.

The tilt angles θ_thigh, θ_crus, and θ_foot calculated as described above represent the postures on the leg plane PL (the XZ plane of the leg coordinate system LC) corresponding to the each leg S2 of the rigid elements thereof of the human rigid link model S1.

Subsequently, the positions of the joint elements of the each leg S2 on the XZ plane of the leg coordinate system LC or the leg plane PL are obtained by using the θ_thigh, θ_crus, and θ_foot obtained as described above and the lengths of the rigid elements of the each leg S2 of the human rigid link model S1. Specifically, position vectors U(J_hip/LC), U(J_knee/LC), U(J_ankle/LC), and U(J_MP/LC) on the leg coordinate system LC of the joint elements J_hip (J1), J_knee (J2), J_ankle (J3), and J_MP (J4) of the each leg S2 are calculated in order by using the formulas (2a) to (2d) below. In this calculation, all of the positions of the J_hip, the J_knee, the J_ankle, and the J_MP in the Y-axis direction of the leg coordinate system LC (the normal line direction on the leg plane PL), in other words, the Y-axis components of the position vector U(J_hip/LC), U(J_knee/LC), U(J_ankle/LC), and U(J_MP/LC) are assumed to be zero. Thus, in this embodiment, it is assumed that all of the J_hip, the J_knee, the J_ankle, and the J_MP are movable only on the leg plane PL.

$$U(J\_hip/LC) = (0, 0, 0)^T \quad (2a)$$

$$U(J\_knee/LC) = U(J\_hip/LC) + (-L7 \times \sin(\theta\_thigh), 0, -L7 \times \cos(\theta\_thigh))^T \quad (2b)$$

$$U(J\_ankle/LC) = U(J\_knee/LC) + (-L8 \times \sin(\theta\_crus), 0, -L8 \times \cos(\theta\_crus))^T \quad (2c)$$

$$U(J\_MP/LC) = U(J\_ankle/LC) + (-L9 \times \sin(\theta\_foot), 0, -L9 \times \cos(\theta\_foot))^T \quad (2d)$$

In the above, L7, L8, and L9 in the formulas (2b), (2c), and (2d) are the lengths of the S_thigh (the thigh element S7), the S_crus (the crus element S8), and the S_foot (the foot element S9). The vectors of the second term in the right-hand side of the formulas (2b) to (2d) respectively mean the position vector of the knee joint J2 (J_knee) viewed from the hip joint J1 (J_hip), the position vector of the ankle joint J3 (J_ankle) viewed from the knee joint J2, and the position vector of the MP joint J4 (J_MP) viewed from the ankle joint J3, respectively. In this regard, a pair of an X-axis component and a Z-axis component of each of the position vectors U(J_hip/LC), U(J_knee/LC), U(J_ankle/LC), and U(J_MP/LC) calculated by the formulas (2a) to (2d) represents a two-dimensional position on the leg plane PL.

Moreover, the position vectors on the leg coordinate system LC of the centers of gravity of the rigid elements of the each leg S2 are calculated by using the position vectors of the joint elements calculated as described above by the formulas (2a) to (2d). More specifically, position vectors U(G_thigh/LC), U(G_crus/LC), U(G_foot/LC) of the centers of gravity G_thigh (G7), G_crus (G8), and G_foot (G9) of the thigh element S7, the crus element S8, and the foot element S9 of the each leg S2 are respectively calculated by the following formulas (3a) to (3c):

$$U(G\_thigh/LC) = U(J\_knee/LC) + R(C\_thigh \rightarrow LC) \times U(G\_thigh/C\_thigh) \quad (3a)$$

$$U(G\_crus/LC) = U(J\_ankle/LC) + R(C\_crus \rightarrow LC) \times U(G\_crus/C\_crus) \quad (3b)$$

$$U(G\_foot/LC) = U(J\_MP/LC) + R(C\_foot \rightarrow LC) \times U(G\_foot/C\_foot) \quad (3c)$$

In the formulas (3a) to (3c), R(C_thigh→LC), R(C_crus→LC), and R(C_foot→LC) are respectively a transformation tensor from the thigh coordinate system C_thigh (C7) to the leg coordinate system LC, a transformation tensor from the crus coordinate system C_crus (C8) to the leg coordinate system LC, and a transformation tensor from the foot coordinate system C_foot (C9) to the leg coordinate system LC and they are determined by using the previously calculated θ_thigh, θ_crus, and θ_foot. In addition, U(G_thigh/C_thigh), U(G_crus/C_crus), and U(G_foot/C_foot) are position vectors of the centers of gravity of the rigid elements represented on the element coordinate system of the corresponding rigid elements, and they are previously stored in the memory of the arithmetic processing unit 25.

A pair of the X-axis component and the Z-axis component of each of the position vectors U(G_thigh/LC), U(G_crus/LC), and U(G_foot/LC) calculated by the above formulas (3a) to (3c) represents a two-dimensional position on the leg plane PL. The above is the arithmetic processing of the two-dimensional leg posture and element center-of-gravity location calculation unit 52.

Subsequently, in the arithmetic processing of the three-dimensional joint and element center-of-gravity location calculation unit 53, the position vectors on the body coordinate system BC of the joint elements and the centers of gravity of the rigid elements of the human rigid link model S1 are calculated by using the transformation tensor obtained by the transformation tensor generation unit 51 and the positions of the joint elements and the centers of gravity of the rigid elements of the each leg S2 obtained by the two-dimensional leg posture and element center-of-gravity location calculation unit 52.

The position vectors of the joint elements are calculated as described below. The following describes the calculation of the position vectors of the joint elements (including the MP joint J4) of the left leg S2, for example. First, supposing that L4a is the length of the line segment between the centers of the both hip joint J1, J1 of the waist element S4, the position vector U(J_left hip/BC) of the left hip joint J1 on the body coordinate system BC is given by the following formula (4a):

$$U(J\_left\ hip/BC)=(0, L4a/2, 0)^T \quad (4a)$$

Furthermore, position vectors U(J_left knee/BC), U(J_left ankle/BC), and U(J_left MP/BC) of the left knee joint J2, the left ankle joint J3, and the left MP joint J4 on the body coordinate system BC are found in order by the following formulas (4b) to (4d), using the transformation tensor R(LC→BC) and the position vectors U(J_left knee/LC), U(J_left ankle/LC), and U(J_left MP/LC) on the leg coordinate system LC (left LC) corresponding to the left leg S2:

$$U(J\_left\ knee/BC)=U(J\_left\ hip/BC)+R(LC{\rightarrow}BC){\times}U(J\_left\ knee/LC) \quad (4b)$$

$$U(J\_left\ ankle/BC)=U(J\_left\ hip/BC)+R(LC{\rightarrow}BC){\times}U(J\_left\ ankle/LC) \quad (4c)$$

$$U(J\_left\ MP/BC)=U(J\_left\ hip/BC)+R(LC{\rightarrow}BC){\times}U(J\_left\ MP/LC) \quad (4d)$$

The position vectors on the body coordinate system BC of the joint elements (including the MP joint J4) of the right leg S2 can be found in the same manner as for the above.

Moreover, position vectors U(JU1/BC) and U(JU2/BC) on the body coordinate system BC of the lower joint of the upper body JU1 and the upper joint of the upper body JU2 of the upper body S3 are calculated in order by using the following formulas (4e) and (4f):

$$U(JU1/BC)=(0, 0, L4b)^T \quad (4e)$$

$$U(JU2/BC)=U(JU1/BC)+R(C\_abdomen{\rightarrow}BC){\cdot}(0, 0, L5)^T \quad (4e)$$

In the above, L4b in the formula (4e) is the length from the midpoint of the line segment between the both hip joints J1, J1 to the center of the lower joint of the upper body JU1, and L5 in the formula (4f) is the length of the abdomen element S5.

The position vectors on the body coordinate system BC of the centers of gravity of the rigid elements are calculated as described below. Specifically, the position vector U(G_thigh/BC), U(G_crus/BC), or U(G_foot/BC) on the body coordinate system BC of the center of gravity of the thigh element S7, the crus element S8, or the foot element S9 is found by calculating the formula in which U(J_left knee/LC) in the right-side hand of the formula (4b) is replaced with the position vector U(G_thith/LC), U(G_crus/LC), or U(G_foot/LC) of the center of gravity of the thigh element S7, the crus element S8, or the foot element S9 calculated by the two-dimensional leg posture and element center-of-gravity position calculation unit 52. The position vectors on the body coordinate system BC of the G_thigh, G_crus, and G_foot are calculated for each of the legs S2 individually.

In addition, a position vector U(G_waist/BC) of the center of gravity G4 of the waist element S4 is found from the position vector U(G_waist/C_waist) of the center of gravity G_waist on the previously-stored waist coordinate system C_waist (C4) by the following formula (4g):

$$U(G\_waist/BC)=R(C\_waist{\rightarrow}BC){\times}U(G\_waist/C\_waist) \quad (4g)$$

where R(C_waist→BC) is a transformation tensor from the waist coordinate system C_waist to the body coordinate system BC. In this embodiment, the C_waist is equivalent to the body coordinate system BC and therefore R(C_waist→BC) is represented by an identity matrix of order 3. Therefore, U(G_waist/C_waist) is obtained directly as U(G_waist/BC).

Moreover, the position vectors U(G_abdomen/BC) and U(G_chest/BC) on the body coordinate BC of the centers of gravity G5 and G6 of the abdomen element S5 and the chest element S6 are found by the following formulas (4h) and (4i), using the transformation tensor R(C_abdomen→BC) and R(C_chest→BC) obtained by the transformation tensor generation unit 51, the position vector U(G_abdomen/C_abdomen) of the center of gravity of the abdomen element S5 on the previously-stored abdomen coordinate system C_abdomen (C5), and the position vector U(G_chest/C_chest) of the center of gravity of the chest element S6 on the chest coordinate system C_chest (C6):

$$U(G\_abdomen/BC)=U(JU1/BC)+R(C\_abdomen{\rightarrow}BC){\cdot}U(G\_abdomen/C\_abdomen) \quad (4h)$$

$$U(G\_chest/BC)=U(JU2/BC)+R(C\_chest{\rightarrow}BC){\cdot}U(G\_chest/C\_chest) \quad (4i)$$

Incidentally, U(JU1/BC) and U(JU2/BC) have been found by the aforementioned formulas (4e) and (4f).

The above is the arithmetic processing of the three-dimensional joint and element center-of-gravity location calculation unit 53. The position vectors of the joint elements and those of the centers of gravity of the rigid elements calculated by the three-dimensional joint and element center-of-gravity location calculation unit 53 mean position vectors viewed on the body coordinate system BC of the actual regions of the person A corresponding to them.

The human-side joint moment estimation unit 41 performs the arithmetic processing of the body coordinate system acceleration and angular velocity calculation unit 54 and the body coordinate system tilt angle calculation unit 55 in parallel with the arithmetic processing of the transformation tensor generation unit 51, the two-dimensional leg posture and element center-of-gravity location calculation unit 52, and the three-dimensional joint and element center-of-gravity location calculation unit 53.

In the arithmetic processing of the body coordinate system acceleration and angular velocity calculation unit 54, a value on the body coordinate system BC (coordinate component value) of the acceleration vector of the origin of the body coordinate system BC is found as described below from the 3-axis acceleration (translation acceleration) grasped from detected outputs of the acceleration sensor 23 and the 3-axis angular velocity grasped from detected outputs of the gyro sensor 24. First, the acceleration and the angular velocity respectively detected by the sensors 23 and 24 are vector quantities represented by the 3-axis coordinate system fixed to the sensors 23 and 24 (hereinafter, referred to as the sensor coordinate system SC or C_sensor) and therefore they are transformed into a value on the body coordinate system BC. The transformation is performed by multiplying the acceleration vector and the angular velocity vector detected on the sensor coordinate system SC by a transformation tensor preset according to the relative attachment positional relationship (the relative posture relationship of the C_sensor to C4 (=BC)) of the acceleration sensor 23 and the gyro sensor (angular velocity sensor) 24 to the waist of the person A. In other words, supposing that a detected value of the acceleration vector on the sensor coordinate system SC is ACC (sensor/SC), an acceleration vector obtained by transforming it into the body coordinate system BC is ACC(sensor/BC), a detected value of the angular velocity vector on the sensor coordinate system SC is ω(sensor/SC), and an angular velocity vector obtained by transforming it into the body coordinate system BC is ω(sensor/BC), the acceleration vector ACC (sensor/BC) and the angular velocity vector ω(sensor/BC) are found by the formulas (5a) and (5b) described below. In this regard, ACC(sensor/BC) and ω(sensor/BC) are more specifically an acceleration vector and an angular velocity vector at the places of the acceleration sensor 23 and the gyro sensor 24. In this example, the places of the acceleration sensor 23 and the gyro sensor 24 are substantially coincident with each other and the sensor coordinate system SC is the same for the both sensors 23 and 24.

$$ACC(sensor/BC)=R(SC \rightarrow BC) \cdot ACC(sensor/SC) \quad (5a)$$

$$\omega(sensor/BC)=R(SC \rightarrow BC) \cdot \omega(sensor/SC) \quad (5b)$$

In the above, the transformation tensor R(SC→BC) is determined from the relative posture relationship between the sensor coordinate SC and the body coordinate system BC (more specifically, the tilt angle of each axis of the sensor coordinate system SC to each axis of the body coordinate system BC) and it is previously stored in the memory of the arithmetic processing unit 25 when the support orthosis 1 is put on the person A or the like. As supplementary information, the acceleration sensor 23 or the gyro sensor 24 may be attached to the region other than the waist of the person A (a rigid equivalent part corresponding to one of the rigid elements of the human rigid link model S1). In this instance, to acquire the acceleration vector ACC(sensor/BC) or the angular velocity vector ω(sensor/BC), the detected value on the sensor coordinate system SC is transformed to a value on the element coordinate system of the rigid element to which the acceleration sensor 23 or the gyro sensor 24 is attached, and then it is transformed to a value on the body coordinate system BC by using the transformation tensor. The transformation tensor in this instance is determined based on a displacement (rotation angle) of the joint element between the rigid element to which the acceleration sensor 23 or the gyro sensor 24 is attached and the waist element S4.

In the arithmetic processing of the body coordinate system acceleration and the angular velocity calculation unit 54, the acceleration vector ACC(sensor/BC) and the angular velocity vector ω(sensor/BC) are found as described above and thereafter an acceleration vector ACC(BCO/BC) of the origin of the body coordinate system BC is found by the formula (5c) below. The symbol "BCO" represents the origin of the body coordinate system BC.

$$ACC(BCO/BC) = \quad (5c)$$
$$ACC(sensor/BC) + U(sensor/BC) \times \omega(sensor/BC)' +$$
$$\begin{bmatrix} 0 & U(sensor/BC)x & U(sensor/BC)x \\ U(sensor/BC)y & 0 & U(sensor/BC)y \\ U(sensor/BC)z & U(sensor/BC)z & 0 \end{bmatrix} \times$$
$$\begin{bmatrix} \omega(sensor/BC)x^2 \\ \omega(sensor/BC)y^2 \\ \omega(sensor/BC)z^2 \end{bmatrix}$$

In the formula (5c), U(sensor/BC) is a position vector of the acceleration sensor 23 and the gyro sensor 24 on the body coordinate system BC and U(sensor/BC)x, U(sensor/BC)y, and U(sensor/BC)z are coordinate component values on the body coordinate system BC of U(sensor/BC) according to the aforementioned definition of the notation method of a coordinate component value of a vector in this specification. U(sensor/BC) is measured when the support orthosis 1 is put on the person A and stored in the memory of the arithmetic processing unit 25. In addition, ω(sensor/BC)x, ω(sensor/BC)y, and ω(sensor/BC)z are coordinate component values of the angular velocity vector ω(sensor/BC) previously obtained. Furthermore, ω(sensor/BC)' indicates a first derivative of ω(sensor/BC) and the value is calculated from time series data of ω(sensor/BC) found by the aforementioned formula (5b) for each arithmetic processing period of the arithmetic processing unit 25.

Moreover, the angular velocity is identical in any portion within the waist element S4, and the angular velocity ω(BCO/BC) of the origin BCO of the body coordinate system BC fixed to the waist element S4 is equal to ω(sensor/BC). Therefore, ω(BCO/BC)=ω(sensor/BC).

ACC(BCO/BC) found by the aforementioned formula (5c) is a vector equal to an output value of the acceleration sensor 23 (acceleration detected value) under the condition where the acceleration sensor 23 is set at the origin of the body coordinate system BC and the direction of the axis of the acceleration sensor 23 is matched with the body coordinate system BC.

Since the acceleration sensor 23 also detects an acceleration accompanying the gravity, the acceleration vector ACC (BCO/BC) obtained as described above includes an inertial acceleration component caused by the gravity (gravitational acceleration component). Moreover, while the acceleration vector ACC(BCO/BC) of the origin BCO of the body coordinate system BC has been found in consideration of the angular speed of the waist element S4 in this embodiment, the angular speed of the waist element S4 and its rate of change are relatively low and therefore ACC(sensor/BC), which has been found by the aforementioned formula (5a), may be an acceleration vector ACC(BCO/BC) of the origin BCO of the body coordinate system BC directly.

In the arithmetic processing of the body coordinate system tilt angle calculation unit 55, a tilt angle of the waist element S4 (a tilt angle of the Z axis of the body coordinate system BC) relative to the vertical direction (the direction of gravitational force) is calculated by using the so-called Kalman filter from detected outputs of the acceleration sensor 23 and the gyro sensor 24. The calculation method is already known and therefore its description is omitted here. The tilt angle calculated here is around two axes, namely, the horizontal axis in the forward/backward direction and the horizontal axis in the right/left direction.

Subsequently, the human-side joint moment estimation unit 41 performs the arithmetic processing of the entire center-of-gravity location calculation unit 56. In the arithmetic processing of the entire center-of-gravity location calculation unit 56, a position vector U(G_entire/BC) on the body coordinate system BC of the entire center of gravity of the human rigid link model S1 (the entire center of gravity, hereinafter referred to as G_entire in some cases) is found by the following formula (6), from the centers of gravity location of the rigid elements (the position vectors on the body coordinate system BC) found by the three-dimensional joint and element center-of-gravity location calculation unit 53 and the weights of the rigid elements set as described above:

$$U(\text{G\_entire}/BC) = \qquad (6)$$
$$\{U(\text{G\_chest}/BC) \times \text{m\_chest} + U(\text{G\_abdomen}/BC) \times \text{m\_abdomen} +$$
$$U(\text{G\_waist}/BC) \times \text{m\_waist} + U(\text{G\_right thigh}/BC) \times$$
$$\text{m\_right thigh} + U(\text{G\_left thigh}/BC) \times \text{m\_left thigh} +$$
$$U(\text{G\_right crus}/BC) \times \text{m\_right crus} + U(\text{G\_left crus}/BC) \times$$
$$\text{m\_left crus} + U(\text{G\_right foot}/BC) \times \text{m\_right foot} +$$
$$U(\text{G\_left foot}/BC) \times \text{left foot}\}\text{entire weight}$$

The term "m_☐☐" such as m_chest is a weight of a rigid element of the human rigid link model S1 corresponding to the name of ☐☐ and thus the weight does not include the weight of the support orthosis 1. As shown by the formula (6), the position vector of the entire center of gravity U(G_entire/BC) is found by dividing the total sum of the products of the position vector on the body coordinate system BC of the center of gravity of the each rigid element of the human rigid link model S1 and the weight of the corresponding rigid element by the entire weight of the person A (more specifically, the entire weight of the person A with the support orthosis 1 removed from the person A, which is equal to the total sum of the weights of all the rigid elements of the human rigid link model S1).

Subsequently, the human-side joint moment estimation unit 41 performs calculations of the floor reaction force application point estimation unit 57 and the floor reaction force estimation unit 58.

In the arithmetic processing of the floor reaction force application point estimation unit 57, first, a transformation tensor R(BC→IC) from the body coordinate system BC to an absolute coordinate system IC is generated on the basis of the tilt angle relative to the vertical direction of the waist element S4 calculated by the body coordinate system tilt angle calculation unit 55. In this regard, the absolute coordinate system IC is a rectangular coordinate system whose Z axis is in the vertical direction and whose directions of the coordinate axes are coincident with those of the body coordinate system BC in the reference posture condition of the person A. The transformation tensor R(IC→BC) from the absolute coordinate system IC to the body coordinate system BC is a transposition R(BC→IC)$^t$ of the transformation tensor R(BC→IC). In the case of making a leg motion that causes the tilt angle relative to the vertical direction of the waist element S4 to be substantially constant, the transformation tensor R(BC→IC) is almost fixed. Therefore, it may be previously stored in the memory of the arithmetic processing unit 25.

Subsequently, using the above transformation tensor R(BC→IC), position vectors U(G_entire/IC), U(J_ankle/IC), and U(J_MP/IC) viewed on the absolute coordinate systems IC of the entire center of gravity G_entire, the each ankle joint J3, and the MP joint J4 are calculated by multiplying the position vector U(G_entire/BC) of the entire center of gravity G_entire previously determined by the entire center-of-gravity location calculation unit 56 and the position vectors U(J_ankle/BC) and U(J_MP/BC) of the ankle joint J3 and the MP joint J4 of the each leg S2 previously determined by the three-dimensional joint and element center-of-gravity location calculation unit 53 each by the tensor R(BC→IC). These position vectors U(G_entire/IC), U(J_ankle/IC), and U(J_MP/IC) are position vectors on the absolute coordinate system IC having the same origin as for the body coordinate system BC. At this point, regarding the leg determined to be not in contact with the ground from the detected outputs of the landing sensors 34 and 35, the position vectors U(J_ankle/IC) and U(J_MP/IC) need not be calculated.

Figure 10:
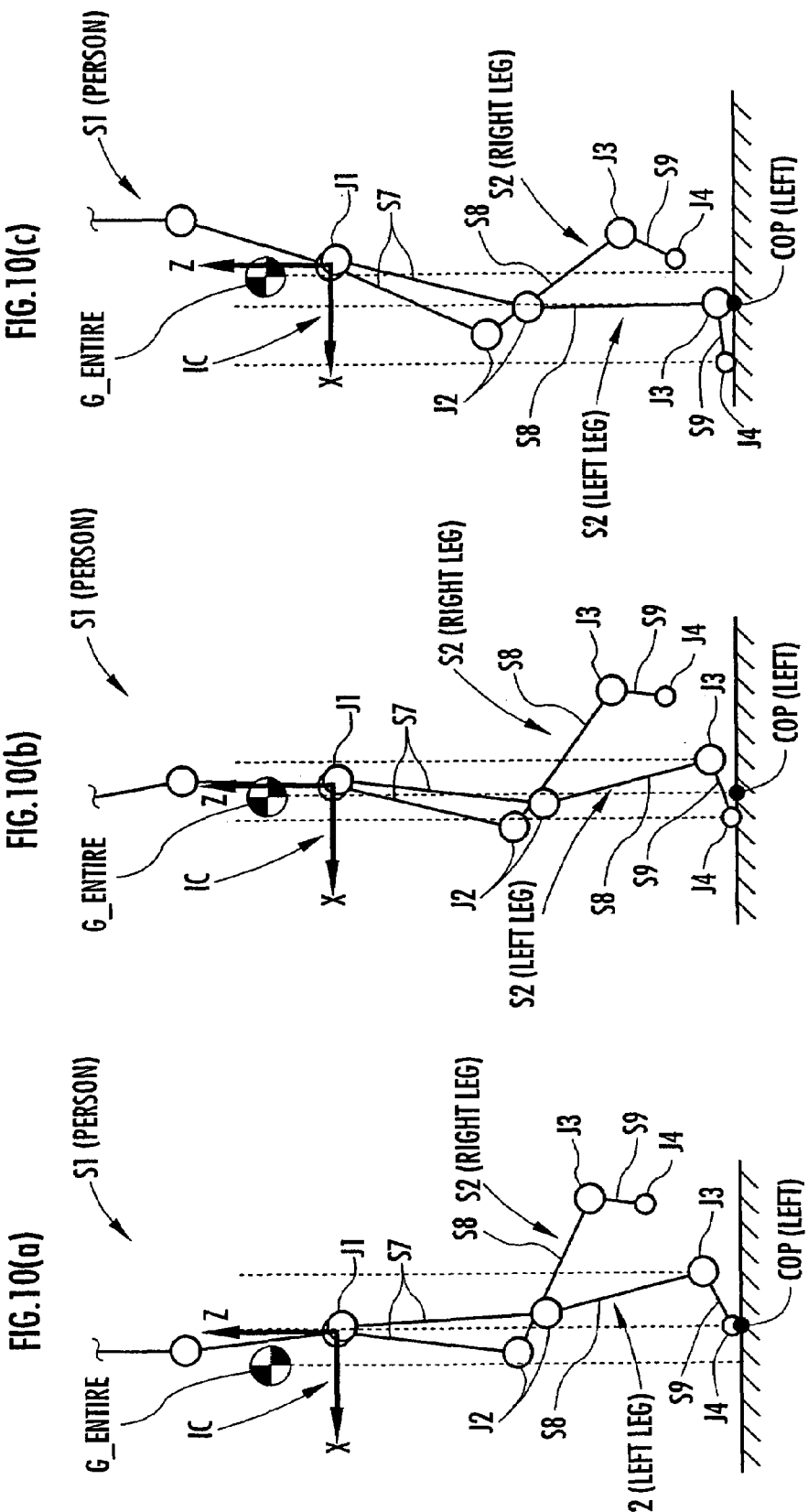
FIGS. 10($a$) to 10($c$) are diagrams for explaining methods of estimating a person's floor reaction force application point on the corresponding sagittal plane.
Figure 11:
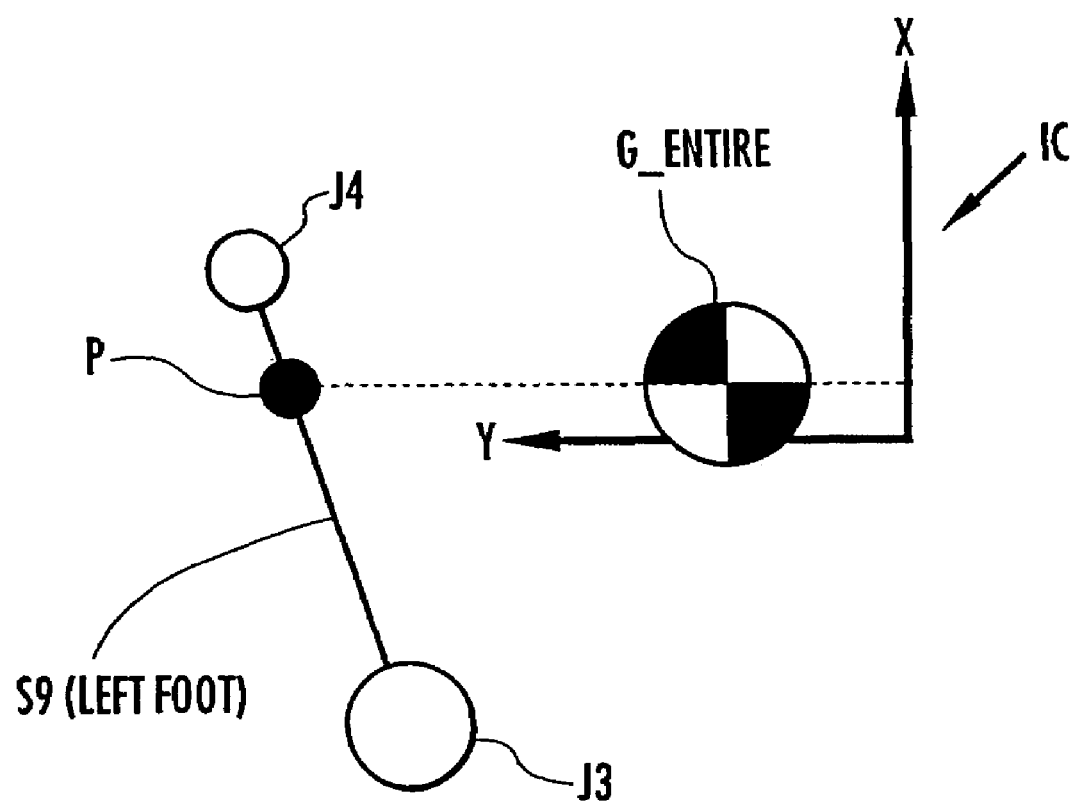
FIG. 11 is a diagram for explaining a method of estimating a person's floor reaction force application point on a horizontal plane.

Subsequently, for each leg determined to be in contact with the ground from the detected outputs of the landing sensors 34 and 35, the X-axis component and the Y-axis component of the position vector of a floor reaction force application point (the position vector on the absolute coordinate system IC) U(COP/IC) are determined according to the magnitude relation among the X-axis direction components U(G_entire/IC)x, U(J_ankle/IC)x, and U(J_MP/IC)x of the position vectors U(G_entire/IC), U(J_ankle/IC), and U(J_MP/IC), in other words, according to the relative horizontal positional relationship in the forward/backward direction of the entire center of gravity G_entire, the ankle joint J3, and the MP joint J4. The determination method is described in more detail below with reference to FIGS. 10(a) to 10(c) and FIG. 11. It should be noted here that the left leg is landing in the following description. FIGS. 10(a) to 10(c) illustrate the states in which the left leg of the person A is landing (single support states in these diagrams) viewed on the sagittal plane (the XZ plane on the absolute coordinate system IC). FIG. 11 shows a plan view of the landing foot portion in the state shown in FIG. 10(b). In FIG. 10 and FIG. 11, the person A is typified and shown by the human rigid link model S1.

As shown in FIG. 10(a), if the entire center of gravity G_entire is more forward than the MP joint of the landing left leg, in other words, if U(G_entire/IC)x>U(J_left MP/IC)x, the foot portion S9 of the left leg is in contact with the ground with the leg braced mainly in the toe-side portion. In this case, the floor reaction force application point COP exists substantially just under the MP joint J4 of the foot portion. Therefore, in this case, it is considered that the X- and Y-axis components of the position vector U(left COP/IC) of the floor reaction force application point COP are equal to the X- and Y-axis components of the position vector U(J_left MP/IC) of the MP joint J4, respectively. In other words, U(left COP/IC)x=U(J_left MP/IC)x and U(left COP/IC)y=U(J_left MP/IC)y.

Moreover, as shown in FIG. 10(c), if the entire center of gravity G_entire is more backward than the ankle joint J3 of the landing left leg, in other words, if U(G_entire/IC)x>U(J_left ankle/IC)x, the foot portion S9 of the left leg is in contact with the ground with the leg braced mainly in the heel-side portion. In this case, the floor reaction force application point COP exists substantially just under the ankle joint J3 of the left leg. Therefore, in this case, it is considered that the X- and Y-axis components of the position vector U(left COP/IC) of the floor reaction force application point COP are equal to the X- and Y-axis components of the position vector U(J_left ankle/IC) of the ankle joint J3, respectively. In other words, U(left COP/IC)x=U(J_left ankle/IC)x and U(left COP/IC)y=U(J_left ankle/IC)y.

Moreover, as shown in FIG. 10(b), if the entire center of gravity G_entire exists between the ankle joint J3 of the left leg and the MP joint J4 in the forward/backward direction, in other words, if U(G_left MP/IC)x≦U(G_entire/IC)x≦U(J_left ankle/IC)x, the floor reaction force application point COP exists substantially just under the entire center of gravity G_entire on the shown sagittal plane. Therefore, in this case, it is considered that the X-axis component of the position vector U(left COP/IC) of the floor reaction force application point COP is equal to the X-axis component of the entire center of gravity G_entire. In other words, U(left COP/IC)x=U(G_entire/IC)x. Then, the position of the floor reaction force application point COP is thought to be generally on a line segment generated by projecting the line segment between the center of the ankle joint J3 and the center of the MP joint J4 onto the floor surface. Accordingly, it is considered that the Y-axis component of the position vector U(left COP/IC) of the floor reaction force application point COP is equal to the Y-axis component of a point P where the value of the entire center of gravity G_entire is equal to the value of the X-axis component (the X-axis component on the absolute coordinate system IC) on the line segment between the center of the ankle joint J3 and the center of the MP joint J4 of the left leg as shown in FIG. 11. The value of the Y-axis component of the position vector U(left COP/IC) is found based on the following formula (7) indicating the proportional relation:

$$U(\text{left } COP/IC)x - U(\text{J\_left ankle}/IC)x : U(\text{J\_left } MP/IC)x - \qquad (7)$$
$$U(\text{J\_left ankle}/IC)x = U(\text{left } COP/IC)y -$$
$$U(\text{J\_left ankle}/IC)y : U(\text{J\_left } MP/IC)y - U(\text{J\_left ankle}/IC)y$$

Moreover, it is assumed that the Z-axis component of the position vector U(left COP/IC) of the floor reaction force application point is equal to the Z-axis component of the point, which is a predetermined value H0 (>0) away from the ankle joint J3 of the left leg downward in the vertical direction. In other words, it is assumed that U(left COP/IC)z=U(J_left ankle/IC)z−H0. In this regard, the predetermined value H0 is a distance in the vertical direction from the floor surface to the center of the ankle joint J3 in the state where the almost entire bottom face of the foot base 13 of the foot attachment portion 3 of the support orthosis 1 put on the person A is in contact with the horizontal floor surface, and it is previously measured and stored in the memory of the arithmetic processing unit 25. While the predetermined value H0 may be measured for each of the right and left legs, a value measured for one of the legs may be used for the both legs in common.

In this embodiment, the position vector U(left COP/IC) of the floor reaction force application point, which is an application point of the floor reaction force applied to the left leg when the left leg is in contact with the ground is found, as described hereinabove. The same applies to the right leg when it is in contact with the ground. In this instance, when the both legs are in contact with the ground, the position vector of the floor reaction force application point is found as described above for each of the both legs.

In this embodiment, the predetermined value H0 for use in finding the Z-axis component of the position vector U(COP/IC) of the floor reaction force application point has been defined as a constant value. If, however, the landing sensors 34 and 35 detect that the foot portion S9 is put in contact with the ground only in the toe-side portion, in other words, if only the landing sensor 35 outputs an ON signal indicating the presence of landing of the leg, the difference in the Z-axis component (U(J_ankle/IC)z−U(J_MP/IC)z) between the position vectors U(J_ankle/IC) and U(J_MP/IC) of the ankle joint J3 and the MP joint J4, namely, the distance in the vertical direction between the ankle joint J3 and the MP joint J4, instead of the predetermined value H0, regarding the landing leg, may be used. This improves the accuracy of U(COP/IC).

In the arithmetic processing of the floor reaction force application point estimation unit 57, the value U(COP/BC) on the body coordinate system BC of the position vector of the floor reaction force application point is found finally by multiplying the position vector U(COP/IC) of the floor reaction force application point obtained for the landing leg as described above by the inverse transformation tensor R(IC→BC), which is a transposition of the previously obtained transformation tensor R(BC→IC).

Figure 12:
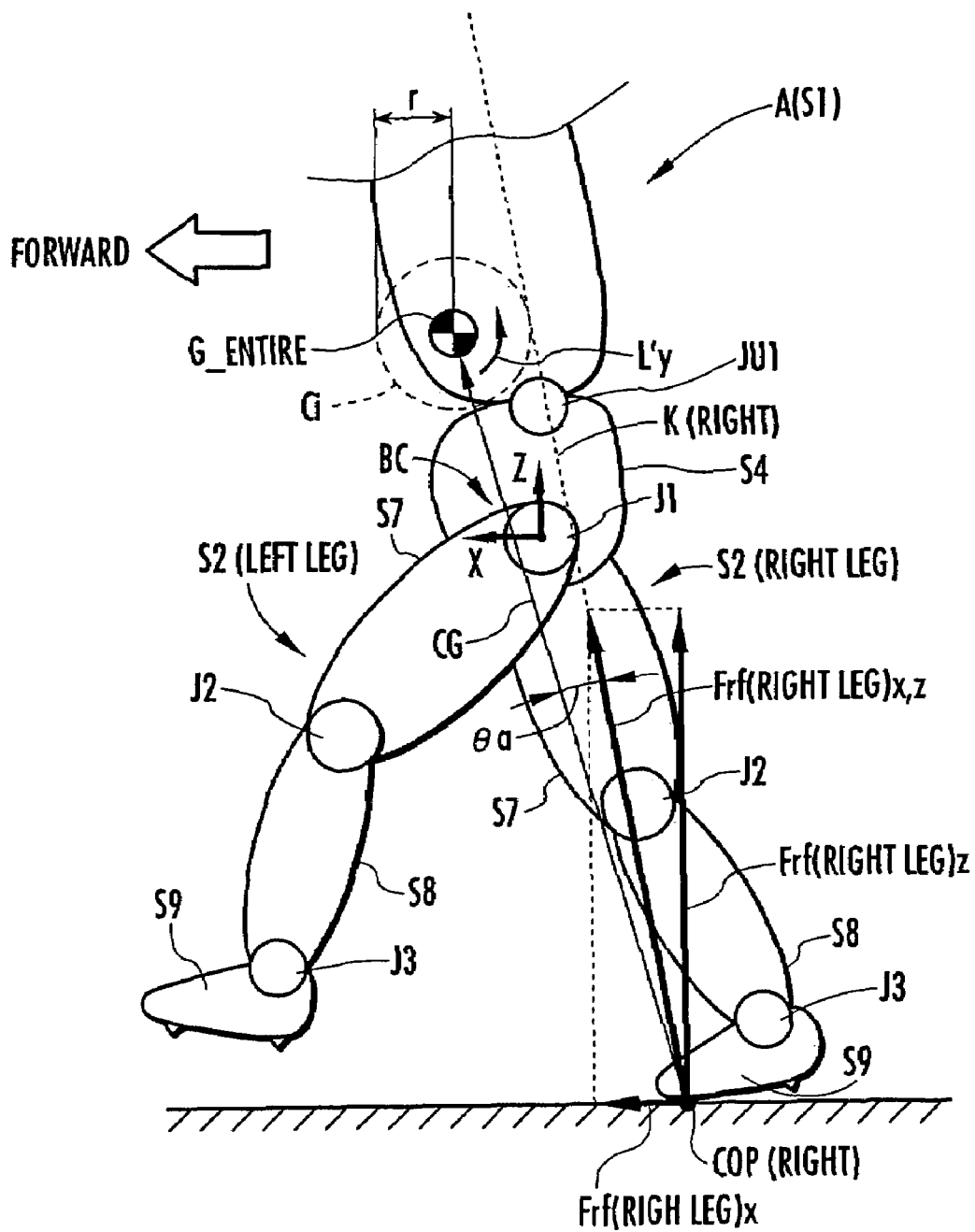
FIG. 12 is a diagram for explaining a method of estimating a floor reaction force in a person's floor reaction force in a single support state.
Figure 13:
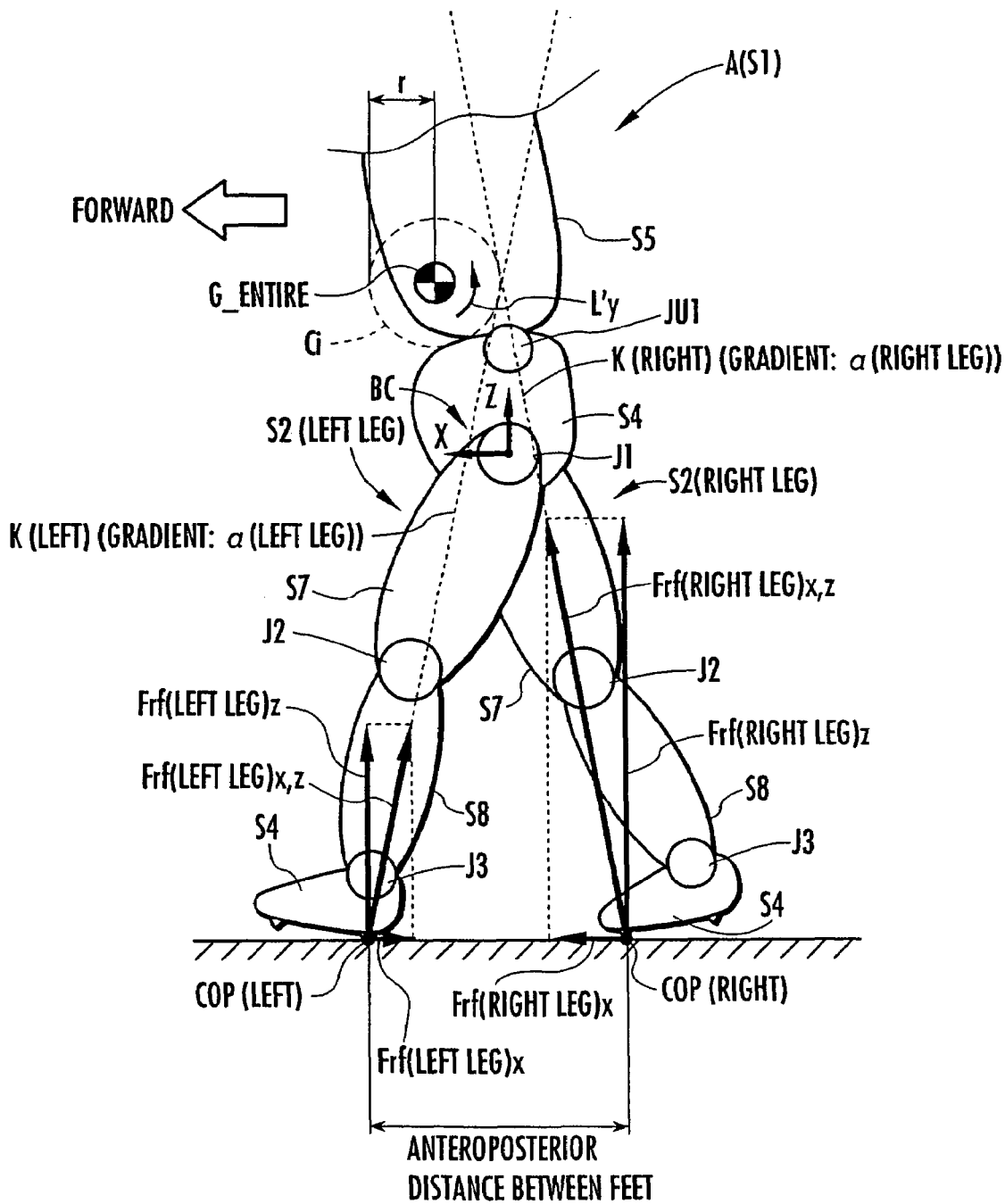
FIG. 13 is a diagram for explaining a method of estimating person's floor reaction forces in a double support state.

Subsequently, the arithmetic processing of the floor reaction force estimation unit 58 is described below. First, the principle of this arithmetic processing is described with reference to FIG. 12 and FIG. 13. FIG. 12 and FIG. 13 typically illustrate the lower part of the body of the person A in the single support state and in the double support state with the human rigid link model S1. In the human rigid link model S1 shown in FIG. 12 and FIG. 13, the rigid elements are represented as elements each having a size (width) for convenience of the illustration. In addition, in the description of the floor reaction force estimation unit 58, it is assumed that the vector quantities such as a floor reaction force, an angular momentum, a position vector and the like are represented by the body coordinate system BC, unless otherwise specified, and a term simply referred to as the X axis, the Y axis, or the Z axis means the corresponding coordinate axis of the body coordinate system BC. Therefore, when a vector quantity is denoted, the name of the coordinate system is often omitted. For example, a representation of a floor reaction force applied to the right leg of the person A with the body coordinate system BC is abbreviated as Frf(right leg), instead of Frf(right leg/BC), and its X-axis component is abbreviated as Frf(right leg)x.

While the person A is making a motion, the entire angular momentum of the person A varies with time. Unless an external force (except the gravity) other than the floor reaction force acts on the person A, the total rate of change of angular momentum, which is a time rate of change (time derivative) is equal to a moment generated around the entire center of gravity G_entire of the person A by the total floor reaction force (vector), which is the total sum of all floor reaction forces (vectors) acting on the person A (or a total sum of the moment generated around the G_entire by the floor reaction forces acting on the legs). In the single support state of the person A, the floor reaction force acting on the leg not landing is zero and therefore the floor reaction force acting on the landing single leg is the total floor reaction force. In the double support state of the person A, the total sum (vector sum) of the floor reaction forces acting on the landing both right and left legs is the total floor reaction force. As supplementary information, although an actual floor reaction force acting on the landing leg is distributed over the supporting surface of the leg, it is assumed in this specification that the floor reaction force focuses on the floor reaction force application point COP of the leg (the center of gravity of the floor reaction force distributed over the supporting surface exists at the floor reaction force application point COP).

Moreover, in general, the magnitude of a component around an arbitrary axis XX of a moment generated around an arbitrary point PP generated by a certain translational force is equal to a value found by multiplying the magnitude of the component on a plane SS of the translational force (the component perpendicular to the axis XX of the translational force) by a moment arm length, which is a distance between a line of action of the translational force (a straight line passing through the application point of the translational force and having the same direction as the translational force) and a point PP, viewed on the plane SS perpendicular to the axis XX.

Therefore, the magnitude of the component around a predetermined axis of the total rate of change of angular momentum of the person A is coincident with the value found by multiplying the magnitude (an absolute value) of the component vector (two-dimensional vector) on a plane perpendicular to the predetermined axis of the total floor reaction force acting on the person A by a moment arm length having a certain length. In addition, the direction of the moment, which is generated around G_entire by the component on the plane perpendicular to the predetermined axis, of the total floor reaction force is coincident with the direction of the component around the predetermined axis of the total rate of change of angular momentum.

In consideration of the above, the direction of the component vector on the plane perpendicular to the predetermined axis of the floor reaction force acting on the landing leg 2 is regulated by using the aforementioned moment arm length and the component (particularly the direction) around the predetermined axis of the total rate of change of angular momentum in this embodiment.

More specifically, focusing attention on the component around the Y axis (the axis in the right/left direction of the person A) of the total rate of change of angular momentum of the person A, in the single support state of the person A shown in FIG. 12, the direction of the component vector Frf(right leg)x,z on the plane (XZ plane) perpendicular to the Y axis of the floor reaction force Frf(right leg) (=total floor reaction force) acting on the leg (the right leg in the shown example) landing via the foot attachment portion 3 is regulated to the direction satisfying the conditions where its line of action K (in the shown example, the straight line K(right) passing through the floor reaction force application point COP of the landing right leg) is tangent to a circle Ci having a radius r (=moment arm length) whose center is G_entire and the direction of the moment generated around G_entire by Frf (righ leg)x,z having the direction of the line of action is the same as the direction of a component L'y around the Y axis of the total rate of change of angular momentum L' (L' indicates a first derivative of the total angular momentum L). The same applies to the regulation in the single support state in which only the left leg is landing via the foot attachment portion 3.

As additional information, in the single support state, the floor reaction force acting on the landing leg is equal to the total floor reaction force, and therefore when regulating the direction of the component vector on the XZ plane of the floor reaction force acting on the landing leg as described above, the direction of the moment generated around G_entire by the component vector on the XZ plane of the total floor reaction force is also the same as the direction of the component L'y around the Y axis of the total rate of change of angular momentum. Then, if so, the value found by multiplying the magnitude (absolute value) of the component vector Frf(leg) x,z on the plane perpendicular to the Y axis of the floor reaction force acting on the landing leg by the moment arm length r, which is the radius of the circle Ci, is coincident with the magnitude (absolute value) of the component L'y around the Y axis of the total rate of change of angular momentum.

Moreover, in the double support state of the person A shown in FIG. 13, the direction of the component vector Frf(right leg)x,z on the plane (XZ plane) perpendicular to the Y axis of the floor reaction force Frf(right leg) acting on the right leg is regulated to the direction satisfying the conditions where its line of action K(right) is tangent to a circle Ci having a radius r (=moment arm length) whose center is G_entire and the direction of the moment generated around G_entire by Frf(righ leg)x,z having the direction of the line of action K(right) is the same as the direction of a component L'y around the Y axis of the total rate of change of angular momentum L'. Similarly, the direction of the component vector Frf(left leg)x,z on the plane (XZ plane) perpendicular to the Y axis of the floor reaction force Frf(left leg) acting on the left leg is regulated to the direction satisfying the conditions where its line of action K(left) is tangent to the circle Ci having the radius r and the direction of the moment generated around G_entire by Frf(left leg)x,z having the direction of the line of action K(left) is the same as the direction of the component L'y around the Y axis of the total rate of change of angular momentum L'.

As additional information, in the double support state, when regulating the direction of the component vector on the XZ plane of the floor reaction force acting on each of the landing right and left legs as described above, the direction of the moment generated around G_entire by the total sum of the component vectors (the component vector on the XZ plane of the total floor reaction force) is also the same as the direction of the component L'y around the Y axis of the total rate of change of angular momentum. In this instance, however, the total sum of the values found by multiplying the magnitude (absolute value) of the component vector Frf(right leg)x,z on the XZ plane of the floor reaction force Frf(right leg) acting on the right leg and the magnitude (absolute value) of the component Frf(left leg)x,z on the XZ plane of the floor reaction force Frf(left leg) acting on the left leg each by the moment arm length r, which is the radius of the circle Ci, is not coincident with the magnitude of the component L'y around the Y axis of the total rate of change of angular momentum L' in general.

In consideration of the above description, in the arithmetic processing of the floor reaction force estimation unit 58 in this embodiment, the moment arm length r is calculated from the component L'y around the Y axis of the total rate of change of angular momentum L' and the component vector on the plane perpendicular to the Y axis (the component on the XZ plane as a sagittal plane of the body coordinate system BC) of the total floor reaction force (hereinafter, referred to as Frf(entire)), as described hereinafter. Then, by using the moment arm length r, the direction of the floor reaction force acting on the each landing leg (more specifically, the component vector on the XZ plane of the floor reaction force) is determined. By determining the direction of the floor reaction force in this manner, the ratio of the each coordinate component value of the floor reaction force is determined. Therefore, it becomes possible to find the each coordinate component value of the floor reaction force from the ratio and the total floor reaction force. The Y-axis component of the floor reaction force does not much affect the joint moment (the joint moment around the axis perpendicular to the leg plane PL) finally calculated by the human-side joint moment estimation unit 41, and thus the Y-axis component of the floor reaction force is ignored in this embodiment (the Y-axis component is assumed to be zero).

The arithmetic processing of the floor reaction force estimation unit 58 is described specifically with reference to FIG.

Figure 14:
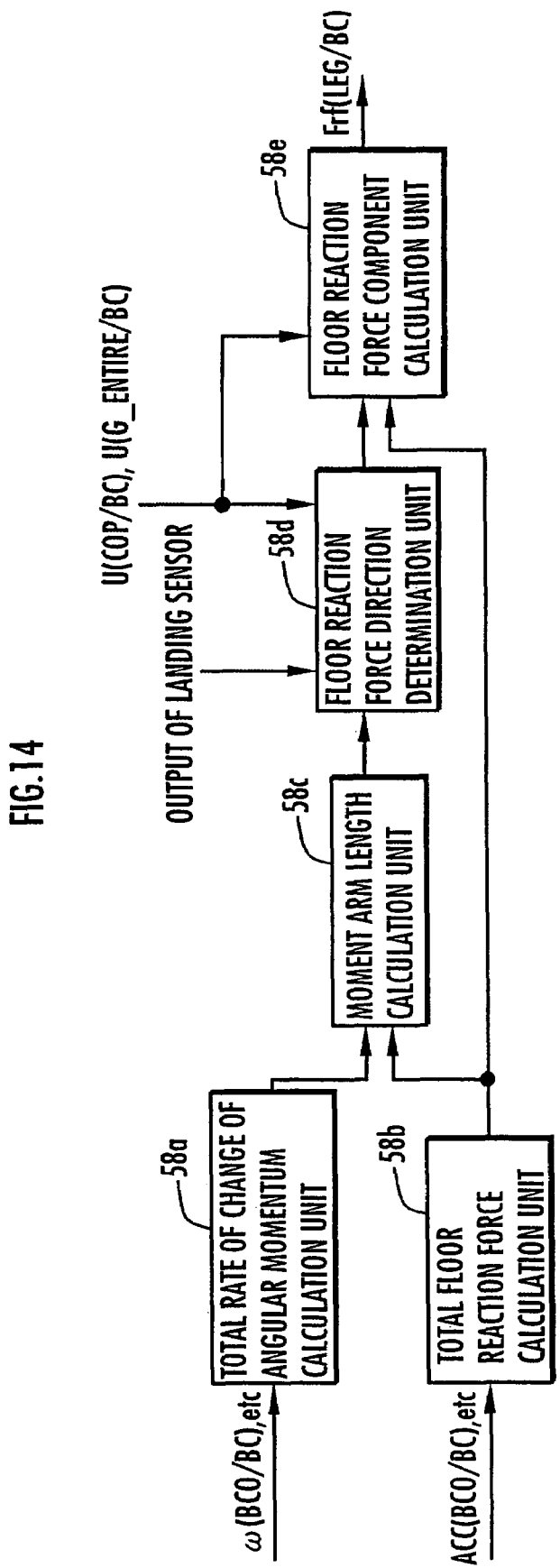
FIG. 14 is a block diagram showing an arithmetic processing function of the floor reaction force estimation unit shown in FIG. 7.

14 or the like hereinafter. FIG. 14 is a block diagram showing an arithmetic processing function of the floor reaction force estimation unit 58.

As shown in FIG. 14, the floor reaction force estimation unit 58 includes a total rate of change of angular momentum calculation unit 58a, a total floor reaction force calculation unit 58b, a moment arm length calculation unit 58c, a floor reaction force direction determination unit 58d, and a floor reaction force component calculation unit 58e. The total rate of change of angular momentum calculation unit 58a receives inputs of the angular velocity ω(BCO/BC) of the origin BCO of the body coordinate system BC calculated by the body coordinate system acceleration and angular velocity calculation unit 54, the position vectors of the joint elements and the position vectors of the centers of gravity of the rigid elements calculated by the three-dimensional joint and element center-of-gravity location calculation unit 53, and the position vector of G_entire calculated by the entire center-of-gravity location calculation unit 56.

Then, using these input values, the total rate of change of angular momentum calculation unit 58a calculates the component L'y around the Y axis of the total rate of change of angular momentum L' by calculating the following formula (8a):

$$L'y = \sum (I\_n \times \theta''(n)y) + \sum (m\_n \times \Delta U(G\_n) \times \Delta ACC(G\_n))y \quad (8a)$$

Subject to:

$$\Delta U(G\_n) \equiv U(G\_n) - U(G\_{entire}) \Delta ACC(G\_n)$$
$$\equiv ACC(G\_n) - ACC(G\_{entire})$$
$$= U(G\_n)'' - U(G\_{entire})''$$

In this formula (8a), "n" indicates a number assigned arbitrarily to each rigid element: I_n is a moment of inertia of a rigid element having the number n and θ"(n) is an angular acceleration around the center of gravity of the rigid element having the number n. Therefore, the first term Σ calculation in the formula (8a) is to add up the product values of the moment of inertia of each rigid element I_n and the Y-axis component of the angular acceleration θ"(n) (the Y-axis component of the moment generated by the rigid element with its rotary motion) calculated regarding all the rigid elements. In addition, m_n is a weight of the rigid element having the number n, U(G_n) is a position vector on the body coordinate system BC of the center of gravity of the rigid element having the number n, ACC(G_n) is an acceleration of the center of gravity of the rigid element having the number n, ΔU(G_n) is a position vector relative to G_entire of the center of gravity of the rigid element having the number n, and ΔACC(G_n) is a relative acceleration to G_entire of the center of gravity of the rigid element having the number n. Therefore, the second term Σ calculation in the formula (8a) is to add up the Y-axis components of the values obtained regarding all the rigid elements by multiplying a vector product of a position vector ΔU(G_n) to G_entire of the center of gravity of each rigid element and a relative acceleration ΔACC(G_n) to the entire center of gravity G_entire of the center of gravity of the rigid element by the weight of the rigid element (a moment generated around G_entire by the rigid element with its translation acceleration motion of the center of gravity). Incidentally, supposing that r(G_n) is a distance on the XZ plane between a straight line passing through the center of gravity of the rigid element of the number n and having the same direction as ΔACC(G_n) and G_entire and that θ(G_n) is an angular acceleration around the Y axis of the center of gravity of the rigid element when the translation motion of the center of gravity of the rigid element of the number n is considered to be a rotary motion around G_entire, the Y-axis component (=(ΔU(G_n)×ΔACC(G_n))y) of the vector product of ΔU(G_n) and ΔACC(G_n) equals r(G_n)²×θ(G_n).

In this instance, I_n necessary for the first term Σ calculation in the formula (8a) is previously stored in the memory, not shown, of the arithmetic processing unit 25. In addition, θ"(n)y can be found as described below. Specifically, the angles of inclination of the rigid elements on the XZ plane (the sagittal plane on the body coordinate system BC) are sequentially calculated from the position vectors (U(J_left hip/BC) or the like) of the joint elements of the leg S2 calculated by the three-dimensional joint and element center-of-gravity location calculation unit 53. Furthermore, the Y-axis component θ"(n)y of the angular acceleration of the rigid element is found by adding the first derivative of the Y-axis component of the angular velocity ω(BCO/BC) of the origin BCO of the body coordinate system BC calculated by the body coordinate system acceleration and angular velocity calculation unit 54 to the second derivative of the angle of inclination.

Moreover, ΔU(G_n) necessary for the second term Σ calculation in the formula (8a) is determined according to the definition of the provision for the formula (8a) from the position vector (U(G_thigh/BC) or the like) of the center of gravity of the each rigid element calculated by the three-dimensional joint and element center-of-gravity location calculation unit 53 and the position vector U(G_entire/BC) of G_entire calculated by the entire center-of-gravity location calculation unit 56. Furthermore, ΔACC(G_n) is determined according to the definition of the provision for the formula (8a) from the second derivative U(G_n)" of the position vector of the center of gravity of the each rigid element calculated by the three-dimensional joint and element center-of-gravity location calculation unit 53 and the second derivative U(G_entire)" of the position vector of G_entire calculated by the entire center-of-gravity location calculation unit 56.

The total floor reaction force calculation unit 58b receives inputs of the acceleration ACC(BCO/BC) of the origin BCO of the body coordinate system BC calculated by the body coordinate system acceleration and angular velocity calculation unit 54 and the position vector U(G_entire/BC) of G_entire calculated by the entire center-of-gravity location calculation unit 56.

Then, the total floor reaction force calculation unit 58b calculates component vector Frf(entire)x,z (a two-dimensional vector made of the X-axis component and the Z-axis component of Frf(entire)) on the XZ plane of the total floor reaction force Frf(entire) from the above input values by calculating the following formula (8b):

$$Frf(entire)x, z = entire\ weight \times (ACC(BCO/BC) + U(G\_{entire}/BC)'')x, z \quad (8b)$$

More specifically, the component vector Frf(entire)x,z perpendicular to the Y axis of the total floor reaction force is found by multiplying a component on the XZ plane of the vector (this means the acceleration of G_entire) obtained by adding the acceleration ACC(BCO/BC) of the origin BCO of the body coordinate system BC to the second derivative U(G_entire/BC)" of the position vector U(G_entire/BC) of G_entire by the entire weight of the person A.

Subsequently, the component L'y around the Y axis of the total rate of change of angular momentum L' calculated as described above and the component vector Frf(entire)x,z on the XZ plane (sagittal plane) of the total floor reaction force are input to the moment arm length calculation unit 58c, where the moment arm length is calculated from the input values. In this instance, as described above, the magnitude of L'y is coincident with the product obtained by multiplying the magnitude of the component vector Frf(entire)x,z on the XZ plane of the total floor reaction force by the moment arm length. Therefore, the moment arm length calculation unit 58c calculates the moment arm length r by the following formula (8c):

$$r=L'y/|Frf(entire)x,z| \quad (8c)$$

In this embodiment, the moment arm length r obtained by the above formula (8c) takes a positive or negative value according to the direction (sign) of the component L'y around the Y axis of the total rate of change of angular momentum. In this instance, if L'y has the direction indicated by the arrow shown in FIG. 12 and FIG. 13, the L'y value is determined to be positive in this embodiment. Therefore, whether the moment arm length r is a positive value or a negative value determines the direction of the moment generated around G_entire (the moment around the Y axis) by Frf(entire)x,z.

The moment arm length r obtained in this manner is then input to the floor reaction force direction determination unit 58d. The floor reaction force direction determination unit 58d further accepts outputs of the landing sensors 34 and 35, the position vector U(COP/BC) of the floor reaction force application point COP estimated by the floor reaction force application point estimation unit 57, and the position vector U(G_entire/BC) of G_entire calculated by the entire center-of-gravity location calculation unit 56. Thereafter, the floor reaction force direction determination unit 58d determines the direction of the floor reaction force acting on the landing leg as described below, by using these input values.

First, it is determined whether the person A is in the double support state or in the single support state on the basis of the detected outputs of the landing sensors 34 and 35. More specifically, if one of the landing sensors 34 and 35 of one leg outputs the ON signal indicating the presence of landing of the leg and one of the landing sensors 34 and 35 of the other leg outputs the ON signal indicating the presence of landing of the leg, it is determined that the person A is in the double support state. Moreover, if one of the landing sensors 34 and 35 of one of the legs outputs the ON signal indicating the presence of landing of the leg and neither of the landing sensors 34 and 35 of the other leg outputs the ON signal, it is determined that the person A is in the single support state.

Moreover, when the person A is in the double support state, regarding the direction (the direction on the XZ plane) of the floor reaction force Frf(right leg) of the right leg, the gradient α(right leg) on the body coordinate system BC of the straight line K(right), which passes through the floor reaction force application point COP of the right leg and is tangent to the circle having the radius r (more accurately, |r|) whose center is G_entire, is determined to indicate the direction (the direction on the XZ plane) of the floor reaction force Frf(right leg) of the right leg, as shown in FIG. 13. In this instance, if the moment arm length r is positive, the straight line K(right) is assumed to be tangent to the backward portion of the circle Ci having the radius r. In other words, when the component vector Frf(right leg)x,z on the XZ plane of the floor reaction force Frf(right leg) acts on the floor reaction force application point COP with the straight line K(right) as a line of action, the gradient α(right leg) of the straight line K(right) tangent to the circle Ci is determined in such a way that the direction of the component around the Y axis of the moment generated around G_entire by the force application is the same as the direction of the component L'y around the Y axis of the total rate of change of angular momentum L'. Regarding the left leg, the gradient α(left leg) on the body coordinate system BC of the straight line K(left), which indicates the direction (the direction on the sagittal plane) of the floor reaction force Frf(left leg) of the left leg, is determined in the same manner as for the right leg. In this embodiment, the gradient α is a value of a ratio of variation in the Z-axis direction to the unit variation in the X-axis direction of the straight line K.

When the person A is in the single support state, as shown in FIG. 12, CG is defined as the component vector on the XZ plane (the two-dimensional vector viewed on the sagittal plane of the body coordinate system BC) of the vector from the floor reaction force application point COP of the landing leg (the right leg in the shown example) to G_entire (the position vector of G_entire to COP). Then, the angle θa formed by the vector CG and the straight line K(right), which passes through the floor reaction force application point COP of the right leg and is tangent to the circle having the radius r (more accurately, |r|) whose center is G_entire, is determined to represent the direction (the direction on the sagittal plane) of the floor reaction force Frf(right leg). In this instance, if the moment arm length r is positive, the straight line K(right) is assumed to be tangent to the backward portion of the circle Ci having the radius r. In other words, when the component vector Frf(right leg)x,z on the XZ plane of the floor reaction force Frf(right leg) acts on the floor reaction force application point COP with the straight line K(right) as a line of action, the angle θa on the XZ plane of the straight line K(right) to the vector CG in such a way that the direction of the component around the Y axis of the moment generated around G_entire by the force application is the same as the direction of the component around the Y axis of the total rate of change of angular momentum.

The angle θa is calculated by the following formula (8d):

$$\theta a = -\sin^{-1}(r/|CG|) \quad (8d)$$

In this instance, the absolute value of the vector CG is calculated from the position vector U(right COP/BC) of the floor reaction force application point COP found by the floor reaction force application point estimation unit 57 and the position vector U(G_entire/BC) of G_entire found by the entire center-of-gravity location calculation unit 56.

Also in the single support state in which only the left leg is landing, similarly to the above, the angle θa formed by the component vector CG on the XZ plane of the position vector of G_entire to the floor reaction force application point COP of the left leg and the straight line K(left), which passes through the floor reaction force application point COP of the left leg and is tangent to the circle having the radius r (more accurately, |r|) whose center is G_entire, is determined to represent the direction of the component vector Frf(left leg) x,z on the XZ plane of the floor reaction force Frf(left leg).

By the processing of the floor reaction force direction determination unit 58d described hereinabove, the direction (the direction on the sagittal plane of the body coordinate system BC) of the floor reaction force Frf acting on the landing leg 2 is determined in such a way that the line of action of the component vector Frf(leg)x,z on the XZ plane (the sagittal plane of the body coordinate system BC) of the floor reaction force Frf acting on the landing leg 2 is tangent to the circle Ci whose radius is the moment arm length r determined by the formula (8c) and whose center is G_entire and that the moment generated around G_entire by Frf(leg)x,z having the direction of the line of action is coincident with the component L'y around the Y axis of the total rate of change of angular momentum.

Subsequently, the direction (the gradient α in the double support state or the angle θa in the single support state) of the floor reaction force determined by the floor reaction force direction determination unit 58d is input to the floor reaction force component calculation unit 58e. The floor reaction force component calculation unit 58e also accepts the component Frf(entire)x,z on the XZ plane of the total floor reaction force found by the total floor reaction force calculation unit 58b. In the single support state, the floor reaction force direction determination unit 58d inputs the vector CG found by its processing into the floor reaction force component calculation unit 58e. Moreover, the position vector U(COP/BC) of the floor reaction force application point COP of the each leg and the position vector U(G_entire/BC) of G_entire are also input to the floor reaction force component calculation unit 58e.

Then, the floor reaction force component calculation unit 58e finds the coordinate component values on the body coordinate system BC of the floor reaction force Frf acting on the landing leg from these input values as described below.

First, the calculation procedure in the double support state is described below. The floor reaction forces (more specifically, their X-axis components and Z-axis components) acting on the legs in the double support state are determined based on the following relational expressions (9a) to (9d):

$$Frf(\text{right leg})x + Frf(\text{left leg})x = Frf(\text{entire})x \quad (9a)$$

$$Frf(\text{right leg})z + Frf(\text{left leg})z = Frf(\text{entire})z \quad (9b)$$

$$Frf(\text{right leg})z = \alpha(\text{right leg}) \times Frf(\text{right leg})x \quad (9c)$$

$$Frf(\text{left leg})z = \alpha(\text{left leg}) \times Frf(\text{left leg})x \quad (9d)$$

The expressions (9a) and (9b) represent that the total sum of the floor reaction forces acting on the legs is coincident with the total floor reaction force. Moreover, the formulas (9c) and (9d) represent that the ratio of the component value of the floor reaction force is determined according to the direction of the floor reaction force acting on the each leg.

Then, Frf(right leg)x, Frf(right legz, Frf(left leg)x, and Frf(left leg)z are found by the following formulas (9e) to (9h) from these formulas (9a) to (9d), respectively:

$$Frf(\text{right leg})x = (Frf(\text{entire})z - \alpha(\text{left leg}) \times Frf(\text{entire})x)/\Delta\alpha \quad (9e)$$

$$Frf(\text{right leg})z = (\alpha(\text{right leg}) \times Frf(\text{entire})z - \alpha(\text{right leg}) \times \alpha(\text{left leg}) \times Frf(\text{entire})x)/\Delta\alpha \quad (9f)$$

$$Frf(\text{left leg})x = (-Frf(\text{entire})z + \alpha(\text{right leg}) \times Frf(\text{entire})x)/\Delta\alpha \quad (9g)$$

$$Frf(\text{left leg})z = (-\alpha(\text{left leg}) \times Frf(\text{entire})z + \alpha(\text{right leg}) \times \alpha(\text{left leg}) \times Frf(\text{entire})x)/\Delta\alpha \quad (9h)$$

Subject to: $\Delta\alpha = \alpha(\text{right leg}) - \alpha(\text{left leg})$

Therefore, in the double support state, basically the X-axis component and the Z-axis component of the floor reaction force acting on the each leg, namely, Frf(leg)x,z can be calculated by the arithmetic operations of the right-hand sides of the above expressions (9e) to (9h).

If the distance in the forward/backward direction (in the X-axis direction) between the foot portions (the foot elements S9) of the both legs is short in the double support state, the values of α(right leg) and α(left leg) are close to each other (the value of Δα is close to zero), thereby lowering the accuracy of the floor reaction force obtained by the aforementioned formulas (9e) to (9h).

In this regard, if the distance between the both foot portions (the foot elements S9, S9) in the X-axis direction (hereinafter, referred to as the anteroposterior distance between feet. See FIG. 13) is short in the double support state, it is considered that the floor reaction forces acting on the both legs 2, 2 are substantially equal to each other. In addition, the direction of the component around the Y axis of the moment generated around G_entire by the resultant force of them should be coincident with the direction of the component L'y around the Y axis of the total rate of change of angular momentum. Therefore, if the anteroposterior distance between feet is equal to or lower than a predetermined first threshold value, the X-axis components and the Z-axis components of the floor reaction forces acting on the legs 2 are calculated by the following formula (10) in this embodiment:

$$Frf(\text{right leg})x, z = Frf(\text{left leg})x, z = Frf\_s(\text{entire})x, z/2 \quad (10)$$

Subject to:

$$Frf\_s(\text{entire})x, z = \begin{bmatrix} \cos\theta b & \sin\theta b \\ -\sin\theta b & \cos\theta b \end{bmatrix} \times CavG \times \frac{|Frf(\text{entire})x, z|}{|CavG|}$$

CavG in the provision for the formula (10) is a component vector on the XZ plane of the vector from the midpoint Cav of the line segment between the respective floor reaction force application points COPs of the right and left legs to G_entire (the position vector of G_entire relative to the midpoint Cav). The position vector on the body coordinate system BC of Cav is calculated as an average value of the position vectors of the right and left floor reaction force application points COPs (=(U(right COP/BC)+U(left COP/BC))/2). Moreover, θb is an angle formed by the vector CavG and a straight line passing through the midpoint Cav on the XZ plane and having a radius r (more accurately, |r|) whose center is G_entire and is calculated by the formula in which "CG" in the right-hand side of the formula (8d) is replaced with "CavG." Therefore, Frf_s(entire)x,z in the formula (10) is a vector (two-dimensional vector) that has the same direction as the component vector on the XZ plane of the vector from the midpoint Cav of the line segment between the floor reaction force application points COPs of the both legs to G_entire and is generated by rotating a vector having the magnitude of Frf(entire)x,z by the angle θb around the midpoint Cav on the XZ plane (the sagittal plane). Therefore, on the XZ plane, the line of action of Frf_s(entire)x,z (the straight line passing through the midpoint on the XZ plane and having the same direction as the vector Frf_s(entire)x,z) is tangent to the circle Ci having the radius r whose center is G_entire.

Therefore, if the anteroposterior distance between feet is equal to or smaller than the first threshold value in the double support state, Frf(right leg)x,z and Frf(left leg)x,z obtained by the formula (10) have the same magnitude and the direction and the magnitude of the total sum is the same as the magnitude of the total floor reaction force Frf(entire). Moreover, if the anteroposterior distance between feet is equal to or smaller than the first threshold value, the position on the XZ plane of the floor reaction force application point COP of the each leg is substantially the same as the position on the XZ plane of the midpoint Cav. Therefore, each of the lines of action of Frf(right leg)x,z and Frf(left leg)x,z (the lines of action on the XZ plane each passing through the floor reaction force application point COP) is substantially tangent to the circle Ci having the radius r whose center is G_entire.

Moreover, if the anteroposterior distance between feet is equal to or greater than a predetermined second threshold value greater than the first threshold value, the X-axis component and the Z-axis component acting on each leg are calculated by the formulas (9e) to (9h). Furthermore, if the anteroposterior distance between feet is a distance between the first threshold value and the second threshold value, an arithmetic weighted mean value between the X-axis and Z-axis components of the floor reaction force obtained by the formulas (9e) to (9h) (hereinafter, a vector composed of a pair of these components is indicated by reference symbol Frf1x,z) and the X-axis and Z-axis components of the floor reaction force obtained by the formula (10) (hereinafter, a vector composed of a pair of these components is indicated by reference symbol Frf2x,z) is calculated as the X-axis component and the Z-axis component of the floor reaction force acting on each leg and the value of the weighting factor is continuously varied according to the anteroposterior distance between feet.

Therefore, the component vector Frf(leg)x,z (a true value of the estimated value of Frf(leg)x,z)) on the XZ plane of the floor reaction force of the each leg finally calculated by the floor reaction force component calculation unit 58e in the double support state is found by the following formula (11a):

$$Frf(\text{leg})x,z = W \times Frf1x,z + (1-W) \times Frf2x,z \quad (11a)$$

Figure 15:
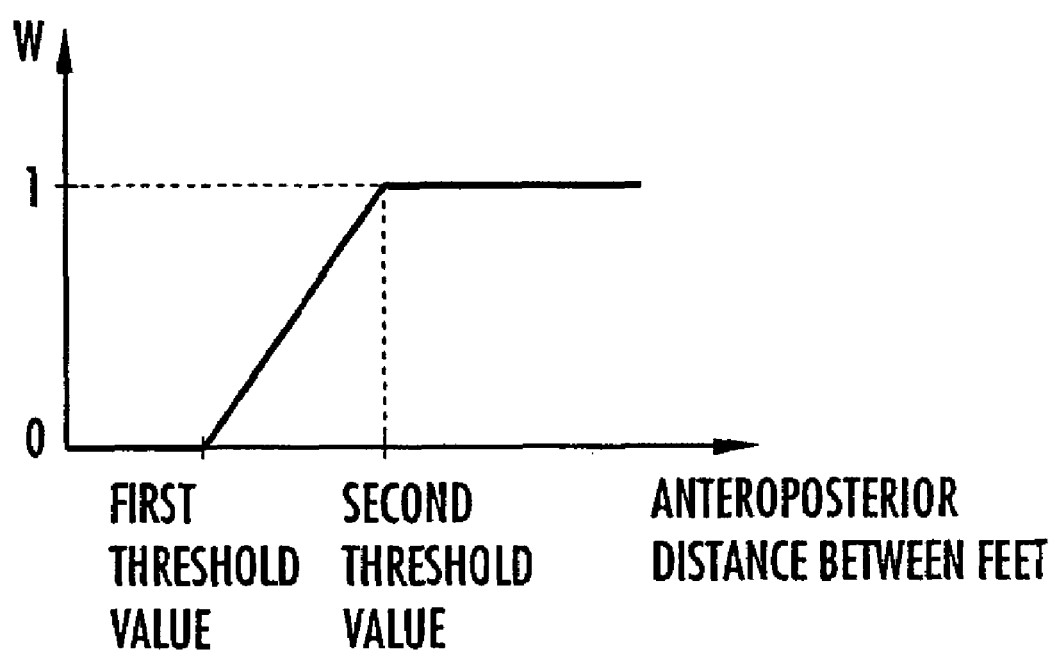
FIG. 15 is a graph showing a relation between a weighting factor and an anteroposterior distance between feet for use in processing of a floor reaction force component calculation unit shown in FIG. 14.
Figure 16:
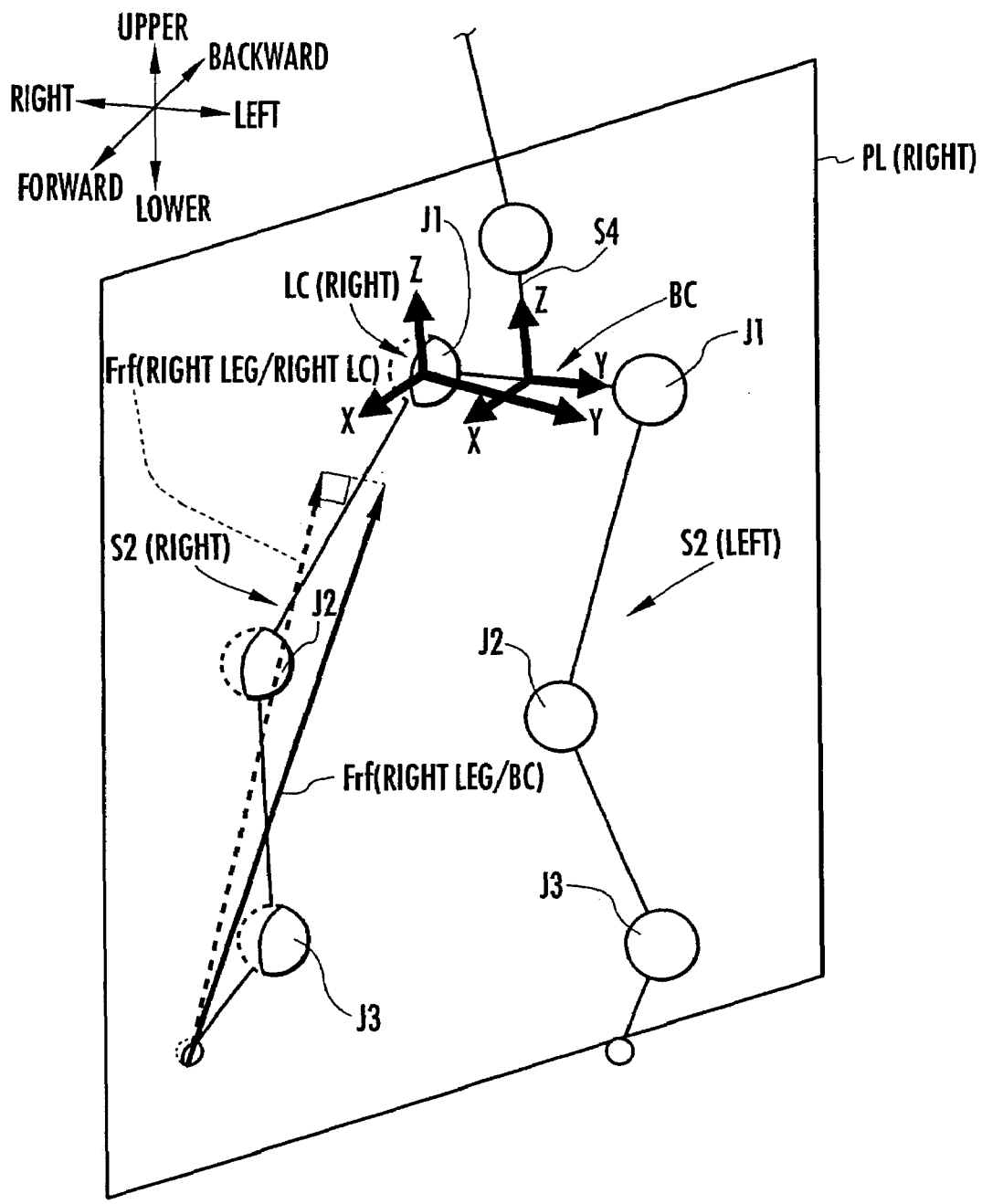
FIG. 16 is a diagram for explaining processing of a leg plane projection unit shown in FIG. 7.

In the above, W is a weighting factor and its value is determined according to the anteroposterior distance between feet by the data table defined as shown in FIG. 15 or an arithmetic expression. In this instance, a distance used as the anteroposterior distance between feet is, for example, the distance in the X-axis direction on the body coordinate system BC of the corresponding floor reaction force application point COP of each of the legs, namely, |U(right COP/BC)x−U(left COP/BC)x|. Incidentally, it is also possible to use a distance in the X-axis direction of the MP joint or a distance in the X-axis direction of the ankle joint of the each leg, for example, as the anteroposterior distance between feet.

Additionally, in the double support state, the straight line K(right) or the straight line K(left) may be substantially parallel to the Z axis in some cases. If so, the absolute value of the gradient α(right leg) or α(left leg) is infinity or excessively large. Therefore, in this embodiment, in case that the absolute value of the gradient α exceeds a predetermined value, the value of α is forcibly limited to the predetermined value.

On the other hand, the floor reaction force (more specifically, its X-axis component and Z-axis component) acting on the leg landing via the foot attachment portion 3 in the single support state is calculated by the following formula (11b):

$$Frf(\text{leg})x, z = \begin{bmatrix} \cos\theta a & \sin\theta a \\ -\sin\theta a & \cos\theta a \end{bmatrix} \times CG \times \frac{|Frf(\text{entire})x, z|}{|CG|} \quad (11b)$$

In other words, the component vector Frf(leg)x,z on the XZ plane of the floor reaction force acting on the landing leg is found as a vector generated by rotating a vector, starting from the floor reaction force application point COP of the leg to G_entire and having the magnitude of Frf(entire)x,z, by the angle θa around the floor reaction force application point COP on the XZ plane (the sagittal plane). The line of action of Frf(leg)x,z found in this manner is tangent to the circle Ci having the radius r whose center is G_entire.

In this embodiment, in either case of the double support state or the single support state, the Y-axis component of the floor reaction force is assumed to be zero as described above. In the single support state, the floor reaction force acting on the leg not landing is assumed to be zero.

With the above processing of the floor reaction force component calculation unit 58e, in the double support state, the lines of action (the lines of action each passing through the floor reaction force application point COP of the each leg on the XZ plane) of the component vectors Frf(right leg)x,z and Frf(left leg)x,z of the floor reaction force are tangent to the circle Ci having the radius r (moment arm length) whose center is G_entire, and the direction of each of Frf(right leg)x,z and Frf(left leg)x,z is determined in such a way that the direction of the moment (moment around the Y axis) generated around G_entire by each of Frf(right leg)x,z and Frf(left leg)x,z (or the total sum of them) is coincident with the direction of the component L'y around the Y axis of the total rate of change of angular momentum. Then, on that basis, the estimated values (each of which is a pair of the X-axis component value and the Z-axis component value) of Frf(right leg)x,z and Frf(left leg)x,z are calculated in such a way that the total sum of Frf(right leg)x,z and Frf(left leg)x,z (=Frf(right leg)x,z+Frf(left leg)x,z) is coincident with Frf(entire)x,z.

In the single support state, the line of action (the line of action passing through the floor reaction force application point COP of the leg) of the component vector Frf(leg)x,z of the floor reaction force of the leg landing via the foot attachment portion 3 is tangent to the circle Ci having the radius r (moment arm length) whose center is G_entire on the XZ plane, and the direction of Frf(leg)x,z is determined in such a way that the direction of the moment (moment around the Y axis) generated around G_entire by Frf(leg)x,z is coincident with the direction of the component L'y around the Y axis of the total rate of change of angular momentum. Then, on that basis, Frf(leg)x,z of the landing leg is calculated in such a way that the magnitude (absolute value) of Frf(leg)x,z is coincident with the magnitude (absolute value) of Frf(entire)x,z.

As a result, the direction of Frf (the direction of Frf(leg)x,z) on the sagittal plane of the body coordinate system BC can be stabilized in both of the double support state and the single support state.

Frf(leg)x,z calculated in this manner is an estimated value of the component vector on the XZ plane of the floor reaction force acting on the each leg of the person A, supposing that the motion of the person A wearing the support orthosis 1 has been made with the support orthosis 1 removed from the person A. In other words, the floor reaction force Frf(leg)x,z is an estimated value of the component vector on the XZ plane of the floor reaction force kinetically required when the person A makes the same motion as that of the person A wearing the support orthosis 1 independently (without wearing the support orthosis 1).

While the Y-axis component of the floor reaction force Frf(leg) has been set to 0 in this embodiment, it is also possible to determine the direction of the component vector Frf(leg)y,z of the floor reaction force on the YZ plane in such a way that the direction of the component around the X axis of the total rate of change of angular momentum is coincident with the direction of the moment generated around G_entire (the moment around the X axis) by the total sum of the component vector Frf(leg)y,z on the YZ plane of the floor reaction forces of the each leg 2 landing via the foot attachment portion 3, further taking into consideration the component around the X axis of the total rate of change of angular momentum. The direction may be determined by using the moment arm length on the YZ plane and the circle having the radius of the moment arm length, similarly to the above. The direction of Frf(leg)y,z is then determined. Thereafter, in the doubles support state, each coordinate component value of each Frf(leg)y,z may be determined in such a way that the total sum of the component vectors Frf(leg)y,z on the YZ plane of the floor reaction forces acting on the respective legs 2 is coincident with the component vector Frf(entire)y,z on the YZ plane of the total floor reaction force. Moreover, in the single support state, each coordinate component value of Frf(leg)y,z may be determined in such a way that the magnitude of the component vector Frf(leg)y,z on the YZ plane of the floor reaction force acting on the landing leg 2 is coincident with the magnitude of the component vector Frf(entire)y,z on the YZ plane of the total floor reaction force.

The above is the arithmetic processing of the floor reaction force estimation unit 58. Incidentally, to remove noise components from the estimated value of the floor reaction force obtained as stated above, the estimated value filtered may be obtained as an estimated value of the floor reaction force finally. The filtering processing may be, for example, performed by using a second Butterworth filter (low pass filter). The cutoff frequency of the Butterworth filter is preferably in the order of 3 Hz, for example.

Subsequently, the human-side joint moment estimation unit 41 performs the arithmetic processing of the leg plane projection unit 59. In this processing, the acceleration vector ACC(BCO/BC) and the angular velocity vector ω(BCO/BC) of the origin BCO of the body coordinate system BC calculated by the body coordinate system acceleration and angular velocity calculation unit 54, the floor reaction force Frf(right leg/BC) and Frf(left leg/BC) calculated by the floor reaction force estimation unit 58, and the position vector U(COP/BC) of the floor reaction force application point COP calculated by the floor reaction force application point estimation unit 57 are projected to the leg plane PL corresponding to each of the legs S2 for each thereof by using the transformation tensor R(BC→LC) (=R(LC→BC)$^T$), which is a transposition of the transformation tensor R(LC→BC) generated by the transformation tensor generation unit 51.

More specifically, the acceleration vector ACC(BCO/LC) and the angular velocity vector ω(BCO/LC) viewed from the each leg coordinate system LC are obtained by multiplying the acceleration vector ACC(BCO/BC) and the angular velocity vector ω(BCO/BC) each by the transformation tensor R(BC→LC) as shown by the following formulas (12a) and (12b):

$$ACC(BCO/LC)=R(BC{\rightarrow}LC){\times}ACC(BCO/BC) \quad (12a)$$

$$\omega(BCO/LC)=R(BC{\rightarrow}LC){\times}\omega(BCO/BC) \quad (12b)$$

The acceleration vector ACC(BCO/LC) and the angular velocity vector ω(BCO/LC) are each calculated as one corresponding to the leg coordinate system LC of the left leg S2 and one corresponding to the leg coordinate system LC of the right leg S2, individually.

Similarly, the floor reaction force Frf(right leg/right LC) and Frf(left leg/left LC) viewed from the each leg coordinate system LC are obtained by multiplying the floor reaction force vector Frf(right leg/BC) and Frf(left leg/BC) each by the transformation tensor R(BC→right LC) and R(BC→left LC) as shown by the following formulas (12c) and (12d):

$$Frf(\text{right leg/right }LC)=R(BC{\rightarrow}\text{right }LC){\times}Frf(\text{right leg}/BC) \quad (12c)$$

$$Frf(\text{left leg/left }LC)=R(BC{\rightarrow}\text{left }LC){\times}Frf(\text{left leg}/BC) \quad (12d)$$

Moreover, the position vector U(COP/LC) of the floor reaction force application point COP viewed from the leg coordinate system LC corresponding to the landing leg is obtained by multiplying the position vector U(COP/BC) of the floor reaction force application point COP of the landing leg by the transformation tensor R(BC→LC) corresponding to the landing leg as shown by the following formula (12e):

$$U(COP/LC)=R(BC{\rightarrow}LC){\times}U(COP/BC) \quad (12e)$$

In the above, the position vector U(COP/LC) is calculated only for the landing leg in the single support state of the person A, while it is calculated for each of the right and left legs in the double support state.

In this point, regarding the acceleration vector ACC(BCO/LC), the floor reaction forces Frf(right leg/right LC) and Frf(left leg/left LC), and the position vector U(COP/LC) of the floor reaction force application point, a pair of the X coordinate component and the Z coordinate component for each of them are obtained as vectors of two-dimensional quantities obtained by projecting the vectors on the body coordinate system BC (three-dimensional quantities) corresponding to each of them to each leg plane PL (the XZ plane on the leg coordinate system LC). For example, by referring to FIG. 16, it is assumed that the floor reaction force vector Frf(right leg/LC) of the right leg on the body coordinate system BC is a vector as indicated by the shown solid line, the pair of the X coordinate component and the Z coordinate component of the floor reaction force vector Frf(right leg/right LC) is represented by a vector on the leg plane PL(right) as indicated by the dashed line shown in FIG. 16.

A rotary motion of a leg on the leg plane PL is a rotary motion around an axis in the normal line direction (the Y axis direction of the leg coordinate system LC) of the leg plane PL. Therefore, the angular velocity vector ω(BCO/BC) projected to the leg plane PL is a Y coordinate component of the angular velocity vector ω(BCO/LC) on the leg coordinate system LC found by the aforementioned formula (12b).

In the following description of the joint moment calculation unit 60, it is assumed that the acceleration vector ACC(BCO/LC), the floor reaction forces Frf(right leg/right LC) and Frf(left leg/left LC), and the position vector U(COP/LC) of the floor reaction force application point mean two-dimensional vectors each made of the pair of the X axis component and the Z axis component. For example, the acceleration vector ACC(BCO/LC) means (ACC(BCO/LC)x, ACC(BCO/LC)z)$^T$. The value on the leg plane PL of the angular velocity ω is represented by ω(BCO/LC)y.

Subsequently, the human-side joint moment estimation unit 41 performs arithmetic processing of the joint moment calculation unit 60. Describing the outline of the arithmetic processing of the joint moment calculation unit 60, the joint moments of the joint elements J_ankle, J_knee, and J_hip at the endpoints on the waist element S4 side of the foot element S9, the crus element S8, and the thigh element S7 are calculated in order by the operation of the inverse dynamics model based on the equations of motion related to the translational motion and the rotary motion of the foot element S9 (S_foot), the crus element S8 (S_crus), and the thigh element S7 (S_thigh) of the each leg S2. In this instance, the inverse dynamics model is treated on the leg plane PL (the XZ plane of the leg coordinate system LC) corresponding to each of the legs S2 for each thereof. The basic idea of the calculation processing is the same as one suggested by the applicant earlier in Japanese Patent Laid-Open No. 2003-89083 and the like, except the plane and coordinate system where the inverse dynamics model is treated.

Figure 17:
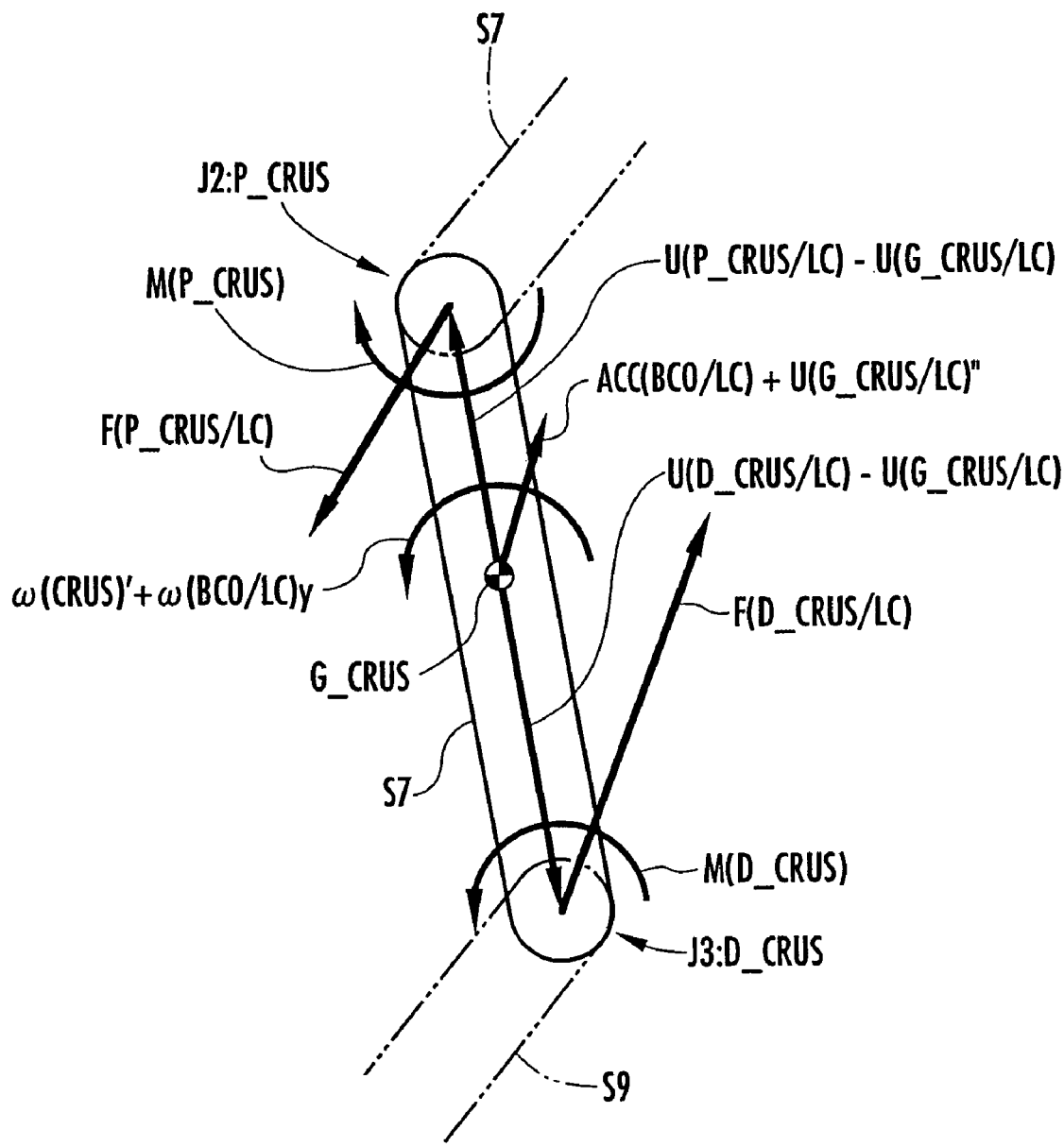
FIG. 17 is a diagram for explaining arithmetic processing using an inverse dynamics model for finding a joint moment.

Explaining in concrete terms hereinafter, the equations of motion of the translational motion on the leg plane PL of the foot element S9, the crus element S8, and the thigh element S7 of the each leg S2 are given by the formulas (15a) to (15c) below. In the following description, one end closer to the waist element S4 is sometimes denoted by "P_□□" and the other end farther from the waist element S4 is sometimes denoted by "D_□□" (□□ is a name of the rigid element) for both ends the rigid elements of the foot element S9, the crus element S8, and the thigh element S7. For example, as shown in FIG. 17, the end of the crus element S8 on the knee joint J_knee (J2) side is denoted by "P_crus" and the other end on the ankle joint J_ankle (J3) side is denoted by "D_crus."

$$F(P\_foot/LC) = m\_foot \times (ACC(BCO/LC) + U(G\_foot/LC)'') - Frf(leg/LC) \quad (15a)$$

$$F(P\_crus/LC) = m\_crus \times (ACC(BCO/LC) + U(G\_crus/LC)'') - F(D\_crus/LC) \quad (15b)$$

$$F(P\_thigh/LC) = m\_thigh \times (ACC(BCO/LC) + U(G\_thigh/LC)'') - F(D\_thigh/LC) \quad (15c)$$

In the above, the two denotations, F(P_□□/LC) and F(D_□□/LC), appearing in the above formulas (15a) to (15c) mean respectively reaction forces (two-dimensional translational force vectors on the leg plane PL) applied by an object put in contact with the ends of the rigid element whose name is represented by □□ to the ends thereof. Therefore, according to the law of action and reaction, F(D_crus/LC)=−F(P_foot/LC) and FD(D_thigh/LC)=−F(P_crus/LC). In the formula (15a) related to the foot element S9, the end farther from the waist element S4 of the foot element S9 is considered to be a floor reaction force application point COP and the floor reaction force Frf(leg/LC) found by the leg plane projection unit 59 is used as a reaction force acting from the floor to the end (the floor reaction force application point COP).

Moreover, U(G_foot/LC)'', U(G_crus/LC)'', and U(G_thigh/LC)'' respectively mean second derivatives of the position vectors of the centers of gravity F_foot, G_crus, and G_thigh (more accurately, the pairs of the X coordinate component and the Z coordinate component of the position vectors) on the leg coordinate system LC previously calculated by the two-dimensional leg posture and element center-of-gravity location calculation unit 52, in other words, relative accelerations (two-dimensional vectors) of the centers of gravity G_foot, G_crus, and G_thigh viewed on the leg plane PL to the origin of the leg coordinate system LC. In this instance, the acceleration vector on the leg plane PL of the origin of the leg coordinate system LC (the center of the hip joint J1) is substantially the same as the acceleration vector ACC(BCO/LC) of the origin of the body coordinate system BC. Therefore, the sum of the acceleration vector ACC(BCO/LC) and U(G_foot/LC)'', U(G_crus/LC)'', or U(G_thigh/LC)'' indicates an actual acceleration vector of the center of gravity G_foot, G_crus, or G_thigh on the leg plane PL.

FIG. 17 typically illustrates a relationship among parameters of the formula (15b) related to the crus element S8.

Accordingly, F(P_foot/LC), namely, the translational force (a two-dimensional vector on the leg plane PL) acting on the ankle joint J_ankle is found by the calculation of the right-hand side of the formula (15a) from the floor reaction force Frf(leg/LC) and the acceleration vector ACC(BCO/LC) obtained by the leg plane projection unit 59, the relative acceleration vector U(G_foot/LC)'' obtained from the time series data of the position vector U(G_foot/LC) of the center of gravity of the foot element S9 found by the two-dimensional leg posture and element center-of-gravity location calculation unit 52, and the weight m_foot of the foot element S9. In addition, F(P_crus/LC), namely, the translational force (a two-dimensional vector on the leg plane PL) acting on the knee joint J_knee is found by the calculation of the right-hand side of the formula (15b) from the found F(P_foot/LC) (=−F(D_crus/LC)), the acceleration vector ACC(BCO/LC) found by the leg plane projection unit 59, the relative acceleration vector U(G_crus/LC)'' obtained from the time series data of the position vector U(G_crus/LC) of the center of gravity of the crus element S8 found by the two-dimensional leg posture and element center-of-gravity location calculation unit 52, and the weight m_crus of the foot element S8. Similarly, F(P_thigh/LC), namely, the translational force (a two-dimensional vector on the leg plane PL) acting on the hip joint J_hip is found by the calculation of the right-hand side of the formula (15c) by using the found F(P_crus/LC) (=−F(D_thigh/LC)) and the like. In this manner, the reaction force vectors (translational vectors) acting on the joint elements J_ankle, J_knee, and J_hip are calculated in order on the basis of the equations of motion in the above (15a) to (15c).

Subsequently, the equations of motion of the rotary motions (rotary motions around an axis passing through the corresponding center of gravity and perpendicular to the leg plane PL) of the foot element S9, the crus element S8, and the thigh element S7 are given by the following formulas (15d) to (15f):

$$M(P\_foot) = I\_foot \times (\omega(foot)' + \omega(BCO/LCy')) - \\ \{(U(COP/LC) - U(G\_foot/LC)) \times Frf(leg/LC)\}y - \\ \{(U(P\_foot/LC) - U(G\_foot/LC)) \times F(P\_foot/LC)\}y \quad (15d)$$

$$M(P\_crus) = I\_crus \times (\omega(crus)' + \omega(BCO/LCy')) - \\ \{(U(D\_crus/LC) - U(G\_crus/LC)) \times F(D\_crus/LC)\}y - \\ \{(U(P\_crus/LC) - U(G\_crus/LC)) \times F(P\_crus/LC)\}y - \\ M(D\_crus) \quad (15e)$$

$$M(P\_thigh) = I\_thigh \times (\omega(thigh)' + \omega(BCO/LCy')) - \\ \{(U(D\_thigh/LC) - U(G\_thigh/LC)) \times F(D\_thigh/LC)\}y - \\ \{(U(P\_thigh/LC) - U(G\_thigh/LC)) \times F(P\_thigh/LC)\}y - \\ M(D\_thigh) \quad (15f)$$

In the above, M(P_□□) and M(D_□□) appearing in the above formulas (15d) to (15f) mean respectively reaction force moments (the moment around the axis perpendicular to the leg plane PL (around the axis parallel to the Y axis of the leg coordinate system LC)) applied by an object put in contact with the ends of the rigid element whose name is represented by □□ to the ends thereof (See FIG. 17). Therefore, according to the law of action and reaction, M(D_crus)=−M(P_foot) and M(D_thigh)=−M(P_crus). Moreover, I_foot, I_crus, and I_thigh are respectively moments of inertia (more specifically, moments of inertia not including the moments of inertia of the support orthosis 1) around the corresponding center of gravity of the foot element S9, the crus element S8, and the thigh element S7 of the human rigid link model S1. They are previously determined based on the measurement data or the like and stored in the memory of the arithmetic processing unit 25 similarly to the weights of the rigid elements of the human rigid link model S1. Furthermore, ω(foot)', ω(crus)', and ω(thigh)' respectively mean first derivatives of the relative angular velocities ω(foot), ω(crus), and ω(thigh) (relative angular velocities around the axis perpendicular to the leg plane PL), in other words, relative angular accelerations, viewed from the leg coordinate system LC of the foot element S9, the crus element S8, and the thigh element S7. These are given as second derivatives of the tilt angles θ_foot, θ_crus, and θ_thigh of the foot element S9, the crus element S8, and the thigh element S7 found by the two-dimensional leg posture and element center-of-gravity location calculation unit 52 as shown by the following formulas (15g) to (15i):

$$\omega(foot)' = \theta\_foot'' \quad (15g)$$

$$\omega(crus)' = \theta\_crus'' \quad (15h)$$

$$\omega(thigh)' = \theta\_thigh'' \quad (15i)$$

In addition, ω(BCO/LC)y' is a first derivative of the actual angular velocity ω(BCO/LC)y of the origin BCO of the body coordinate system BC found by the leg plane projection unit 59. The sum of the first derivative ω(BCO/LC)y' and ω(foot)', ω(crus)', or ω(thigh)' indicates the actual angular acceleration (the angular acceleration around the axis perpendicular to the leg plane PL) of the foot element S9, the crus element S8, or the thigh element S7.

FIG. 17 typically illustrates the relationship among parameters of the formula (15e) related to the crus element S8.

The joint moment calculation unit 60 sequentially calculates joint moments M(P_foot), M(P_crus), and M(P_thigh) finally by using the above formulas (15d) to (15f). More specifically, the joint moment M(P_foot), namely, the moment around the axis perpendicular to the leg plane PL acting on the ankle joint J3 is found by the calculation of the right-hand side of the formula (15d) from the floor reaction force vector Frf(leg/LC) and U(COP/LC) found by the leg plane projection unit 59, the angular acceleration ω(BCO/LC)y' grasped from time series data of the angular velocity ω(BCO/LC)y found by the leg plane projection unit 59, the relative angular acceleration ω(foot)' (=θ_foot'') grasped from the time series data of the tilt angle θ_foot found by the two-dimensional leg posture and element center-of-gravity location calculation unit 52, the position vectors U(G_foot/LC) and U(P_foot/LC) (=U(J_ankle/LC)) (more accurately, the pairs of the X coordinate component and the Z coordinate component of these position vectors) found by the two-dimensional leg posture and element center-of-gravity location calculation unit 52, the reaction force F(P_foot/LC) previously obtained by the formula (15a), and the preset moment of inertia I_foot.

Furthermore, the joint moment N(P_crus), namely, the moment around the axis perpendicular to the leg plane PL acting on the knee joint J2 is found by the calculation of the right-hand side of the formula (15e) from the found joint moment M(P_foot) (=−M(D_crus)), the reaction forces F(P_foot/LC) (=−F(D_crus/LC)) and F(P_crus/LC) previously found by the formulas (15a) and (15b), the angular acceleration ω(BCO/LC)y' grasped from the time series data of the angular velocity ω(BCO/LC)y obtained by the leg plane projection unit 59, the relative angular acceleration ω(crus)' (=θ_crus'') grasped from the time series data of the tilt angle θ_crus found by the two-dimensional leg posture and element center-of-gravity location calculation unit 52, the position vectors U(G_crus/LC), U(P_crus/LC) (=U(J_knee/LC)), and U(D_crus/LC) (=U(J_ankle/LC)) (more accurately, the pairs of the X coordinate component and the Z coordinate component of these position vectors) found by the two-dimensional leg posture and element center-of-gravity location calculation unit 52, and the preset moment of inertia I_crus. Similarly, M(P_thigh), namely, the moment around the axis perpendicular to the leg plane PL acting on the hip joint J1 is found by the calculation of the right-hand side of the formula (15e) by using the found M(P_crus) (=−M(D_thigh)) and the like.

While the moments of inertia I_foot, I_crus, and I_thigh of the rigid elements of the each leg S2 have been considered in this embodiment, these values are sufficiently close to zero in general. Therefore, the terms including the moment of inertia I_foot, I_crus, or I_thigh may be omitted in the calculations of the formulas (15d) to 15(f). If they are omitted, there is no need to grasp the angular velocities or angular accelerations of the foot element S9, the crus element S8, and the thigh element S7.

As described above, in the arithmetic processing of the joint moment calculation unit 60, the moments of inertia M(P_foot), M(P_crus), and M(P_thigh) around the axis perpendicular to the leg plane PL of the ankle joint, the knee joint, and the hip joint of the each leg of the person A are calculated in order from the ankle joint side. These joint moments M(P_foot), M(P_crus), and M(P_thigh) are moments to be generated at the ankle joint, the knee joint, and the hip joint of the each leg supposing that the motion of the person A wearing the support orthosis 1 is performed without the support orthosis 1 (performed by the person A without help). In other words, the joint moments can satisfy the required kinetic relation (physical law) between the motion of the person A and the external force (floor reaction force) and the gravity force acting on the person A when it is considered that the support orthosis 1 is not put on the person A.

Subsequently, the arithmetic processing of the orthosis-side joint moment estimation unit 42 is described below. The arithmetic processing of the orthosis-side joint moment estimation unit 42 is sequentially performed for each processing period of the arithmetic processing unit 25 in parallel with the arithmetic processing of the human-side joint moment estimation unit 41. The basic method of the arithmetic processing is the same as the arithmetic processing of the human-side joint moment estimation unit 41. Therefore, the following description will focus on different points from the arithmetic processing of the human-side joint moment estimation unit 41. In the following description until the end of the description of the arithmetic processing of the orthosis-side joint moment estimation unit 42, the rigid element, the joint element, the leg coordinate system, and the element coordinate system are assumed to mean the rigid element, the joint element, the leg coordinate system, and the element coordinate system of the orthosis rigid link model S1', respectively, unless otherwise specified.

In the arithmetic processing of the orthosis-side joint moment estimation unit 42, the two-dimensional leg posture and element center-of-gravity location calculation unit 61 performs arithmetic processing, first. The arithmetic processing is the same as that of the two-dimensional leg posture and element center-of-gravity location calculation unit 52 of the human-side joint moment estimation unit 41. More specifically, the tilt angles θ_thigh orthosis, θ_crus orthosis, and θ_foot orthosis of the thigh element S7 (S_thigh orthosis), the crus element S((S_crus orthosis), and the foot element S9 (S_foot orthosis) of the orthosis rigid link model S1' are calculated, respectively, (See FIG. 9) by using the rotation angles θ_hip orthosis, θ_knee orthosis, and θ_ankle orthosis (the rotation angles around the axis perpendicular to the leg plane PL. See FIG. 9) of the hip joint region 7, the knee joint region 9, and the ankle joint region 11 of the each leg link portion 4, which are grasped from the detected outputs of the joint displacement sensors 31 to 33 of the each leg link portion 4. The tilt angles θ_thigh orthosis, θ_crus orthosis, and θ_foot orthosis are tilt angles relative to the Z axis of the leg coordinate system LC.

In this instance, θ_thigh orthosis, θ_crus orthosis, and θ_foot orthosis are directly calculated from the detected values of θ_hip orthosis, θ_knee orthosis, and θ_ankle orthosis by the following formulas (101d) to (101f), which are similar to the aforementioned formulas (1d) to (1f):

$$\theta\_thigh\ orthosis = -\theta\_hip\ orthosis \quad (101d)$$

$$\theta\_crus\ orthosis = \theta\_thigh\ orthosis + \theta\_knee\ orthosis \quad (101e)$$

$$\theta\_foot\ orthosis = \theta\_crus\ orthosis - \theta\_ankle\ orthosis + (\pi/2) \quad (101f)$$

The θ_thigh orthosis, θ_crus orthosis, and θ_foot orthosis are calculated for each of the legs S2 individually.

In the arithmetic processing of the two-dimensional leg posture and element center-of-gravity location calculation unit 61, subsequently the positions on the XZ plane of the leg coordinate system LC (it is also the position viewed on the leg plane PL) of the joint elements of the each leg S2 are calculated by using the tilt angles θ_thigh orthosis and θ_crus orthosis calculated as described above. More specifically, the position vectors U(J_hip orthosis/LC), U(J_knee orthosis/LC), and U(J_ankle orthosis/LC) on the leg coordinate system LC of the joint elements J_hip orthosis, J_knee orthosis, and J_ankle orthosis of the each leg S2 are sequentially calculated by the following formulas (102a) to (192c), which are similar to the aforementioned formulas (2a) to (2c):

$$U(J\_hip\ orthosis/LC) = (0, 0, 0)^T \quad (102a)$$

$$U(J\_knee\ orthosis/LC) = U(J\_hip\ orthosis/LC) + (-L7s \times \sin(\theta\_thigh\ orthosis), 0, -L7s \times \cos(\theta\_thigh))^T \quad (102b)$$

$$U(J\_ankle\ orthosis/LC) = U(J\_knee\ orthosis/LC) + (-L8s \times \sin(\theta\_crus\ orthosis), 0, -L8s \times \cos(\theta\_crus\ orthosis))^T \quad (102c)$$

In the above, L7s and L8s in the formulas (102b) and (102c) are the lengths of the S_thigh orthosis and S_crus orthosis, respectively (see FIG. 9). The Y-axis components of the position vectors U(J_hip orthosis/LC), U(J_knee orthosis/LC), and U(J_ankle orthosis/LC) found by the formulas (102a) to (102c) are assumed to be zero. Thus, the pair of the X-axis component and the Z-axis component indicates the two-dimensional position on the XZ plane (or the leg plane PL) of the leg coordinate system LC. In addition, U(J_hip orthosis/LC) and U(J_ankle orthosis/LC) are the same as U(J_hip/LC) and U(J_ankle/LC) found by the aforementioned formulas (2a) and (2c) by the two-dimensional leg posture and element center-of-gravity location calculation unit 52 of the human-side joint moment estimation unit 41, respectively, in this embodiment. Therefore, these U(J_hip/LC) and U(J_ankle/LC) may be directly determined to be U(J_hip orthosis/LC) and U(J_ankle orthosis/LC), respectively.

In the arithmetic processing of the two-dimensional leg posture and element center-of-gravity location calculation unit 61, the position vectors on the leg coordinate system LC of the centers of gravity of the rigid elements (the rigid elements of the leg S2) of the orthosis rigid link model S1' by using the position vectors U(J_hip orthosis/LC), U(J_knee orthosis/LC), and U(J_ankle orthosis/LC) calculated as described above.

More specifically, the position vectors U(G_thigh orthosis/LC), U(G_crus orthosis/LC), and U(G_foot orthosis/LC) of the centers of gravity G_thigh orthosis (G7), G_crus orthosis (G8), and G_foot orthosis (G9) of the thigh element S7, the crus element S8, and the foot element S9 are calculated by the formulas (103a) to (103c), which are similar to the aforementioned formulas (3a) to (3c):

$$U(G\_thigh\ orthosis/LC) = \\ U(J\_knee\ orthosis/LC) + R(C\_thigh\ orthosis \rightarrow LC) \times \\ U(G\_thigh\ orthosis/C\_thigh\ orthosis) \quad (103a)$$

$$U(G\_crus\ orthosis/LC) = U(J\_ankle\ orthosis/LC) + \\ R(C\_crus\ orthosis \rightarrow LC) \times U(G\_crus\ orthosis/C\_crus\ orthosis) \quad (103b)$$

$$U(G\_foot\ orthosis/LC) = U(J\_MP/LC) + \\ R(C\_foot\ orthosis \rightarrow LC) \times U(G\_foot\ orthosis/C\_foot\ orthosis) \quad (103c)$$

In the formulas (103a) to (103c), the transformation tensors R(C_thigh orthosis→LC), R(C_crus orthosis→LC), and R(C_foot orthosis→LC) are determined by using the previously calculated θ_thigh orthosis, θ_crus orthosis, and θ_foot orthosis, respectively. In addition, U(G_thigh orthosis/C_thigh orthosis), U(G_crus orthosis/C_crus orthosis), and U(G_foot orthosis/C_foot orthosis) are position vectors of the centers of gravity of the rigid elements represented on the element coordinate system of the corresponding rigid elements, and they are previously stored in the memory of the arithmetic processing unit 25. In this embodiment, the element coordinate system C_foot orthosis of the orthosis rigid link model S1' is the same as the element coordinate system C_foot of the human rigid link model S1 and is the coordinate system whose origin is MP joint J4. Therefore, for U(J_MP/LC) in the formula (103c), it is possible to directly use the value of U(J_MP/LC) calculated by the aforementioned formula (2d) in the two-dimensional leg posture and element center-of-gravity location calculation unit 52 of the human-side joint moment estimation unit 41.

The pairs of the X-axis component and the Z-axis component of the position vectors U(G_thigh orthosis/LC), U(G_crus orthosis/LC), and U(G_ankle orthosis/LC) calculated by the aforementioned formulas (103a) to (103c) represent the two-dimensional positions on the leg plane PL (on the XZ plane of the leg coordinate system LC).

Moreover, in the arithmetic processing of the two-dimensional leg posture and element center-of-gravity location calculation unit 61, the position vectors on the leg coordinate system LC of the bottom edges of the support members S9b, S9c (see the above FIG. 5) of the foot element S9 are also calculated. Here, the support member S9b on the front side is referred to as the front support member S9b and the support member S9c on the back side is referred to as the back support member S9c regarding the support members S9b, S9c of the each foot element S9, assuming that the position vectors (position vectors on the leg coordinate system LC) at the bottom edges are U(front support member/LC) and U(back support member/LC). In this condition, U(front support member/LC) and U(back support member/LC) are each calculated by a formula in which U(G_foot orthosis/C_foot orthosis) in the right-hand side of the above formula (103c) is replaced with U(front support member/C_foot orthosis) or U(back support member/C_foot orthosis). U(front support member/C_foot orthosis) and U(back support member/C_foot orthosis) are position vectors of the front support member S9b and the back support member S9c in the element coordinate system C_foot orthosis of the each foot element S9 and are previously stored in the memory of the arithmetic processing unit 25.

Subsequently, the orthosis-side joint moment estimation unit 42 performs the arithmetic processing of the three-dimensional joint and element center-of-gravity location calculation unit 62 to find the position vectors on the body coordinate system BC of the centers of gravity of the joint elements and the rigid elements of the orthosis rigid link model S1'. This arithmetic processing is performed in the same manner as for finding the three-dimensional position vectors of the centers of gravity of the joint elements and the rigid elements of the human rigid link model S1 in the three-dimensional joint and element center-of-gravity location calculation unit 53 of the human-side joint moment estimation unit 41. More specifically, for example, the position vectors U(J_left hip orthosis/BC), U(J_left knee orthosis/BC), and U(J_left ankle orthosis/BC) of the joint elements J1, J2, and J3 of the left leg S2 are calculated in order by the following formulas (104a) to (104c), which are similar to the aforementioned formulas (4a) to (4c):

$$U(J\_left\ hip\ orthosis/BC)=(0, L4sa/2, 0)^T \quad (104a)$$

$$U(J\_left\ knee\ orthosis/BC)=U(J\_left\ hip\ orthosis/BC)+R(LC \rightarrow BC) \times U(J\_left\ knee\ orthosis/LC) \quad (104b)$$

$$U(J\_left\ ankle\ orthosis/BC)=U(J\_left\ hip\ orthosis/BC)+R(LC \rightarrow BC) \times U(J\_left\ ankle\ orthosis/LC) \quad (104c)$$

In the above, L4sa in the formula (104a) is the length of the line segment between the centers of both hip joints J1, J1 of the waist element S4 (the length of the line segment connecting the centers of the both hip joint regions 7, 7 of the support orthosis 1). In addition, the transformation tensor R(LC→BC) in the formulas (194b) and (104c) are found by the transformation tensor generation unit 51 of the human-side joint moment estimation unit 41. In other words, in this embodiment, the coordinate axes of the left leg coordinate system LC of the orthosis rigid link model S1' are set in the same directions of the coordinate axes of the left leg coordinate system LC of the human rigid link model S1. The same applies to the right leg coordinate system. Therefore, the transformation tensor R(LC→BC) from each leg coordinate system LC to the body coordinate system BC of the human rigid link model S1 is the same as the transformation tensor R(LC→BC) from each leg coordinate system LC to the body coordinate system BC of the orthosis rigid link model S1'. Furthermore, U(J_left knee orthosis/LC) and U(J_left ankle orthosis/LC) in the formulas (104b) and (194c) are previously found by the aforementioned formulas (102b) and (102c), respectively.

In this embodiment, the position vectors U(JU1/BC) and U(JU2/BC) on the body coordinate system BC of the lower joint of the upper body JU1 and the upper joint of the upper body JU2 of the orthosis rigid link model S1' are assumed to be the same as those calculated by the three-dimensional joint and element center-of-gravity location calculation unit 53 of the human-side joint moment estimation unit 41.

Moreover, the position vectors U(G_thigh orthosis/BC), U(G_crus orthosis/BC), and U(G_foot orthosis/BC) on the body coordinate system BC of the centers of gravity of the thigh element S7, the crus element S8, and the foot element S9 are found by calculating the formulas in which U(J_left knee orthosis/LC) in the right-hand side of the formula (104b) is replaced with the position vectors U(G_thigh orthosis/LC), U(G_crus orthosis/LC), and U(G_foot orthosis/LC) of the centers of gravity previously calculated by the two-dimensional leg posture and element center-of-gravity location calculation unit 61, respectively. The position vectors on the body coordinate system BC of G_thigh orthosis, G_crus orthosis, and G_foot orthosis are calculated for each of the legs S2 separately.

In addition, the position vector U(G_waist orthosis/BC) of the center of gravity G4 of the waist element S4 is calculated by the formula in which U(G_waist/C_waist) in the right-hand side of the aforementioned formula (4g) is replaced with the position vector U(G_waist orthosis/C_waist orthosis) of the center of gravity G_waist orthosis on the waist coordinate system C_waist orthosis (=C_waist) previously stored. In this embodiment, C_waist orthosis is equal to the body coordinate system BC, and therefore U(G_waist orthosis/C_waist orthosis) is directly obtained as U(G_waist orthosis/BC) in fact.

Moreover, in this embodiment, the position vectors U(G_abdomen orthosis/BC) and U(G_chest orthosis/BC) on the body coordinate system BC of the centers of gravity G5 and G6 of the abdomen element S5 and the chest element S6 of the orthosis rigid link model S1' are calculated by the formulas in which U(G_abdomen/C_abdomen) and U(G_chest/C_chest) in the right-hand side of the aforementioned formulas (4h) and (4i) are replaced with U(G_abdomen orthosis/C_abdomen) and U(G_chest orthosis/C_chest) (they are previously stored in the arithmetic processing unit 25), respectively. Incidentally, C_abdomen=C_abdomen orthosis and C_chest=C_chest orthosis in this embodiment.

In this embodiment, the weights of the abdomen element S5 and the chest element S6 of the orthosis rigid link model S1' are sufficiently low, and therefore these elements hardly have any influence on the entire center of gravity or the entire angular momentum of the orthosis rigid link model S1'. Thus, the calculation of the position vectors U(G_abdomen orthosis/BC) and U(G_chest orthosis/BC) may be omitted.

Moreover, in the arithmetic processing of the three-dimensional joint and element center-of-gravity location calculation unit 62, the position vectors U(front support member/BC) and U(back support member/BC) on the body coordinate system BC of the front support member S9b and the back support member S9c of the each foot element S9 are also calculated for each of the legs S2 separately. These position vectors U(front support member/BC) and U(back support member/BC) are found by calculating the formulas in which U(J_left knee orthosis/LC) in the right-hand side of the aforementioned formula (104b) is replaced with the position vectors U(front support member/LC) and U(back support member/LC) of the front support member S9b and the back support member S9c of the each foot element S9 previously calculated by the two-dimensional leg posture and element center-of-gravity location calculation unit 61.

Subsequently, the orthosis-side joint moment estimation unit 42 performs the arithmetic processing of the entire center-of-gravity location calculation unit 63. In the arithmetic processing of the entire center-of-gravity location calculation unit 63, the position vector U(G_entire orthosis/BC) on the body coordinate system BC of the entire center of gravity (the entire center of gravity of the support orthosis 1. Hereinafter, sometimes referred to as G_entire orthosis) of the orthosis rigid link model S1' is found from the center of gravity locations (the position vectors on the body coordinate system BC) of the rigid elements calculated by the three-dimensional joint and element center-of-gravity location calculation unit 62 and the weights of the rigid elements of the orthosis rigid link model S1' previously stored in the arithmetic processing unit 25, by using the following formula (106) similar to the aforementioned formula (6):

$$U(G\_entire\ orthosis/BC) = \quad (106)$$
$$\{U(G\_chest\ orthosis/BC) \times m\_chest\ orthosis +$$
$$U(G\_abdomen\ orthosis/BC) \times m\_abdomen\ orthosis +$$
$$U(G\_waist\ orthosis/BC) \times m\_waist\ orthosis +$$

-continued $U(\text{G\_right thigh orthosis}/BC) \times \text{m\_right thigh orthosis} +$ $U(\text{G\_left thigh orthosis}/BC) \times \text{m\_left thigh orthosis} +$ $U(\text{G\_right crus orthosis}/BC) \times \text{m\_right crus orthosis} +$ $U(\text{G\_left crus orthosis}/BC) \times \text{m\_left crus orthosis} +$ $U(\text{G\_right foot orthosis}/BC) \times \text{m\_right foot orthosis} +$ $U(\text{G\_left foot orthosis}/BC) \times \text{m\_left foot orthosis}\} /$ orthosis' entire weight The term "m_□□ orthosis" such as m_chest orthosis is a weight of a rigid element of the orthosis rigid link model S1' corresponding to the name of □□ and thus it is the weight of a single unit of the support orthosis 1 (not including the weight of the person A). As shown by the formula (6). Moreover, m_chest orthosis and m_abdomen orthosis are each approximately zero in this embodiment, and therefore the terms including them may be omitted.

Subsequently, the orthosis-side joint moment estimation unit 42 performs the arithmetic processing of the floor reaction force application point estimation unit 64 and of the floor reaction force estimation unit 65. In the arithmetic processing of the floor reaction force application point estimation unit 64, the application points of the floor reaction force Frf(right leg orthosis/BC) and Frf(left leg orthosis/BC) acting on the support orthosis 1 are estimated by using the same method as the floor reaction force application joint estimation unit 57 of the human-side joint moment estimation unit 41.

In this instance, the position vector U(orthosis COP/BC) of the floor reaction force application point COP of the support orthosis 1 is estimated based on the positional relation on the horizontal plane between the center of gravity of the entire orthosis and the front support member S9b and the back support member S9c of the foot element S9 of the landing leg on the absolute coordinate system IC.

More specifically, first, the position vectors U(G_entire orthosis/IC), U(front support member/IC), and U(back support member/IC) viewed on the absolute coordinate system IC of G_entire orthosis and the front support member S9b and the back support member S9c of the each foot element S9 are calculated by multiplying the position vector U(G_entire orthosis/BC) of the entire center of gravity of the orthosis previously calculated by the entire center-of-gravity location calculation unit 63 and the position vectors U(front support member/BC) and U(back support member/BC) of the front support member S9b and the back support member S9c of the each foot element S9 previously calculated by the three-dimensional joint and element center-of-gravity location calculation unit 62 by the aforementioned transformation tensor R(BC→IC), respectively, by using the transformation tensor R(BC→IC) found by the floor reaction force application point estimation unit 57 of the human-side joint moment estimation unit 41. Regarding the leg determined to be not in contact with the ground from detected outputs of the landing sensors 34 and 35 at that point, there is no need to calculate the position vector U(front support member/IC) nor U(back support member/IC).

Subsequently, the X-axis component and the Y-axis component of the position vector (the position vector on the absolute coordinate system IC) of the floor reaction force application point U(orthosis COP/IC) are determined according to the magnitude relation among the X-axis components U(G_entire orthosis/IC)x, U(front support member/IC)x, and U(back support member/IC)x of the position vectors U(G_entire orthosis/IC), U(front support member/IC), and U(back support member/IC), in other words, according to the relative horizontal positional relationship in the forward/backward direction among the entire center of gravity of the orthosis, the front support member S9b and the back support member S9c of the foot element S9 for the each leg determined to be in contact with the ground from detected outputs of the landing sensors 34 and 35.

Figure 18:
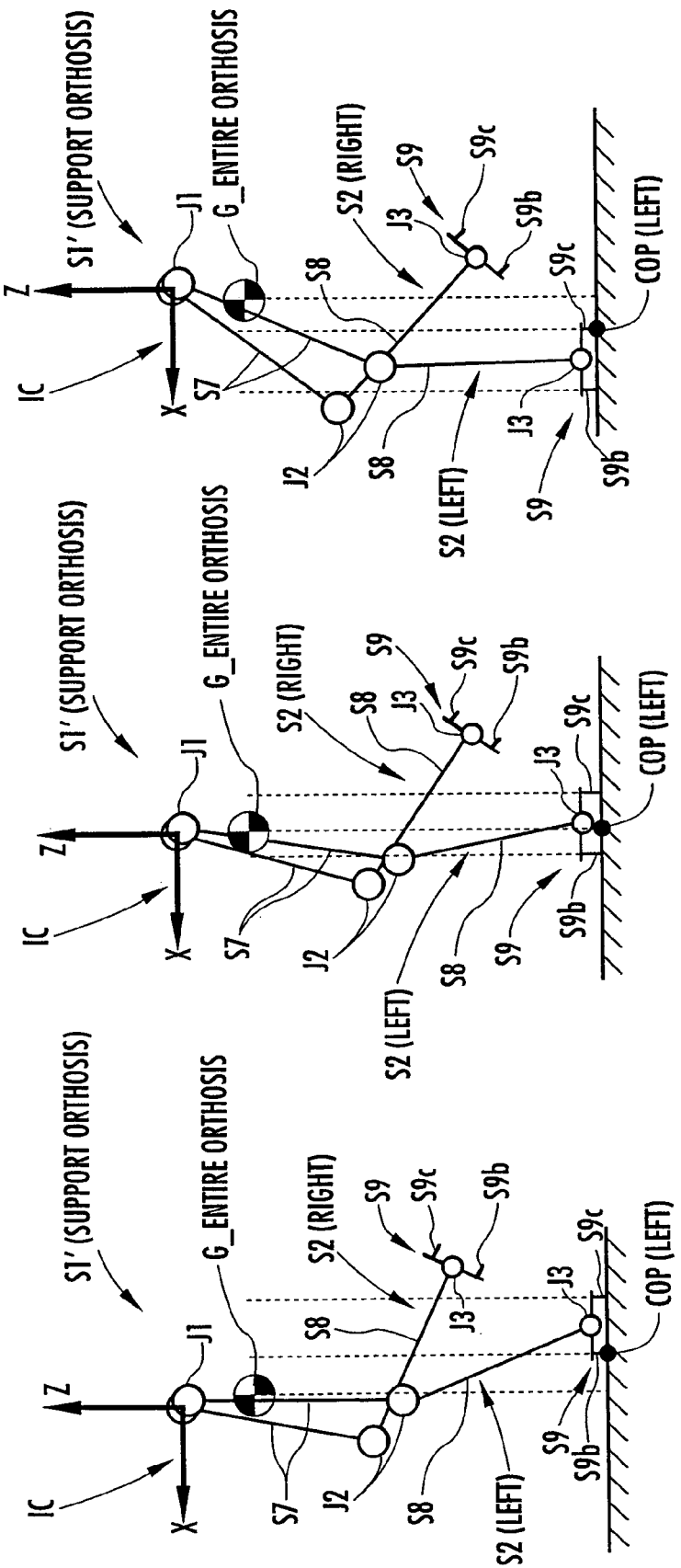
FIGS. 18($a$) to 18($c$) are diagrams for explaining methods of estimating a floor reaction force application point on the corresponding sagittal plane of the leg motion support orthosis.
Figure 19:
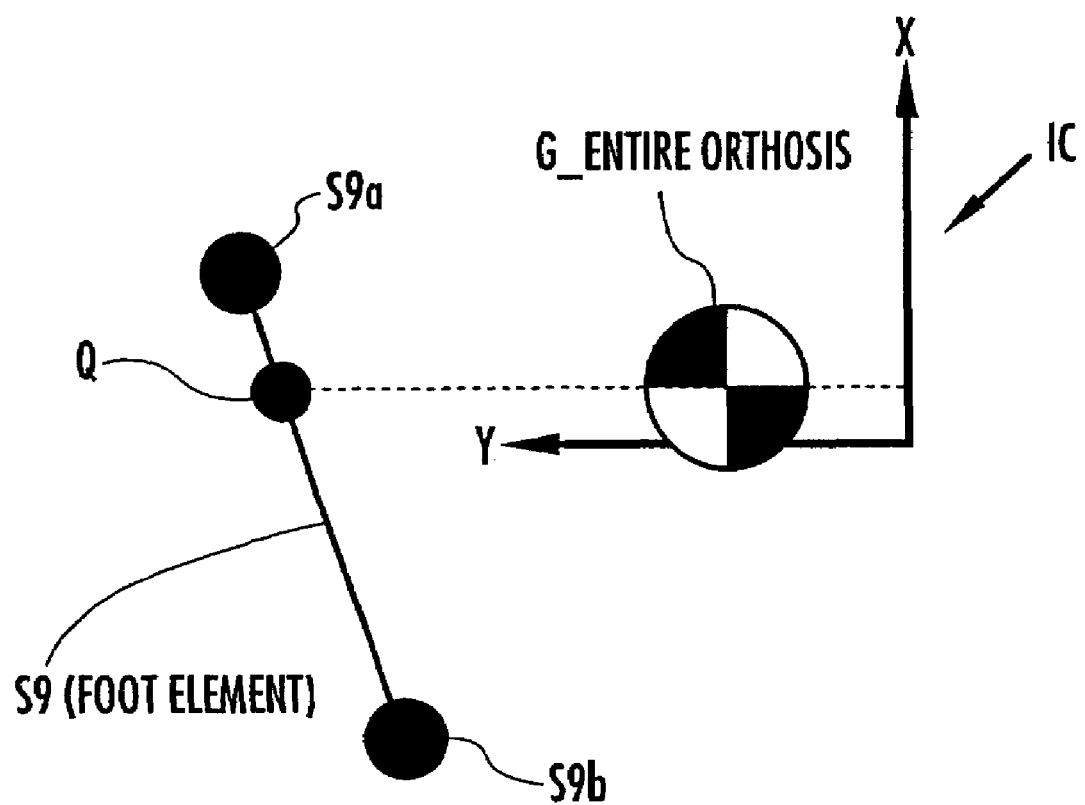
FIG. 19 is a diagram for explaining a method of estimating a floor reaction force application point on the horizontal plane of the leg motion support orthosis.

The above is described more specifically with reference to FIGS. 18(a) to 18(c) and FIG. 19. In the following description, it is assumed that the left foot attachment portion 3 of the support orthosis 1 is landing. FIGS. 18(a) to 18(c) illustrate the conditions where the left foot attachment portion 3 of the support orthosis 1 is in contact with the ground (the single support state in these diagrams), viewed on the sagittal plane (XZ plane) of the absolute coordinate system IC. FIG. 19 shows a plan view of the foot attachment portion 3 on the landing side of the support orthosis 1 in the condition shown in FIG. 18(b). In FIG. 18 and FIG. 19, the leg link portion 4 and the foot attachment portion 3 of the support orthosis 1 are typified and shown by the elements of the orthosis rigid link model S1'.

As shown in FIG. 18(a), if the entire center of the orthosis G_entire orthosis is more forward than the front support member S9b of the left foot element S9 (left foot attachment portion 3) on the landing side, in other words, if U(G_entire orthosis/IC)x>U(left front support member/IC)x, the floor reaction force application point COP exists substantially just under the front support member S9b of the left foot element S9. Therefore, in this instance, the X- and Y-axis components of the position vector U(left orthosis COP/IC) of the floor reaction force application point COP corresponding to the landing left foot element S9 are assumed to be equal to the X- and Y-axis components of the position vector U(left front support member/IC) of the front support member S9b of the left foot element S9, respectively. In other words, it is assumed that the following equations are satisfied: U(left orthosis COP/IC)x=U(left front support member/IC)x and U(left orthosis COP/IC)y=U(left front support member/IC)y.

Moreover, as shown in FIG. 18(c), if the entire center of the orthosis G_entire orthosis is more backward than the back support member S9c of the left foot element S9 (left foot attachment portion 3) on the landing side, in other words, if U(G_entire orthosis/IC)x<U(left back support member/IC)x, the floor reaction force application point COP exists substantially just under the back support member S9c (the heel of the foot attachment portion 3) of the left foot element S9. Therefore, in this instance, the X- and Y-axis components of the position vector U(left orthosis COP/IC) of the floor reaction force application point COP corresponding to the landing left foot element S9 are assumed to be equal to the X- and Y-axis components of the position vector U(left back support member/IC) of the back support member S9c of the left foot element S9, respectively. In other words, it is assumed that the following equations are satisfied: U(left orthosis COP/IC)x=U(left back support member/IC)x and U(left orthosis COP/IC)y=U(left back support member/IC)y.

Moreover, as shown in FIG. 18(b), if the entire center of the orthosis G_entire orthosis is between the front support member S9b and the back support member S9c of the left foot element S9 (left foot attachment portion 3), in other words, if U(left front support member/IC)x≦U(G_entire orthosis/IC)≦U(left back support member/IC)x, the floor reaction force application point COP exists substantially just under the entire center of gravity of the orthosis G_entire orthosis on the shown sagittal plane. Therefore, in this instance, the X-axis component of the position vector U(left orthosis COP/IC) of the floor reaction force application point COP corresponding to the landing left foot element S9 is assumed to be equal to the X-axis component of the entire center of gravity of the orthosis G_entire orthosis. In other words, it is assumed that the following equation is satisfied: U(left orthosis COP/IC) x=U(G_entire orthosis/IC)x. Then, it is considered that the position of the floor reaction force application point COP is almost on the line segment obtained by projecting the line segment between the front support member S9b and the back support member S9c of the left foot element S9 onto the floor surface. Therefore, the Y-axis component of the position vector U(left orthosis COP/IC) of the floor reaction force application point COP is assumed to be equal to the Y-axis component of the point Q whose X-axis component (the X-axis component on the absolute coordinate system IC) value is the same as that of the entire center of gravity of the orthosis G_entire orthosis on the line segment between the front support member S9b and the back support member S9c of the left foot element S9, as shown in FIG. 19. The value of the Y-axis component of the position vector U(left orthosis COP/IC) is found based on the following formula (107) indicating the proportional relation. The formula (107) corresponds to the aforementioned formula (7).

$$U(\text{left orthosis } COP/IC)x - U(\text{J\_left back support member}/IC) \quad (107)$$
$$x : U(\text{J\_left front support member}/IC)x -$$
$$U(\text{J\_left back support member}/IC)x =$$
$$U(\text{left orthosis } COP/IC)y - U(\text{J\_left back support member}/IC)y : U(\text{J\_left front support member}/IC)y -$$
$$U(\text{J\_left back support member}/IC)y$$

Moreover, it is assumed that the Z-axis component of the position vector U(left orthosis COP/IC) of the floor reaction force application point is equal to the Z-axis component of the point that is a predetermined value H0 (>0) away from the ankle joint J3 of the left leg S2 (left leg link portion 4) downward in the vertical direction, similarly to the floor reaction force application point estimation unit 57 of the human-side joint moment estimation unit 41. In other words, it is assumed that U(left COP/IC)z=U(J_left ankle orthosis/IC)z−H0. In this regard, the predetermined value H0 is the same as one for use in the floor reaction force application point estimation unit 57 of the human-side joint moment estimation unit 41 in this embodiment.

In this embodiment, if the left foot attachment portion 3 of the support orthosis 1 is landing, the position vector U(left orthosis COP/IC) of the floor reaction force application point, which is the application point of the floor reaction force acting on the left link portion 4 (left leg S2) of the support orthosis 1, is calculated as described above. The same applies to the condition where the right foot attachment portion 3 of the support orthosis 1 is landing. In this instance, the position vector of the floor reaction force application point is calculated as described above for each of the legs S2 in the double support state.

In this embodiment, the predetermined value H0 for use in finding the Z-axis component of the position vector U(orthosis COP/IC) of the floor reaction force application point has been assumed to be a fixed value. If it is found, however, that only the tip side of the foot attachment portion 3 is in contact with the ground by means of the landing sensors 34 and 35, it is also possible to use the difference between the Z-axis components of the position vectors U(J_ankle/IC) and U(front support member/IC) of the ankle joint J3 and the front support member S9b (U(J_ankle/IC)z−U(front support member/IC)z), in other words, the distance in the vertical direction between the ankle joint J3 and the front support member S9b, instead of the predetermined value H0, regarding the landing foot attachment portion 3. This improves the accuracy of U(orthosis COP/IC).

In the arithmetic processing of the floor reaction force application point estimation unit 64, the value U(COP/BC) on the body coordinate system BC of the position vector of the floor reaction force application point related to the support orthosis is found finally by multiplying the position vector U(orthosis COP/IC) of the floor reaction force application point obtained for the landing leg link portion 4 as described above by the transformation tensor R(IC→BC).

Figure 20:
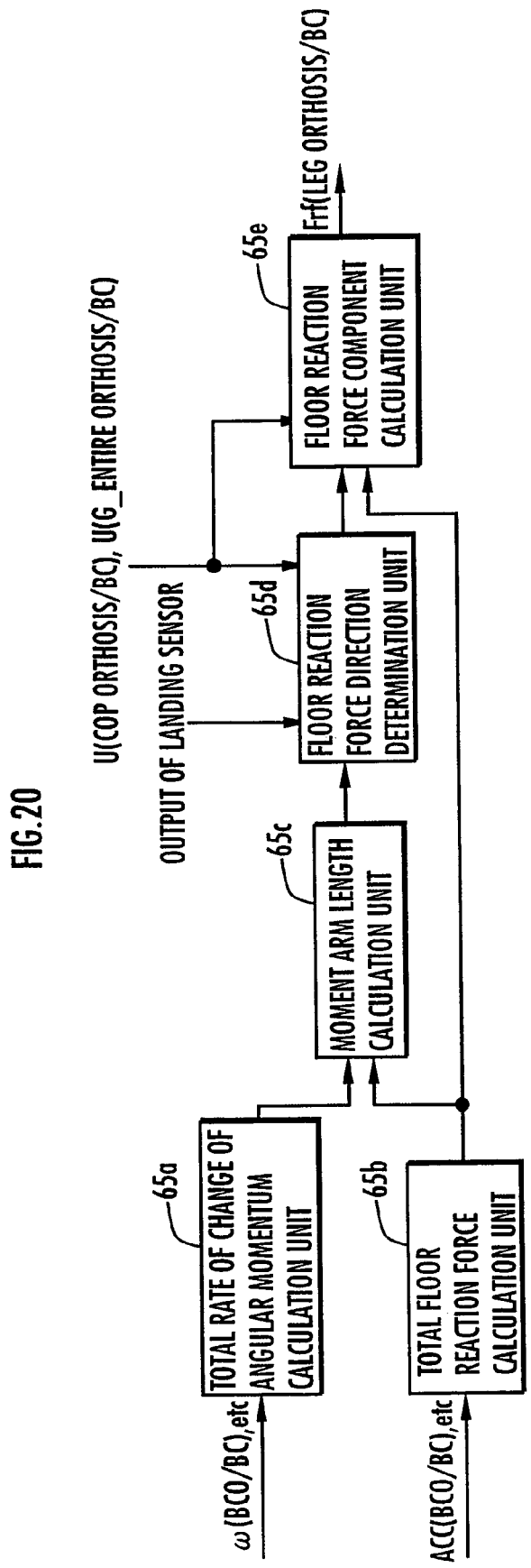
FIG. 20 is a block diagram showing an arithmetic processing function of the floor reaction force estimation unit shown in FIG. 8.
Figure 21:
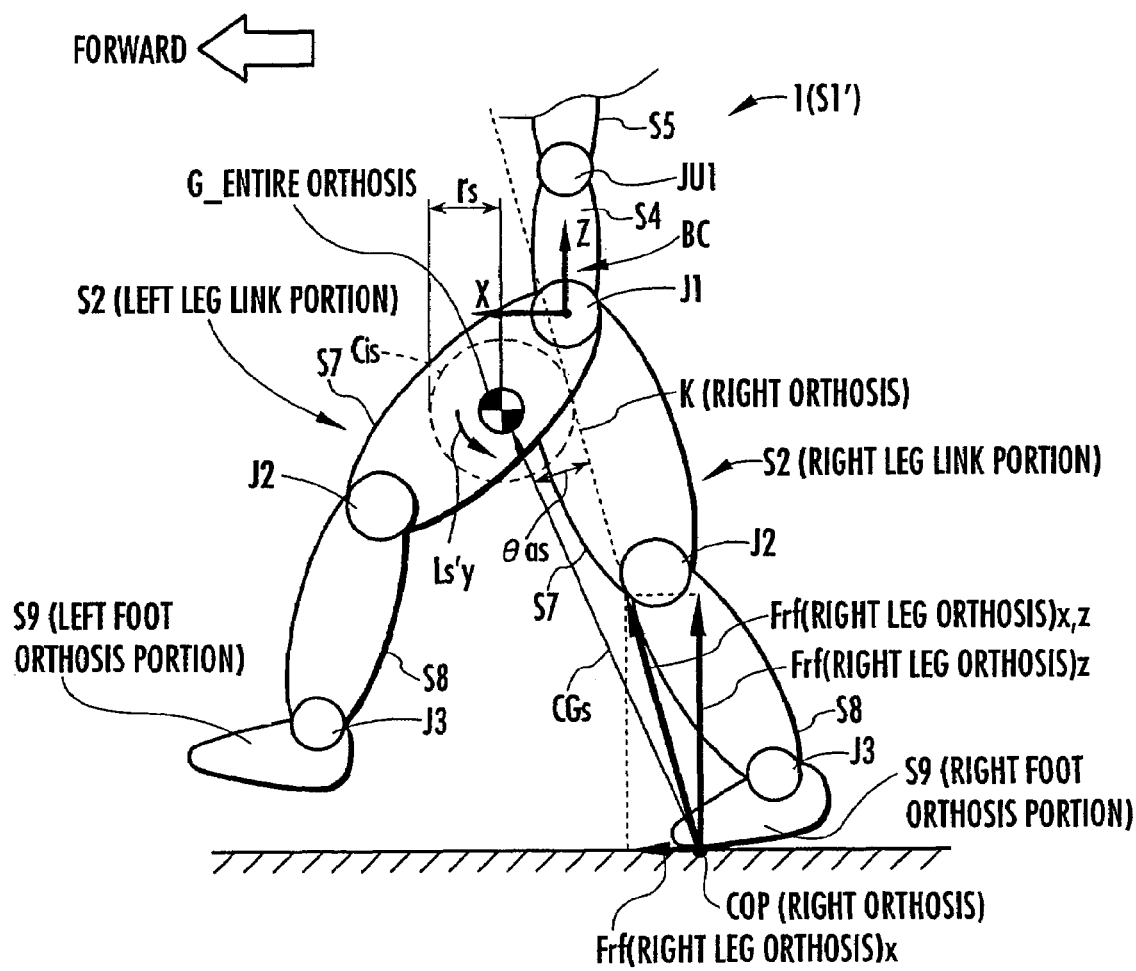
FIG. 21 is a diagram for explaining a method of estimating a floor reaction force in the single support state of the leg motion support orthosis.
Figure 22:
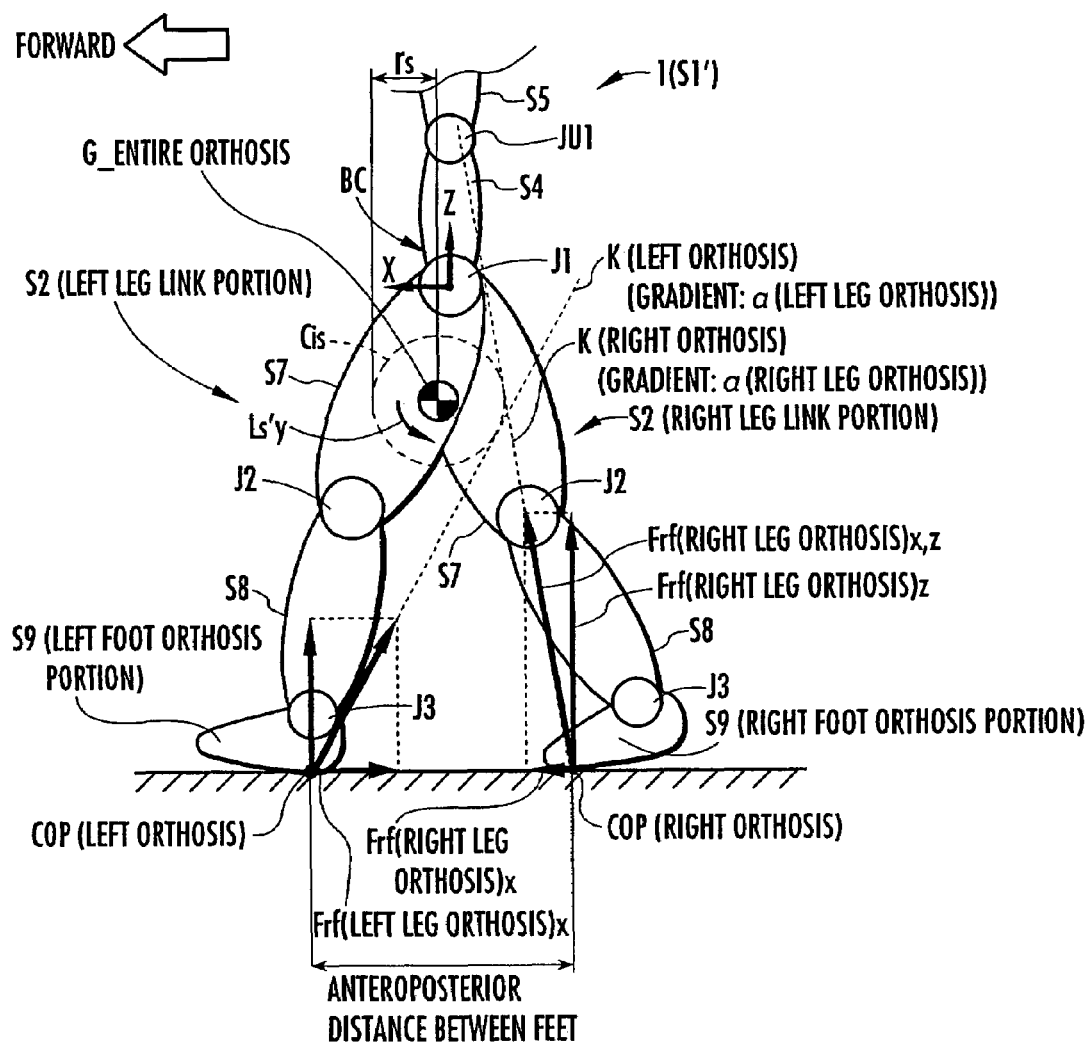
FIG. 22 is a diagram for explaining a method of estimating floor reaction forces in the double support state of the leg motion support orthosis.

In the arithmetic processing of the floor reaction force estimation unit 65, the floor reaction force (the floor reaction force viewed on the body coordinate system BC) acting on the support orthosis 1 is estimated by the same method as for the floor reaction force estimation unit 58 of the human-side joint moment estimation unit 41. Hereinafter, the arithmetic processing of the floor reaction force estimation unit 65 will be described with reference to FIG. 20 to FIG. 22. FIG. 20 is a block diagram showing the arithmetic processing functions of the floor reaction force estimation unit 65. FIG. 21 and FIG. 22 typically show the support orthosis 1 in the single support state and in the double support state, respectively, by using the orthosis rigid link model S1'. In FIG. 21 and FIG. 22, the rigid elements of the orthosis rigid link model S1' are allowed to have more latitude. Furthermore, in the description of the floor reaction force estimation unit 65, similarly to the description of the floor reaction force estimation unit 58, it is assumed that the vector quantities such as the floor reaction force, the angular momentum, and the position vector are represented by the body coordinate system BC, unless otherwise specified, and the name of the coordinate system is often omitted when a vector quantity is denoted.

As shown in FIG. 20, the floor reaction force estimation unit 65 includes a total rate of change of angular momentum calculation unit 65a, a total floor reaction force calculation unit 65b, a moment arm length calculation unit 65c, a floor reaction force direction determination unit 65d, and a floor reaction force component calculation unit 65e, similarly to the floor reaction force estimation unit 58 of the human-side joint moment estimation unit 41.

The total rate of change of angular momentum calculation unit 65a receives inputs of the angular velocity ω(BCO/BC) of the origin BCO of the body coordinate system BC calculated by the body coordinate system acceleration and angular velocity calculation unit 54, the position vectors of the joint elements and the position vectors of the centers of gravity of the rigid elements of the orthosis rigid link model S1' calculated by the three-dimensional joint and element center-of-gravity location calculation unit 62, and the position vector of G_entire orthosis calculated by the entire center-of-gravity location calculation unit 63.

Then, using these input values, the total rate of change of angular momentum calculation unit 65a calculates the component Ls'y (See FIG. 21 and FIG. 22) around the Y axis of the total rate of change of angular momentum Ls', which is the time rate of change (first derivative) of the total angular momentum of the support orthosis 1, by calculating the following formula (108a), which is similar to the aforementioned formula (8a):

$$Ls'y = \Sigma(\text{I\_orthosis } n \times \theta'' \text{ (orthosis } n)y) + \quad (108a)$$
$$\Sigma(\text{m\_orthosis } n \times \Delta U(\text{G\_orthosis } n) \times \Delta ACC(\text{G\_orthosis } n))y$$

Subject to:

$$\Delta U(\text{G\_orthosis } n) \equiv U(\text{G\_orthosis } n) - U(\text{G\_entire orthosis})$$
$$\Delta ACC(\text{G\_orthosis } n) \equiv ACC(\text{G\_orthosis } n) - ACC(\text{G\_entire orthosis})$$
$$= U(\text{G\_orthosis } n)'' - U(\text{G\_entire orthosis})''$$

In this formula (108a), "n" indicates a number assigned arbitrarily to each rigid element of the orthosis rigid link model S1': I_n is a moment of inertia of a rigid element having the number n and θ"(orthosis n) is an angular acceleration around the center of gravity of the rigid element having the number n. Then, the first term Σ calculation in the formula (108a) is to add up the values of (I_orthosis n×θ"(orthosis n)y) of all the rigid elements of the orthosis rigid link model S1'. In addition, m_orthosis n is a weight of the rigid element having the number n, U(G_orthosis n) is a position vector on the body coordinate system BC of the center of gravity of the rigid element having the number n, ACC(G_orthosis n) is an acceleration of the center of gravity of the rigid element having the number n, ΔU(G_orthosis n) is a position vector relative to G_entire orthosis of the center of gravity of the rigid element having the number n, and ΔACC(G_n) is a relative acceleration to G_entire orthosis of the center of gravity of the rigid element having the number n. Furthermore, the second term Σ calculation in the formula (108a) is to add up the values of (m_orthosis n×ΔU(G_orthosis n)×ΔACC(G_orthosis n))y of all the rigid elements of the orthosis rigid link model S1'.

In this instance, I_orthosis n necessary for the first term Σ calculation in the formula (108a) is previously stored in the memory (not shown) of the arithmetic processing unit 25. In addition, θ"(orthosis n)y can be found as described below. Specifically, the angles of inclination of the rigid elements on the XZ plane (the sagittal plane on the body coordinate system BC) are sequentially calculated from the position vectors (U(J_left hip orthosis/BC) or the like) of the joint elements of the leg S2 calculated by the three-dimensional joint and element center-of-gravity location calculation unit 62. In this regard, the angles of inclination of the foot element S9, the abdomen element S5, and the chest element S6 of the orthosis rigid link model S1' are the same as those of the human rigid link model S1. Furthermore, the Y-axis component θ"(orthosis n)y of the angular acceleration of the each rigid element is found by adding the first derivative of the Y-axis component of the angular velocity ω(BCO/BC) of the origin BCO of the body coordinate system BC calculated by the body coordinate system acceleration and angular velocity calculation unit 54 of the human-side joint moment estimation unit 41 to the second derivative of the calculated angle of inclination.

Moreover, ΔU(G_orthosis n) necessary for the second term Σ calculation in the formula (108a) is determined according to the definition of the provision for the formula (108a) from the position vector (U(G_thigh orthosis/BC) or the like) of the center of gravity of the each rigid element calculated by the three-dimensional joint and element center-of-gravity location calculation unit 62 and the position vector U(G_entire orthosis/BC) of G_entire orthosis calculated by the entire center-of-gravity location calculation unit 63. Furthermore, ΔACC(G_orthosis n) is determined according to the definition of the provision for the formula (108a) from the second derivative U(G_orthosis n)" of the position vector of the center of gravity of the each rigid element calculated by the three-dimensional joint and element center-of-gravity location calculation unit 62 and the second derivative U(G_entire orthosis)" of the position vector of G_entire orthosis calculated by the entire center-of-gravity location calculation unit 63.

Incidentally, when finding the component Ls'y around the Y axis of the total rate of change of angular momentum by the formula (108a), it is possible to ignore the rigid elements of the upper body S3 of the orthosis rigid link model S1' (the abdomen element S5 and the chest element S6). This is because the motion of the rigid element of the upper body S3 of the orthosis rigid link model S1' hardly affects the total rate of change of angular momentum Ls' of the orthosis rigid link model S1' (support orthosis 1).

The total floor reaction force calculation unit 65b receives inputs of the acceleration ACC(BCO/BC) of the origin BCO of the body coordinate system BC calculated by the body coordinate system acceleration and angular velocity calculation unit 54 of the human-side joint moment estimation unit 41 and the position vector U(G_entire orthosis/BC) of G_entire orthosis calculated by the entire center-of-gravity location calculation unit 63.

Then, the total floor reaction force calculation unit 65b calculates component vector Frf(entire orthosis)x,z on the XZ plane of the total floor reaction force Frf(entire orthosis), which is the total sum of all the floor reaction forces acting on the support orthosis 1 (orthosis rigid link model S1'), by calculating the following formula (108b) similar to the aforementioned formula (8b):

$$Frf(\text{entire orthosis})x,z = \text{entire weight of orthosis} \times (ACC(BCO/BC) + U(\text{G\_entire orthosis}/BC)'')x,z \quad (108b)$$

Subsequently, the component Ls'y around the Y axis of the total rate of change of angular momentum Ls' calculated as described above and the component vector Frf(entire orthosis)x,z on the XZ plane (sagittal plane) of the total floor reaction force are input to the moment arm length calculation unit 65c. The moment arm length calculation unit 65c calculates the moment arm length (the length for transforming the translational force to the moment) from the input values, similarly to the moment arm length calculation unit 58c of the human-side joint moment estimation unit 41. In this instance, the moment arm length calculation unit 65c calculates the moment arm length rs by the following formula (108c), which is similar to the aforementioned formula (8c):

$$rs = Ls'y/|Frf(\text{entire orthosis})x,z| \quad (108c)$$

The moment arm length rs calculated by the above formula (108c) takes a positive or negative value according to the direction (sign) of the component Ls'y around the Y axis of the total rate of change of angular momentum, similarly to the moment arm length r calculated by the aforementioned formula (8c). In this instance, if Ls'y has the direction indicated by the arrow shown in FIG. 21 and FIG. 22, the Ls'y value is determined to be positive.

The moment arm length rs obtained in this manner is then input to the floor reaction force direction determination unit 65d. The floor reaction force direction determination unit 65d further accepts outputs of the landing sensors 34 and 35, the position vector U(orthosis COP/BC) of the floor reaction force application point COP estimated by the floor reaction force application point estimation unit 64, and the position vector U(G_entire orthosis/BC) of G_entire orthosis calculated by the entire center-of-gravity location calculation unit 63. Thereafter, the floor reaction force direction determination unit 65d determines the direction of the floor reaction force acting on the each leg link portion 4 of the support orthosis 1, similarly to the floor reaction force direction determination unit 58d of the human-side joint moment estimation unit 41, by using these input values.

Specifically, if the person A is determined to be in the double support state based on the detected outputs of the landing sensors 34 and 34, regarding the direction (the direction on the XZ plane) of the floor reaction force Frf(right leg orthosis) of the right leg link portion 4 (right leg S2), the gradient α(right leg orthosis) on the body coordinate system BC of the straight line K(right orthosis), which passes through the floor reaction force application point COP(right orthosis) of the right leg link portion 4 and is tangent to the circle having the radius rs (more accurately, |rs|) whose center is G_entire orthosis, is determined to indicate the direction (the direction on the XZ plane) of the floor reaction force Frf(right leg orthosis) of the right leg link portion 4, as shown in FIG. 22. In this instance, if the moment arm length rs is positive, the straight line K(right orthosis) is assumed to be tangent to the backward portion of the circle Cis having the radius rs. In other words, when the component vector Frf(right leg orthosis)x,z on the XZ plane of the floor reaction force Frf(right leg orthosis) acts on the floor reaction force application point COP(right orthosis) with the straight line K(right orthosis) as a line of action, the gradient α(right leg orthosis) of the straight line K(right orthosis) tangent to the circle Cis is determined in such a way that the direction of the component around the Y axis of the moment generated around G_entire orthosis by the force application is the same as the direction of the component Ls'y around the Y axis of the total rate of change of angular momentum. Regarding the left leg link portion 4 (left leg S2), the gradient α(left leg orthosis) on the body coordinate system BC of the straight line K(left), which indicates the direction (the direction on the sagittal plane) of the floor reaction force Frf(left leg orthosis) of the left leg link portion 4, is determined in the same manner as for the right leg link portion 4.

If the person A in the single support state, as shown in FIG. 21, CGs is defined as the component vector on the XZ plane of the vector from the floor reaction force application point COP of the landing leg link portion 4 (the right leg link portion in the shown example) to G_entire orthosis (the position vector of G_entire orthosis to COP). Then, the angle θas formed by the vector CGs and the straight line K(right orthosis), which passes through the floor reaction force application point COP of the right leg link portion 4 and is tangent to the circle having the radius rs (more accurately, |rs|) whose center is G_entire orthosis, is determined to represent the direction (the direction on the sagittal plane) of the floor reaction force Frf(right leg orthosis). In this instance, if the moment arm length rs is positive, the straight line K(right orthosis) is assumed to be tangent to the backward portion of the circle Cis having the radius rs. In other words, when the component vector Frf(right leg orthosis)x,z on the XZ plane of the floor reaction force Frf(right leg orthosis) acts on the floor reaction force application point COP with the straight line K(right orthosis) as a line of action, the angle θas on the XZ plane of the straight line K(right orthosis) to the vector CGs in such a way that the direction of the component around the Y axis of the moment generated around G_entire orthosis by the force application is the same as the direction of the component around the Y axis of the total rate of change of angular momentum.

The angle θas is calculated by the following formula (108d), which is similar to the aforementioned formula (8d):

$$\theta as = -\sin^{-1}(rs/|CGs|) \quad (108d)$$

In this instance, the absolute value of the vector CGs is calculated from the position vector U(right orthosis COP/BC) of the floor reaction force application point COP found by the floor reaction force application point estimation unit 64 and the position vector U(G_entire orthosis/BC) of G_entire orthosis found by the entire center-of-gravity location calculation unit 63.

Also in the single support state in which only the left leg link portion 4 is landing, similarly to the above, the angle θas formed by the component vector CGs on the XZ plane of the position vector of G_entire orthosis to the floor reaction force application point COP of the left leg link portion 4 and the straight line K(left orthosis), which passes through the floor reaction force application point COP of the left leg link portion 4 and is tangent to the circle having the radius rs (more accurately, |rs|) whose center is G_entire orthosis, is determined to represent the direction of the component vector Frf(left leg orthosis)x,z on the XZ plane of the floor reaction force Frf(left leg orthosis).

By the processing of the floor reaction force direction determination unit 65d described hereinabove, the direction (the direction on the sagittal plane of the body coordinate system BC) of the floor reaction force Frf acting on the landing leg link portion 4 is determined in such a way that the line of action of the component vector Frf(leg orthosis)x,z on the XZ plane (the sagittal plane of the body coordinate system BC) of the floor reaction force Frf acting on the landing leg link portion 4 is tangent to the circle Cis whose radius is the moment arm length rs determined by the formula (108c) and whose center is G_entire orthosis and that the moment generated around G_entire orthosis by Frf(leg orthosis)x,z having the direction of the line of action is coincident with the component Ls'y around the Y axis of the total rate of change of angular momentum.

Subsequently, the direction (the gradient α(leg orthosis) in the double support state or the angle θas in the single support state) of the floor reaction force determined by the floor reaction force direction determination unit 65d is input to the floor reaction force component calculation unit 65e. The floor reaction force component calculation unit 65e also accepts the component Frf(entire orthosis)x,z on the XZ plane of the total floor reaction force found by the total floor reaction force calculation unit 65b. In the single support state, the floor reaction force direction determination unit 65d inputs the vector CGs found by its processing into the floor reaction force component calculation unit 65e. Moreover, the position vector U(COP/BC) of the floor reaction force application point COP of the each leg link portion 4 and the position vector U(G_entire orthosis/BC) of G_entire orthosis are also input to the floor reaction force component calculation unit 65e.

Then, the floor reaction force component calculation unit 65e finds the coordinate component values on the body coordinate system BC of the floor reaction force Frf acting on the landing leg link portion 4 from these input values in the same manner as for the floor reaction force component calculation unit 58e of the human-side joint moment estimation unit 41.

More specifically, if the anteroposterior distance between feet in the double support state (See FIG. 13) is greater than the second threshold value, the components Frf(right leg orthosis)x, Frf(right leg orthosis)z, Frf(left leg orthosis)x, and Frf(left leg orthosis)z on the XZ plane of the corresponding floor reaction force are calculated by the following formulas (109e) to (109h), which are similar to the aforementioned formulas (9e) to (9h), respectively:

$$Frf(\text{right leg orthosis})x = (Frf(\text{entire orthosis})z - \alpha(\text{left leg orthosis}) \times Frf(\text{entire orthosis})x)/\Delta\alpha s \quad (109e)$$

$$Frf(\text{right leg orthosis})z = \quad (109f)$$
$$(\alpha(\text{right leg orthosis}) \times Frf(\text{entire orthosis})z - \alpha(\text{right leg orthosis}) \times \alpha(\text{left leg orthosis}) \times Frf(\text{entire orthosis})x)/\Delta\alpha s$$

$$Frf(\text{left leg orthosis})x = (-Frf(\text{entire orthosis})z + \alpha(\text{right leg orthosis}) \times Frf(\text{entire orthosis})x)/\Delta\alpha s \quad (109g)$$

$$Frf(\text{left leg orthosis})z = \quad (109h)$$
$$(-\alpha(\text{left leg orthosis}) \times Frf(\text{entire orthosis})z + \alpha(\text{right leg orthosis}) \times \alpha(\text{left leg orthosis}) \times Frf(\text{entire orthosis})x)/\Delta\alpha s$$

Subject to:

$$\Delta\alpha s = \alpha(\text{right leg orthosis}) - \alpha(\text{left leg orthosis})$$

The formulas (109e) to (109h) are obtained based on the relational expressions similar to the aforementioned formulas (9a) to (9d). Hereinafter, a reference symbol Frfs1$x,z$ is appended to a vector made of a pair of the X-axis component and the Z-axis component of the floor reaction force found by these formulas (109e) to (109h).

If the anteroposterior distance between feet in the double support state (See FIG. 13) is smaller than the first threshold value, the component vectors Frf(right leg orthosis)x,z and Frf(left leg orthosis)x,z on the XZ plane of the corresponding floor reaction force are calculated by the following formulas (110), which is similar to the aforementioned formulas (10):

$$Frf(\text{right leg orthosis})x, z = Frf(\text{left leg orthosis})x, z \quad (110)$$
$$= Frf\_s(\text{entire orthosis})x, z/2$$

Subject to:

$$Frf\_s(\text{entire orthosis})x, z = \begin{bmatrix} \cos\theta bs & \sin\theta bs \\ -\sin\theta bs & \cos\theta bs \end{bmatrix} \times CavsGs \times \frac{|Frf(\text{entire orthosis})x, z|}{|CavsGs|}$$

CavsGs in the provision for the formula (110) is a component vector on the XZ plane of the vector from the midpoint Cavs of the line segment between the respective floor reaction force application points COPs of the right and left leg link portions 4 to G_entire orthosis (the position vector of G_entire orthosis relative to the midpoint Cavs). The position vector on the body coordinate system BC of Cavs is calculated as an average value of the position vectors of the floor reaction force application points COPs of the right and left leg link portions 4 (=(U(right orthosis COP)+U(left orthosis COP))/2). Moreover, θbs is an angle formed by the vector CavsGs and a straight line passing through the midpoint Cavs on the XZ plane and having a radius rs (more accurately, |rs|) whose center is G_entire orthosis and is calculated by the formula in which "CGs" in the right-hand side of the formula (108d) is replaced with "CavsGs." Therefore, Frf_s(entire orthosis)x,z in the formula (110) is a vector (two-dimensional vector) that has the same direction as the component vector on the XZ plane of the vector from the midpoint of the line segment between the floor reaction force application points COPs of the both leg link portions 4 to G_entire orthosis and is generated by rotating a vector having the magnitude of Frf(entire orthosis)x,z by the angle θbs around the midpoint Cavs on the XZ plane (the sagittal plane). Therefore, on the XZ plane, the line of action of Frf_s(entire orthosis)x,z (the straight line passing through the midpoint Cavs on the XZ plane and having the same direction as the vector Frf_s(entire orthosis)x,z) is tangent to the circle Cis having the radius rs whose center is G_entire orthosis.

Therefore, if the anteroposterior distance between feet is equal to or smaller than the first threshold value in the double support state, Frf(right leg orthosis)x,z and Frf(left leg orthosis)x,z obtained by the formula (110) have the same magnitude and the direction and the magnitude of the total sum is the same as the magnitude of the total floor reaction force Frf(entire orthosis). Moreover, each of the lines of action of Frf(right leg orthosis)x,z and Frf(left leg orthosis)x,z (the lines of action on the XZ plane each passing through the floor reaction force application point COP) is substantially tangent to the circle Cis having the radius rs whose center is G_entire orthosis.

Hereinafter, reference symbol Frfs2$x,z$ is appended to the vector made of a pair of the X-axis component and the Z-axis component of the floor reaction force found by the formula (110).

Then, in the double support state, the floor reaction force component calculation unit 65e finally finds the component vectors Frf(leg orthosis)x,z and (true value of the estimated value of Frf(leg orthosis)x,z) on the XZ plane of the floor reaction force of the each leg link portion 4 by the following formula (111a), which is similar to the aforementioned formula (11a):

$$Frf(\text{leg orthosis})x,z = W \times Frfs1x,z + (1-W) \times Frfs2x,z \quad (111a)$$

In the above, W is a weighting factor, which is set according to the anteroposterior distance between feet using the data table defined as shown in FIG. 15.

The above arithmetic processing enables the calculation of the component vector Frf(leg orthosis)x,z on the XZ plane of the floor reaction force acting on the each leg link portion 4 in the double support state. When Frfs1$x,z$ is calculated and if the absolute value of the gradient α(leg orthosis) exceeds a predetermined value, the value of α(leg orthosis) is forcibly limited to the predetermined value, similarly to the processing of the floor reaction force component calculation unit 58e of the human-side joint moment estimation unit 41.

On the other hand, the floor reaction force (more specifically, its X-axis component and Z-axis component) acting on the leg link portion 4 landing in the single support state is calculated by the following formula (111b), which is similar to the aforementioned formula (11b):

$$Frf(\text{leg orthosis})x, \quad (111b)$$
$$z = \begin{bmatrix} \cos\theta \text{ as} & \sin\theta \text{ as} \\ -\sin\theta \text{ as} & \cos\theta \text{ as} \end{bmatrix} \times CGs \times \frac{|Frf(\text{entire orthosis})x, z|}{|CGs|}$$

In other words, the component vector Frf(leg orthosis)x,z on the XZ plane of the floor reaction force acting on the landing leg link portion 4 is found as a vector generated by rotating a vector, starting from the floor reaction force application point COP of the leg link portion 4 to G_entire orthosis and having the magnitude of Frf(entire orthosis)x,z, by the angle θas around the floor reaction force application point COP on the XZ plane (the sagittal plane). The line of action of Frf(leg orthosis)x,z found in this manner is tangent to the circle Cis having the radius r whose center is G_entire orthosis.

In this embodiment, in either case of the double support state or the single support state, it is assumed that the Y-axis component of the floor reaction force is zero in the each leg link portion 4 of the support orthosis 1. In the single support state, the floor reaction force acting on the foot attachment portion 3 not landing is assumed to be zero.

With the above processing of the floor reaction force component calculation unit 65e, in the double support state, the lines of action (the lines of action each passing through the floor reaction force application point COP of the each leg link portion 4 on the XZ plane) of the component vectors Frf(right leg orthosis)x,z and Frf(left leg orthosis)x,z of the floor reaction force are tangent to the circle Cis having the radius rs (moment arm length) whose center is G_entire orthosis, and the direction of each of Frf(right leg orthosis)x,z and Frf(left leg orthosis)x,z is determined in such a way that the direction of the moment (moment around the Y axis) generated around G_entire orthosis by each of Frf(right leg orthosis)x,z and Frf(left leg orthosis)x,z (or the total sum of them) is coincident with the direction of the component Ls'y around the Y axis of the total rate of change of angular momentum. Then, on that basis, the estimated values (each of which is a pair of the X-axis component value and the Z-axis component value) of Frf(right leg orthosis)x,z and Frf(left leg orthosis)x,z are calculated in such a way that the total sum of Frf(right leg orthosis)x,z and Frf(left leg orthosis)x,z (=Frf(right leg orthosis)x,z+Frf(left leg orthosis)x,z) is coincident with Frf(entire orthosis)x,z.

In the single support state, the line of action (the line of action passing through the floor reaction force application point COP of the leg link portion 4) of the component vector Frf(leg orthosis)x,z of the floor reaction force of the landing leg link portion 4 is tangent to the circle Cis having the radius rs (moment arm length) whose center is G_entire orthosis on the XZ plane, and the direction of Frf(leg orthosis)x,z is determined in such a way that the direction of the moment (moment around the Y axis) generated around G_entire orthosis by Frf(leg orthosis)x,z is coincident with the direction of the component Ls'y around the Y axis of the total rate of change of angular momentum. Then, on that basis, Frf(leg orthosis)x,z of the landing leg link portion 4 is calculated in such a way that the magnitude (absolute value) of Frf(leg orthosis)x,z is coincident with the magnitude (absolute value) of Frf(entire orthosis)x,z.

Frf(leg orthosis)x,z calculated in this manner is an estimated value of the component vector on the XZ plane of the floor reaction force acting on the each leg link portion 4 of the support orthosis 1, supposing that the motion of the support orthosis 1 put on the person A has been made by the support orthosis 1 independently (by itself). In other words, the floor reaction force Frf(leg orthosis)x,z is an estimated value of the component vector on the XZ plane of the floor reaction force kinetically required when the support orthosis 1 makes the same motion as that of the support orthosis 1 that follows the motion of the person A wearing the support orthosis 1 independently (by itself).

While the Y-axis component of the floor reaction force Frf(leg orthosis) has been set to 0 in this embodiment, it is also possible to determine the direction of the component vector Frf(leg orthosis)y,z of the floor reaction force on the YZ plane in such a way that the direction of the component around the X axis of the total rate of change of angular momentum is coincident with the direction of the moment generated around G_entire orthosis (the moment around the X axis) by the total sum of the component vector Frf(leg orthosis)y,z on the YZ plane of the floor reaction forces of the landing each leg link portion 4, further taking into consideration the component around the X axis of the total rate of change of angular momentum. The direction may be determined by using the moment arm length on the YZ plane and the circle having the radius of the moment arm length, similarly to the above. The direction of Frf(leg orthosis)y,z is then determined. Thereafter, in the doubles support state, each coordinate component value of each Frf(leg orthosis)y,z may be determined in such a way that the total sum of the component vectors Frf(leg orthosis)y,z on the YZ plane of the floor reaction forces acting on the respective leg link portions 4 is coincident with the component vector Frf(entire orthosis)y,z on the YZ plane of the total floor reaction force. Moreover, in the single support state, each coordinate component value of Frf(leg orthosis)y,z may be determined in such a way that the magnitude of the component vector Frf(leg orthosis)y,z on the YZ plane of the floor reaction force acting on the landing leg link portion 4 is coincident with the magnitude of the component vector Frf(entire orthosis)y,z on the YZ plane of the total floor reaction force.

The above is the arithmetic processing of the floor reaction force estimation unit 65 of the orthosis-side joint moment estimation unit 42. Incidentally, to remove noise components from the estimated value of the floor reaction force obtained as stated above, the estimated value filtered with a second Butterworth filter (low pass filter) or the like may be obtained as an estimated value of the floor reaction force finally.

Subsequently, the orthosis-side joint moment estimation unit 42 performs the arithmetic processing of the leg plane projection unit 66. In this processing, floor reaction forces Frf(right leg orthosis/BC) and Frf(left leg orthosis/BC) calculated by the floor reaction force estimation unit 65 and the position vector U(orthosis COP/BC) of the floor reaction force application point COP calculated by the floor reaction force application point estimation unit 64 are projected to the leg plane PL corresponding to each of the legs S2 for each thereof by using the transformation tensor R(BC→LC) (=R (LC→BC)$^T$), which is a transposition of the transformation tensor R(LC→BC) generated by the transformation tensor generation unit 51 of the human-side joint moment estimation unit 41.

More specifically, the floor reaction force Frf(right leg orthosis/right LC) and Frf(left leg orthosis/left LC) viewed from the each leg coordinate system LC are obtained by multiplying the floor reaction forces Frf(right leg orthosis/BC) and Frf(left leg orthosis/BC) each by the transformation tensor R(BC→right LC) and R(BC→left LC) as shown by the following formulas (112c) and (112d):

$$Frf(\text{right leg orthosis/right } LC)=R(BC\rightarrow\text{right } LC)\times Frf(\text{right leg orthosis}/BC) \qquad (112c)$$

$$Frf(\text{left leg orthosis/left } LC)=R(BC\rightarrow\text{left } LC)\times Frf(\text{left leg orthosis}/BC) \qquad (112d)$$

Moreover, the position vector U(orthosis COP/LC) of the floor reaction force application point COP viewed from the leg coordinate system LC corresponding to the landing leg S2 is obtained by multiplying the position vector U(orthosis COP/BC) of the floor reaction force application point COP of the landing leg S2 (the leg link portion 4) by the transformation tensor R(BC→LC) corresponding to the landing leg S2 as shown by the following formula (112e):

$$U(\text{orthosis } COP/LC)=R(BC\rightarrow LC)\times U(\text{orthosis } COP/BC) \qquad (112e)$$

In the above, the position vector U(orthosis COP/LC) is calculated only for the landing leg S2 in the single support state of the person A, while it is calculated for each of the right and left legs S2 in the double support state. The formulas (112c to 112e) correspond to the aforementioned formulas (12c) to (12e).

As additional information, the acceleration vector ACC (BCO/LC) and the angular velocity vector ω(BCO/LC) viewed on each of the right and left leg coordinate systems LC is the same as those calculated as stated above by the leg plane projection unit 59 of the human-side joint moment estimation unit 41 (See the aforementioned formulas (12a) and (12b)), and therefore there is no need to calculate them in the leg plane projection unit 66 of the orthosis-side joint moment estimation unit 42.

In the following description of the joint moment calculation unit 67, it is assumed that the acceleration vector ACC (BCO/LC), the floor reaction forces Frf(right leg orthosis/ right LC) and Frf(left leg orthosis/left LC), and the position vector U(orthosis COP/LC) of the floor reaction force application point mean two-dimensional vectors made of a pair of the X coordinate component and the Z coordinate component. Regarding the angular velocity ω, a value on the leg plane PL is represented by ω(BCO/LC)y.

Subsequently, the orthosis-side joint moment estimation unit 42 performs arithmetic processing of the joint moment calculation unit 67. In the arithmetic processing of the joint moment calculation unit 67, the joint moments of the joint elements J_ankle, J_knee, and J_hip are calculated in order by calculating the inverse dynamics model (a two-dimensional calculation on the each leg plane PL) based on the equations of motion related to the translational motion and the rotary motion of the foot element S9, the crus element S8, and the thigh element S7 of the each leg S2 shown below, similarly to the arithmetic processing of the joint moment calculation unit 67 of the human-side joint moment estimation unit 41.

In this instance, the equations of motion related to the translational motion are given by the formulas (115a) to (115c) below, and the equations of motion related to the rotary motion are given by the formulas (115d) to (115f) below. In the equations of motion shown below, one end closer to the waist element S4 is denoted by "P_□□ orthosis" and the other end farther from the waist element S4 is denoted by "D_□□ orthosis" (□□ is a name of the rigid element) for both ends the rigid elements of the foot element S9, the crus element S8, and the thigh element S7 of the orthosis rigid link model S1', similarly to the aforementioned arithmetic processing of the joint moment calculation unit 60. For example, the end of the crus element S8 on the knee joint J_knee (J2) side is denoted by "P_crus orthosis" and the other end on the ankle joint J_ankle (J3) side is denoted by "D_crus orthosis." In addition, F(P_□□ orthosis/BC) and F(D_□□ orthosis/ BC) each mean the reaction force (the two-dimensional translational vector on the leg plane PL) applied to the end of the rigid element (the rigid element of the orthosis rigid link model S1') having the name indicated by □□ from the object put in contact with the end. Similarly, M(P_□□ orthosis) and M(D_□□ orthosis) each mean the reaction force moment (the moment around the axis perpendicular to the leg plane PL (around the axis parallel to the Y axis of the leg coordinate system LC)) applied to the end of the rigid element (the rigid element of the orthosis rigid link model S1') having the name indicated by □□ from the object put in contact with the end.

$$F(\text{P\_foot orthosis}/LC) = \\ \text{m\_foot orthosis} \times (ACC(BCO/LC) + U(\text{G\_foot orthosis}/LC)'') - \\ Frf(\text{leg orthosis}/LC) \quad (115a)$$

$$F(\text{P\_crus orthosis}/LC) = \text{m\_crus orthosis} \times \\ (ACC(BCO/LC) + U(\text{G\_crus orthosis}/LC)'') - \\ F(\text{D\_crus orthosis}/LC) \quad (115b)$$

$$F(\text{P\_thigh orthosis}/LC) = \text{m\_thigh orthosis} \times \\ (ACC(BCO/LC) + U(\text{G\_thigh orthosis}/LC)'') - \\ F(\text{D\_thigh orthosis}/LC) \quad (115c)$$

$$M(\text{P\_foot orthosis}) = 0 \quad (115d)$$

$$M(\text{P\_crus orthosis}) = \\ \text{I\_crus orthosis} \times (\omega(\text{crus orthosis})' + \omega(BCO/LC)y') - \\ \{(U(\text{D\_crus orthosis}/LC) - U(\text{G\_crus orthosis}/LC)) \times \\ F(\text{D\_crus orthosis}/LC)\}y - \\ \{(U(\text{P\_crus orthosis}/LC) - U(\text{G\_crus orthosis}/LC)) \times \\ F(\text{P\_crus orthosis}/LC)\}y - M(\text{D\_crus orthosis}) \quad (115e)$$

$$M(\text{P\_thigh orthosis}) = \\ \text{I\_thigh orthosis} \times (\omega(\text{thigh orthosis})' + \omega(BCO/LC)y') - \\ \{(U(\text{D\_thigh orthosis}/LC) - U(\text{G\_thigh orthosis}/LC)) \times \\ F(\text{D\_thigh orthosis}/LC)\}y - \\ \{(U(\text{P\_thigh orthosis}/LC) - U(\text{G\_thigh orthosis}/LC)) \times \\ F(\text{P\_thigh orthosis}/LC)\}y - M(\text{D\_thigh orthosis}) \quad (115f)$$

In this regard, F(D_crus orthosis/BC)=−F(P_foot orthosis/ BC), F(D_thigh orthosis/BC)=−F(P_crus orthosis/BC), M(D_crus orthosis)=−M(P_foot orthosis), and M(D_thigh orthosis)=−M(P_crus orthosis) Moreover, I_crus orthosis and I_thigh orthosis each are a moment of inertia (moment of inertia of a single unit of the support orthosis 1) around the center of gravity of each of the crus element S8 and the thigh element S7 of the orthosis rigid link model S1'. They are previously determined based on measurement data or the like and then stored in the memory of the arithmetic processing unit 25.

These formulas (115a) to (115f) correspond to the aforementioned formulas (15a) to (15f). In this embodiment, however, the ankle joint region 11 (J_ankle) of the each leg link portion 4 is not provided with the electric motor and thus the ankle joint region 11 is free to rotate. Therefore, M(P_ankle orthosis)=0 in the formula (15d). In the joint moment calculation unit 67, the joint moments M(P_foot orthosis), M(P_crus orthosis), and M(P_thigh orthosis) are sequentially calculated finally for each of the legs S2 by using the formulas (115a) to (115f), similarly to the human-side joint moment estimation unit 41.

In this instance, ACC(BCO/LC) and ω(BCO/LC)y' necessary for the calculation are the same as those for use in the aforementioned formulas (15a) to (15f). In addition, ω(crus orthosis)' and ω(thigh orthosis)' are determined from the time series data of the tilt angles as second derivatives of the tilt angles θ_crus orthosis and θ_thigh orthosis found by the two-dimensional leg posture and element center-of-gravity location calculation unit 61, respectively. Moreover, U(P_crus/LC) (=U(D_thigh/LC) and U(P_thigh/LC) are U(J_knee orthosis/LC) and U(J_hip orthosis/LC) found by the two-dimensional leg posture and element center-of-gravity location calculation unit 61, respectively. Furthermore, U(G_foot orthosis/LC)'', U(G_crus orthosis/LC)'', and U(G_thigh orthosis/LC)'' are determined from the time series data of the position vectors as second derivatives of the position vectors (more accurately, pairs of the X coordinate component and the Z coordinate component of the position vectors) G_foot orthosis, G_crus orthosis, and G_thigh orthosis on the leg coordinate system LC previously calculated by the two-dimensional leg posture and element center-of-gravity location calculation unit 61, respectively, similarly to the aforementioned formulas (15g) to (15i). Still further, Frf(leg orthosis/LC) is a two-dimensional vector achieved by projecting the floor reaction force vector previously obtained by the floor reaction force estimation unit 65 onto the leg plane by using the leg plane projection unit 66, and U(orthosis COP/LC) is a two-dimensional vector achieved by projecting the floor reaction force application point previously obtained by the floor reaction force application point estimation unit 64 onto the leg plane PL by using the leg plane projection unit 66.

While the moments of inertia I_crus orthosis and I_thigh orthosis have been considered in this embodiment, they are sufficiently close to zero in general. Thus, in the calculations of the formulas (115d) to (115f), it is possible to omit the terms including the moments of inertia I_crus orthosis and I_thigh orthosis.

In the arithmetic processing of the joint moment calculation unit 67, the joint moments M(P_foot orthosis), M(P_crus orthosis), and M(P_thigh orthosis) around the axis perpendicular to the leg plane PL of the joint regions 7, 9, and 11 of the support orthosis 1 are calculated in order from the ankle joint region 11 (J3) side as described above. These joint moments M(P_foot orthosis), M(P_crus orthosis), and M(P_thigh orthosis) are to be generated in the ankle joint region 11, the knee joint region 9, and the hip joint region 7 of the each leg link portion 4 of the support orthosis 1, supposing that the support orthosis 1 is making the motion of the support orthosis 1 that follows the motion of the person A wearing the support orthosis 1 independently (by itself). In other words, the joint moments can satisfy the required kinetic relation (physical law) between the motion of the support orthosis 1 and the external force (floor reaction force) and the gravity force acting on the support orthosis 1 when it is considered that the support orthosis 1 is independently making the motion with being removed from the person A.

Therefore, if torques equal to M(P_crus orthosis) and M(P_thigh orthosis) are generated in the electric motors 15 and 16, the person A feels as if he is making the motion by himself without wearing the support orthosis 1 in theory.

The above is the details of the arithmetic processing of the human-side joint moment estimation unit 41 and the orthosis-side joint moment estimation unit 42 of the arithmetic processing unit 25.

Subsequently, the arithmetic processing unit 25 performs the arithmetic processing of the target joint support moment determination unit 43 and the actual joint support moment estimation unit 44.

In the arithmetic processing of the target joint support moment determination unit 43, target joint support moments, which should be generated at the knee joint and the hip joint of the each leg by torques of the electric motors 15 and 16 of the support orthosis 1 are determined according to the knee joint moment M(P_crus) and the hip joint moment M(P_thigh) of the each leg found by the human-side joint moment estimation unit 41. In this instance, for example, the product obtained by multiplying each of the knee joint moment M(P_crus) and the hip joint moment M(P_thigh), for example, by a predetermined ratio (10% or the like) is determined as a target joint support moment Mat(knee) or Mat (hip) to be generated. The above predetermined ratio may be different between the knee joint and the hip joint and may be variably set according to a motion condition of the person A or an environmental condition of a floor or the like.

Figure 23:
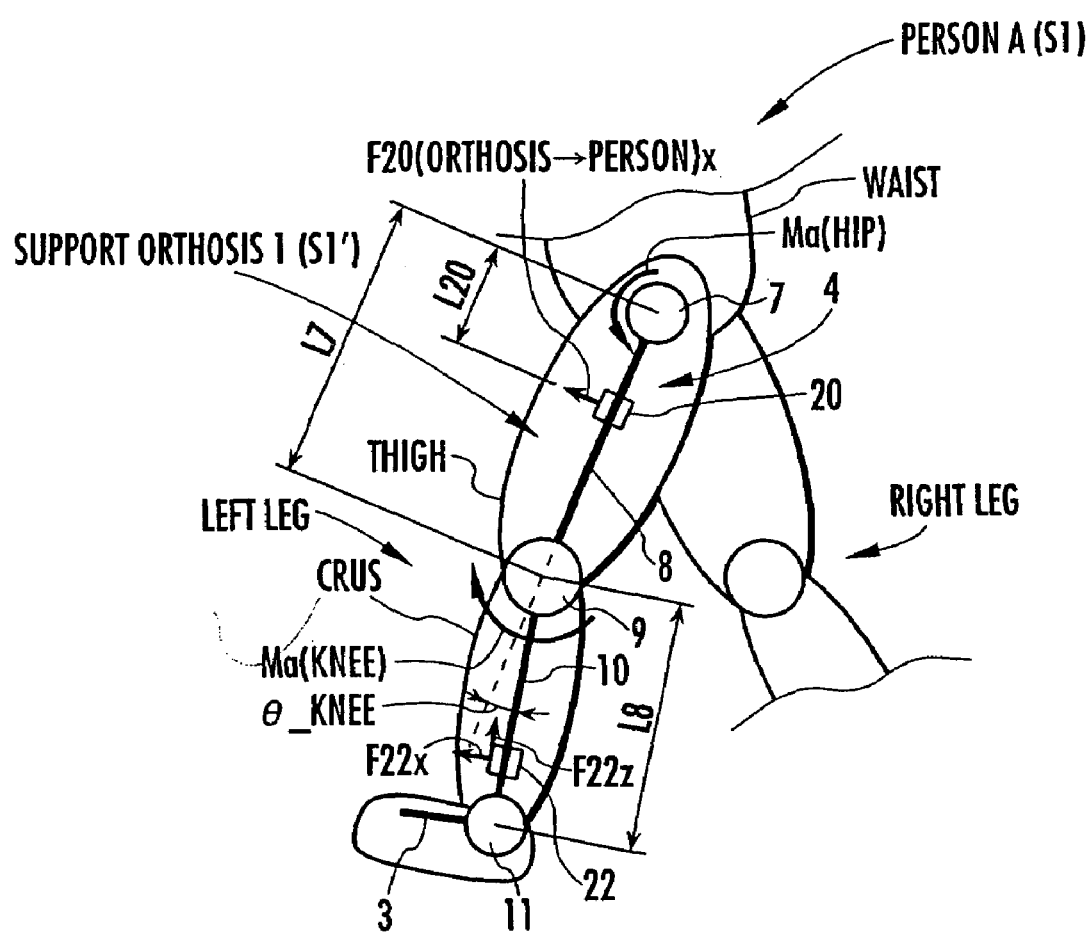
FIG. 23 is a diagram for explaining method of estimating an actual joint support moment.

In arithmetic processing of the actual joint support moment estimation unit 44, an estimated value of an actual joint support moment (a moment around the axis perpendicular to the leg plane PL of the each leg) actually generated at the knee joint and the hip joint of the each leg of the person A due to the torques of the electric motors 15 and 16 of the support orthosis 1, on the basis of detected outputs of the force sensors 20 and 22 and the displacement sensor 21. This arithmetic processing is performed for each of the legs. Hereinafter, the arithmetic processing of the actual joint support moment estimation unit 44 will be described with reference to FIG. 23. FIG. 23 shows the lower part of the body of the person A and the essential lower part of the body of the support orthosis 1 typically (in the form of a rigid link model). FIG. 23 mainly shows the left leg and the left leg link portion 4, assuming that the direction perpendicular to the surface of the page is coincident with the direction perpendicular to the XZ plane of the leg coordinate system LC (the direction perpendicular to the leg plane PL) of the left leg. Furthermore, in the illustration of FIG. 23, the central axis of the thigh and the central axis of the crus of the person A are coincident with the central axis of the high link member 8 and the central axis of the crus link member 10 of the support orthosis 1 on the XZ plane of the leg coordinate system LC, respectively, for convenience of diagrammatic representation, but they need not be coincident with each other.

The actual joint support moment estimation unit 44 first detects a force (translational force) applied from the support orthosis 1 to the each leg of the person A at the place of the force sensor 20 (the coupled place between the thigh link member 8 and the thigh of the person A) from the output of the force sensor 20 disposed on the thigh link member 8 of the each link member 4 of the support orthosis 1. In this instance, the force sensor 20 is free to move in the central axis direction (in the longer direction) in this embodiment. Therefore, a force (translational force) in the direction perpendicular to the central axis direction of the thigh link member 8 applies from the thigh of the person A to the force sensor 20 and then a reaction force opposite in sign (direction) to the applied force is detected from the output of the force sensor 20. Hereinafter, the detected force (vector) is referred to as an applied force F20(orthosis→person).

In this embodiment, the force detected from the output of the force sensor 20 is, more specifically, a component in the direction perpendicular to the central axis direction of the thigh of the person A on the XZ plane of the leg plane LC in the applied force F20(orthosis→person). Hereinafter, the applied force component is denoted by reference symbol F20(orthosis→person)x as shown in FIG. 23. In this instance, if the central axis direction of the thigh of the person A is coincident with the central axis direction of the thigh link member 8, a detected value of F20(orthosis→person)x can be directly obtained from the output of the force sensor 20. Unless the central axis direction of the thigh of the person A is coincident with the central axis direction of the thigh link member 8, a detected value of F20(orthosis→person)x can be calculated from the tilt angles $\theta$_thigh and $\theta$_thigh orthosis previously calculated by the two-dimensional leg posture and element center-of-gravity location calculation units 52 and 61, respectively.

Moreover, the actual joint support moment estimation unit 44 detects a force (translational force), which is applied from the each link portion 4 to the outside of the foot attachment portion 3 (the foot of the person A or a floor) via the foot attachment portion 3, from the output of the force sensor 22 disposed at the bottom end of the crus link member 10 of the each leg link portion 4 of the support orthosis 1. In this instance, as described above, the following resultant force is transmitted to the force sensor 22 via the foot link member 12 and the ankle joint region 11: the resultant force between the floor reaction force applied from the floor to the each leg link portion 4 via the foot attachment portion 3 (more specifically, the floor reaction force applied to the each leg link portion 4 of the support orthosis 1 supposing that the support orthosis 1 independently makes the motion of the support orthosis 1 following the motion of the legs of the person A) and the translational force applied from the foot of the person A to the leg link portion 4 via the foot attachment portion 3. Then, the actual joint support moment estimation unit 44 detects a reaction force opposite in sign (direction) to the resultant force transmitted to the force sensor 22 from the output of the force sensor 22. Hereinafter, the detected force (vector) is referred to as the applied force F22. In this embodiment, the force detected from the output of the force sensor 22 is, more specifically, made of the component in the central axis direction of the crus of the person A on the XZ plane of the leg plane LC and the component in the direction perpendicular to the central axis direction in the applied force F22. Hereinafter, these applied force components are denoted by reference symbols F22z and F22x, respectively, as shown in FIG. 22. In this instance, if the central axis direction of the crus of the person A is coincident with the central axis direction of the crus link member 10, detected values of F22x and F22z can be directly obtained from the outputs of the force sensor 22. Unless the central axis direction of the crus of the person A is coincident with the central axis direction of the crus link member 10, the detected values of F22x and F22z can be calculated from the outputs of the force sensor 22 and the tilt angles θ_crus and θ_crus orthosis previously calculated by the two-dimensional leg posture and element center-of-gravity location calculation units 52 and 61, respectively.

In this regard, the applied force F22 is, in other words, a resultant force between the force (translational force) applied from the leg link portion 4 to the foot of the person A via the foot attachment portion 3 and the force (translational force) applied from the foot attachment portion 3 to the floor supposing that the support orthosis 1 is independently making the motion of the support orthosis 1 following the motion of the person A. The latter force is opposite in sign (direction) to the floor reaction force Frf(leg orthosis) applied from the floor to the foot attachment portion 3 (=−Frf(leg orthosis)). Therefore, the force (translational force. Hereinafter, referred to as applied force F22(orhosis→person)) applied from the leg ling portion 4 to the foot of the person A via the foot attachment portion 3 is obtained by the following formula (151):

$$F22(\text{orthosis} \to \text{person}) = F22 - (-Frf(\text{leg orthosis})) \quad (151)$$
$$= F22 + Frf(\text{leg orthosis})$$

As additional information, in the state where the foot of the leg wearing the foot attachment portion 3 is landing in such a way that almost the entire surface of the bottom face of the foot base 13 of the foot attachment portion 3 is in contact with the ground, F22(orthosis→person) is substantially zero and the force F22 detected from the output of the force sensor 22 is substantially equal to the force opposite in sign to the floor reaction force acting on the leg link portion 4 corresponding to the leg.

Moreover, the actual joint support moment Ma(knee) acting on the knee joint of the person A from the support orthosis 1 when torques are generated on the electric motors 15 and 16 of the each leg link portion 4 of the support orthosis 1 is generated by a force (translational force) acting on the person A from the leg link portion 4 of the support orthosis 1 at the coupled place to the support orthosis 1 in the portion from the knee to the foot (the knee and lower portion) of the leg of the person A. In this condition, the coupled place is the foot in this embodiment, and therefore the actual joint support moment Ma(knee) is generated due to the applied force F22 (orthosis→person). Moreover, the actual joint support moment Ma(hip) generated at the hip joint of the person A is generated by a force (translational force) acting on the person A from the support orthosis 1 at the coupled place to the support orthosis 1 in the portion from the hip joint to the foot (the hip joint and lower portion) of the leg of the person A. In this condition, the coupled place is the foot and the thigh in this embodiment, and therefore the actual joint support moment Ma(hip) is generated due to the applied force F22 (orthosis→person) and F20(orthosis→person).

Thus, the actual joint support moment estimation unit 44 finds the estimated values of the actual joint support moments Ma(knee) and Ma(hip) on the basis of the applied forces F20 and F22 detected from the outputs of the force sensors 20 and 22 and the floor reaction force Frf(leg orthosis) obtained by the floor reaction force estimation unit 65 of the orthosis-side joint moment estimation unit 42 by using the following formulas (152a) and (152b):

$$Ma(\text{knee}) = L8 \times F22(\text{orthosis} \to \text{person})x \quad (152a)$$

$$Ma(\text{hip}) = (L8 + L7 \times \cos\theta\_\text{knee}) \times F22(\text{orthosis} \to \text{person})x + \quad (152b)$$
$$L7 \times \sin\theta\_\text{knee} \times F22(\text{orthosis} \to \text{person})z +$$
$$L20 \times F20(\text{orthosis} \to \text{person})x$$

In the above, as shown in FIG. 23, L7 is the length of the thigh of the person A and L8 is the length of the crus of the person A. In addition, L20 is the distance from the hip joint of the person A to the place of the force sensor 20 (the distance on the XZ plane of the leg coordinate system LC) and is calculated based on the output of the displacement sensor 21. In other words, the moving position of the force sensor 20 relative to the thigh link member 8 is found from the output of the displacement sensor 21, and therefore the distance L20 from the hip joint of the person A to the place of the force sensor 20 can be calculated based on the moving position. Unless the central axis direction of the thigh is coincident with the central axis direction of the thigh link member 8, L20 can be calculated by using the output of the displacement sensor 21, the tilt angle θ_thigh of the thigh, and the tilt angle θ_thigh orthosis of the thigh link member 8. Additionally, θ_knee is previously calculated by the two-dimensional leg posture and element center-of-gravity location calculation unit 52 of the human-side joint moment estimation unit 41. F20(orthosis→person)x is a value detected from the output of the force sensor 20. F22(orthosis→person)x and F22 (orthosis→person)z are a component in the central axis direction and a component in the perpendicular direction to the central axis direction of the crus of the person A on the XZ plane of the leg plane LC, respectively, in the applied force F22(orthosis→person). These F22(orthosis→person)x and F22(orthosis→person)z are calculated by the following formulas (151a) and (151b) expressed by a component representation of the formula (151):

$$F22(\text{orthosis} \to \text{person})x = F22x + Frf(\text{leg orthosis})x \quad (151a)$$

$$F22(\text{orthosis} \to \text{person})z = F22z + Frf(\text{leg orthosis})z \quad (151b)$$

In this case, F22x and F22z are values detected from the outputs of the force sensor 22 as described above. In addition, Frf(leg orthosis)x and Frf(leg orthosis)z are a component in the central axis direction and a component in the perpendicular direction to the central axis direction of the crus of the person A on the XZ plane of the leg plane LC, respectively, in the floor reaction force Frf(leg orthosis). These Frf(leg orthosis)x and Frf(leg orthosis)z are calculated by coordinate transforming Frf(leg orthosis/LC) obtained by the leg plane projection unit 66 of the orthosis-side joint moment estimation unit 42 by using the tilt angle θ_crus previously calculated by the two-dimensional leg posture and element center-of-gravity location calculation unit 61.

The above is the arithmetic processing of the actual joint support moment estimation unit 44.

Figure 24:
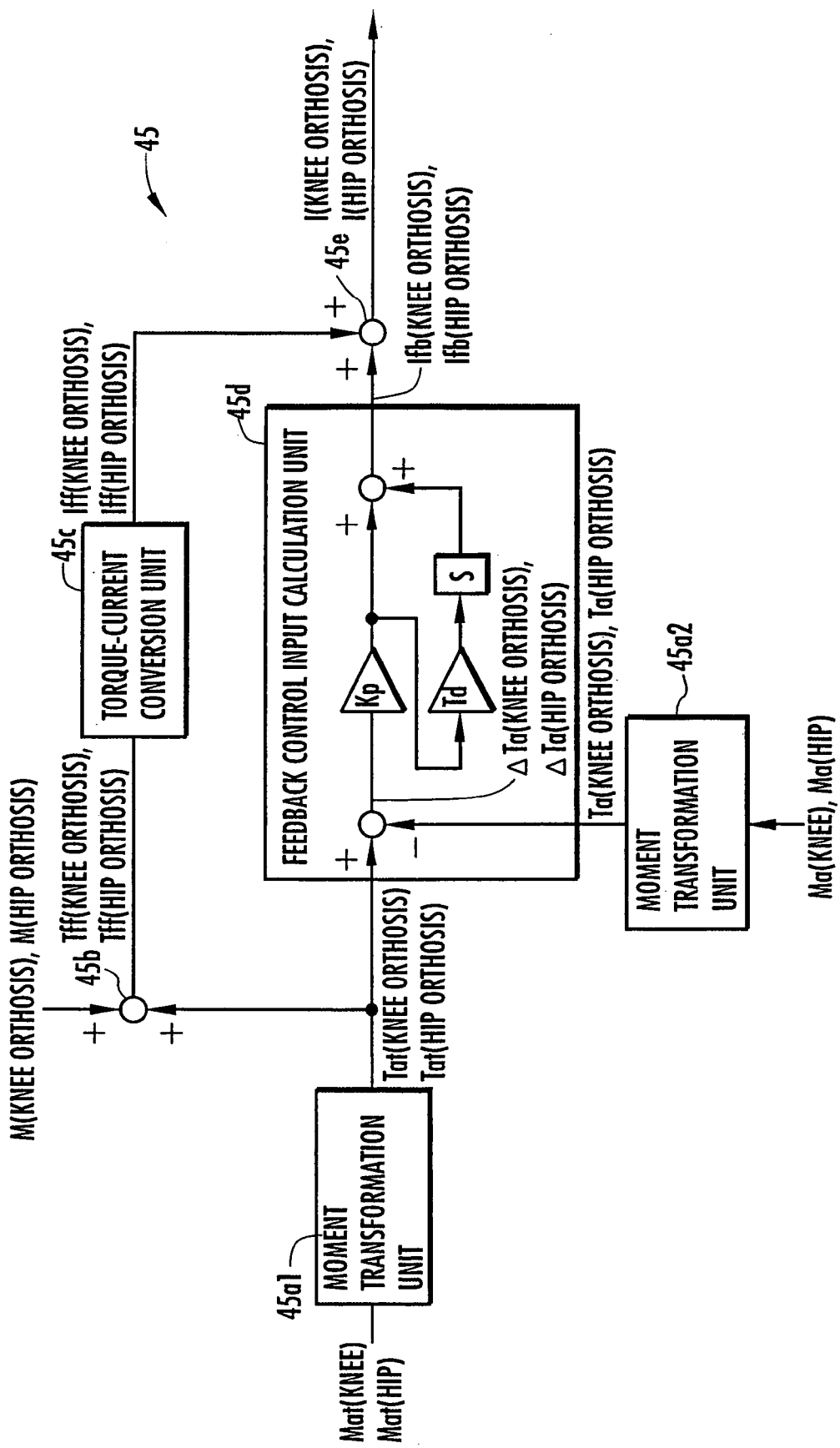
FIG. 24 is a block diagram showing an arithmetic processing function of a motor control unit shown in FIG. 6.

The arithmetic processing unit 25 performs the arithmetic processing of the motor control unit 45, next. The arithmetic processing of the motor control unit 45 will be described hereinafter with reference to FIG. 24. FIG. 24 is a block diagram showing functional units of the motor control unit 45.

The motor control unit 45 includes moment transformation units 45a1 and 45a2, a feedforward torque determination unit 45b, a torque-current conversion unit 45c, a feedback control input calculation unit 45d, and an indicator current determination unit 45e and controls the generated torques of the electric motors 15 and 16 by using these units as described below.

First, the motor control unit 45 transforms (converts) the target joint support moments Mat(knee) and Mat(hip) determined by the target joint support moment determination unit 43 into the target motor support torques Tat(hip orthosis) and Tat(knee orthosis), which are target values of the support torques of the electric motors 15 and 16 by means of the moment transformation unit 45a1. The target motor support torques Tat(hip orthosis) and Tat(knee orthosis) are such torques that the moments generated at the knee joint and the hip joint of the person A are Mat(knee) and Mat(hip), respectively, when the torques are generated at the electric motors 15 and 16 (generated at the hip joint region 7 and the knee joint region 9 of the leg link portion 4), respectively. In this case, for example, the lengths or tilt angles of the thigh and the crus of the each leg of the person A are used to find the translational force applied from the ankle joint of the person A to the each leg link portion 4 of the support orthosis 1 due to the target joint support moments Mat(knee) and Mat(hip) when these moments are generated at the knee joint and the hip joint of the person A, respectively. Then, with the translational force, the moments generated at the knee joint region 9 and the hip joint region 7 of the each leg link portion 4 of the support orthosis 1 may be calculated as the target motor support torques Mat(hip orthosis) and Mat(knee orthosis) by using the lengths and tilt angles of the crus link member 10 and the thigh link member 8 of the each link portion 4.

Moreover, the motor control unit 45 converts the estimated values of the actual joint support moments Ma(knee) and Ma(hip) estimated by the actual joint support moment estimation unit 44 to the actual motor support torques Ta(hip orthosis) and Ta(knee orthosis), which are actual values of the support torques of the electric motors 15 and 16, respectively, by using the moment transformation unit 45a2. The actual motor support torques Ta(hip orthosis) and Ta(knee orthosis) are such torques that the moments generated at the knee joint and the hip joint of the person A are Ma(knee) and Ma(hip) when the torques are generated at the electric motors 15 and 16 (when they are generated at the hip joint region 7 and the knee joint region 9 of the each leg link portion 4), respectively. These Ta(hip orthosis) and Ta(knee orthosis) are calculated by the same processing as the moment transformation unit 45a2.

Subsequently, the motor control unit 45 determines feedforward target values Tff(hip orthosis) and Tff(knee orthosis) of the torques generated at the electric motors 15 and 16, respectively, by the feedforward torque determination unit 45b from the target motor support torques Tat(hip orthosis) and Tat(knee orthosis) and joint moment M(P_crus orthosis) (hereinafter, referred to as knee joint moment M(knee orthosis)) and M(P_thigh orthosis) (hereinafter, referred to as hip joint moment M(hip orthosis)) estimated by the orthosis-side joint moment estimation unit 42. In this case, the feedforward target value Tff(hip orthosis) and Tff(knee orthosis) are determined by adding the hip joint moment M(hip orthosis) and the knee joint moment M(knee orthosis) to the target motor support torque Tat(hip orthosis) and Tat(knee orthosis), respectively.

Moreover, the motor control unit 45 obtains feedforward indicator current Iff(hip orthosis) and Iff(knee orthosis), which are feedforward values of the indicator current of the electric motors 15 and 16, by converting the feedforward target values Tff(hip orthosis) and Tff(knee orthosis) to the indicator current (indicator values of the flowing current) of the electric motors 15 and 16 using a preset data table or the like by means of the torque-current conversion unit 45c.

Moreover, the motor control unit 45 performs the processing of the feedback control input calculation unit 45d in parallel with the processing of the feedforward torque determination unit 45b and the torque-current conversion unit 45c. The feedback control input calculation unit 45d calculates feedback indicator current Ifb(hip orthosis) and Ifb(knee orthosis), which are feedback control inputs of the indicator current of the electric motors 15 and 16, according to the feedback control law in such a way as to converge the actual motor support torques Ta(hip orthosis) and Ta(knee orthosis) obtained by the moment transformation unit 45a2 to the target motor support torques Tat(knee orthosis) and Tat(hip orthosis) obtained by the moment transformation unit 45a1, respectively. In this instance, for example, the PD control law is used as shown, as the feedback control law. In other words, the feedback control input calculation unit 45d calculates the feedback indicator current Ifb(hip orthosis) and Ifb(knee orthosis) by the following formulas (155a) and (155b):

$$Ifb(\text{hip orthosis}) = \\ Kp \times \Delta Ta(\text{hip orthosis}) + Kp \times Td \times d\,\Delta Ta(\text{hip orthosis})/dt \quad (155a)$$

$$Ifb(\text{knee orthosis}) = \\ Kp \times \Delta Ta(\text{knee orthosis}) + Kp \times Td \times d\,\Delta Ta(\text{knee orthosis})/dt \quad (155b)$$

Subject to:

$$\Delta Ta(\text{hip orthosis}) = Tat(\text{hip orthosis}) - Ta(\text{hip orthosis})$$

$$\Delta Ta(\text{knee orthosis}) = Tat(\text{knee orthosis}) - Ta(\text{knee orthosis})$$

In the above, Kp and Td are predetermined gain values.

Subsequently, the motor control unit 45 determines the final indicator current I(hip orthosis) and I(knee orthosis) of the electric motors 15 and 16 by adding the feedforward indicator current Iff(hip orthosis) and Iff(knee orthosis) obtained as described above to the feedback indicator current Ifb(hip orthosis) and Ifb(knee orthosis), respectively, by means of the indicator current determination unit 45e. Then, the motor control unit 45 controls the flowing current of the electric motors 15 and 16 to the indicator current I(hip orthosis) and I(knee orthosis) via the motor drive circuit 29 and thereby feedback-controls the generated torques of the electric motors 15 and 16 so that the actual motor support torques Ta(hip orthosis) and Ta(knee orthosis) are coincident with the target motor support torques Tat(knee orthosis) and Tat(hip orthosis), respectively, and so that the actual joint support moments Ma(hip) and Ma(knee) are coincident with the target joint support moments Mat(knee) and Mat(hip), respectively.

The above is the details of the operation of the support orthosis 1 in this embodiment.

As described above, by controlling the electric motors 15 and 16 of the support orthosis 1, the generated torques of the electric motors 15 and 16 are controlled in such a way that the actual joint support moments Ma(knee) and Ma(hip), which are actually generated at the knee joint and the hip joint of the each leg of the person A from the support orthosis 1 by the torques, are coincident with the target joint support moments Mat(knee) and Mat(hip), respectively. In this instance, the target joint support moments Mat(knee) and Mat(hip) are determined according to the joint moments of the each leg of the person A estimated by the calculation of the inverse dynamics model based on the estimated value of the floor reaction force Frf(leg) acting on the person A supposing that the motion of the person A wearing the support orthosis 1 is being made with the support orthosis 1 removed. Moreover, the actual joint support moments Ma(hip) and Ma(knee) are estimated by using the floor reaction force Frf(leg orthosis) acting on the support orthosis 1, supposing that the support orthosis 1 is making the motion of the support orthosis 1 following the motion of the person A independently (by itself), and the force detected values achieved by the force sensors 20 and 22. Therefore, the person A can make the leg motion intended by him or her substantially without being aware of the empty weight of the support orthosis 1.

Figure 25:
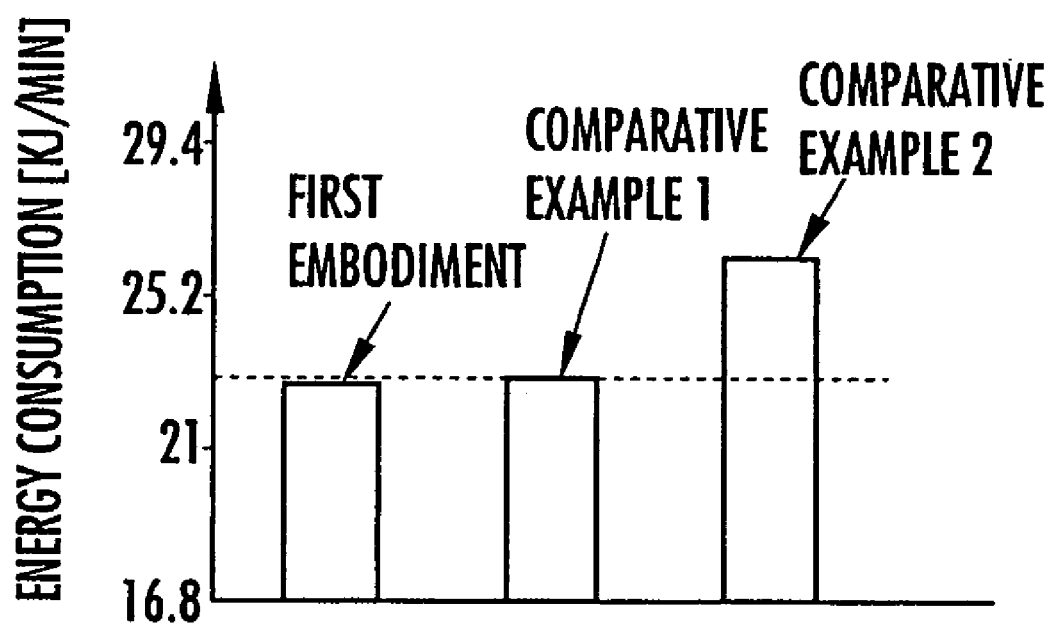
FIG. 25 is a graph for explaining an effect of the embodiment.

Subsequently, a verified example of the effect of this embodiment will be described with reference to FIG. 25 and FIGS. 26(a) and 26(b). The graph of the first embodiment in FIG. 25 shows a measurement of energy consumption per minute of the person A in the case where the person A wearing the support orthosis 1 repeated a series of motions of squatting down and standing up (the so-called "squat" move) with the both legs kept landing. In this case, the series of motions of squatting down and standing up are made at the pace of 22.5 times per minute. In the first embodiment, the target joint support moments Mat(knee) and Mat(hip) are both zero. Incidentally, the energy consumption has been measured by an expiration measuring device.

In addition, the graph of the comparative example 1 in FIG. 25 shows a measurement of energy consumption of the person A in the case where the person A has repeated the squat similarly to the first embodiment without wearing the support orthosis 1. The graph of the comparative example 2 in FIG. 25 shows a measurement of energy consumption of the person A in the case where the person A has repeated the squat similarly to the first embodiment without flowing the current into the electric motors 15 and 16 of the support orthosis 1 put on the person A.

As shown in FIG. 25, the first embodiment is substantially equal to the comparative example 1 in energy consumption and the first embodiment 1 is lower than the comparative example 2 in energy consumption. Therefore, it is understood that the person A can make the motion almost without being aware of the weight of the support orthosis 1 by controlling the electric motors 15 and 16 as described above.

Figure 26A:
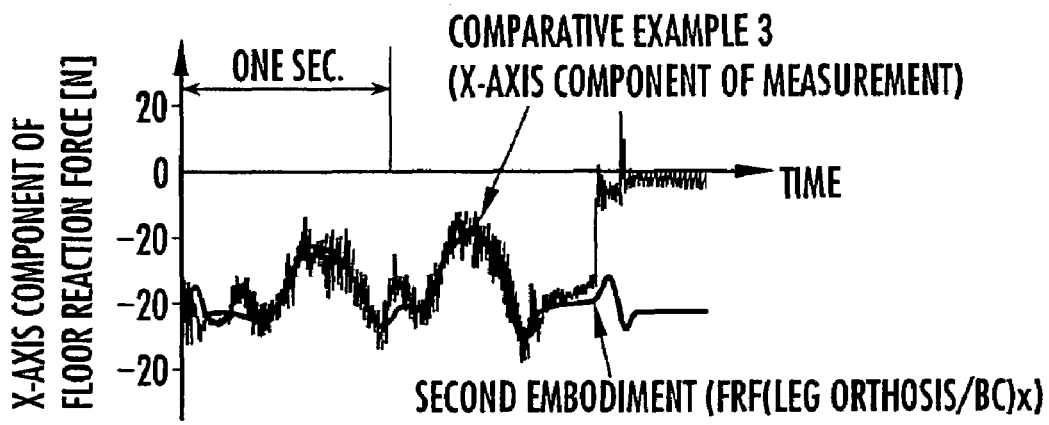
FIGS. 26($a$) to 26($b$) are graphs each showing an example of a floor reaction force estimated by the floor reaction force estimation unit shown in FIG. 8 and a transition of an X-axis component or a Z-axis component of an actual measurement of the floor reaction force.
Figure 26B:
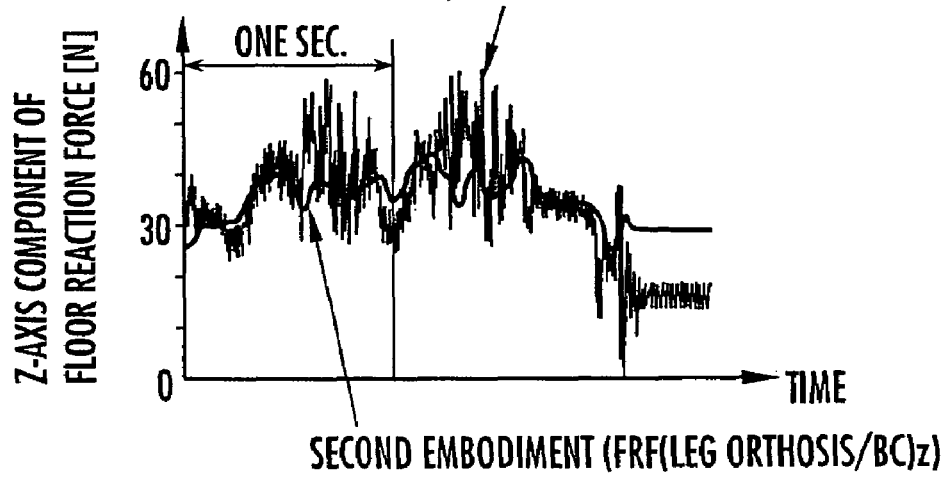

The graphs of the second embodiment in FIGS. 26(a) and 26(b) show variation with time of the X-axis component F(leg orthosis/BC)x and the Z-axis component F(leg orthosis/BC)z of the floor reaction force of one leg link portion 4 calculated by the floor reaction force estimation unit 65 of the orthosis-side joint moment estimation unit 42 in the case where the person A wearing the support orthosis 1 has made a motion of squatting down, standing up, and then squatting down again with the both legs landing. The graphs of the comparative example 3 in FIGS. 26(a) and 26(b) show measurements of the X-axis component and the Z-axis component on the body coordinate system BC of the force opposite in sign to the force F22 detected from the output of the force sensor 22 during the motion of the second embodiment. As described above, in the state where the foot of the leg wearing the foot attachment portion 3 is landing with the almost entire surface of the bottom face of the foot base 13 of the foot attachment portion 3 in contact with the ground, the force F22 detected from the output of the force sensor 22 is almost equal to the force opposite in sign to the floor reaction force acting on the leg link portion4 corresponding to the leg. Therefore, the force opposite in sign to the force F22 detected from the output of the force sensor 22 during the motion of the second embodiment is equivalent to the measurement of the floor reaction force of the each leg link portion 4 of the support orthosis 1 supposing that the support orthosis 1 is making the motion independently.

As shown in FIGS. 26(a) and 26(b), the variation with time of F(leg orthosis/BC)x and F(leg orthosis/BC)z of the second embodiment are very coincident with the variation with time of the X-axis component and the Z-axis component of the measurements of the comparative example 3. Therefore, it is understood that the floor reaction force Frf(leg orthosis/BC) calculated by the floor reaction force estimation unit 65 is preferable as an equivalent to the floor reaction force of the each leg link portion 4 of the support orthosis 1 supposing that the support orthosis 1 is making the motion independently.

Subsequently, some modifications of the embodiments will be described below.

Figure 27:
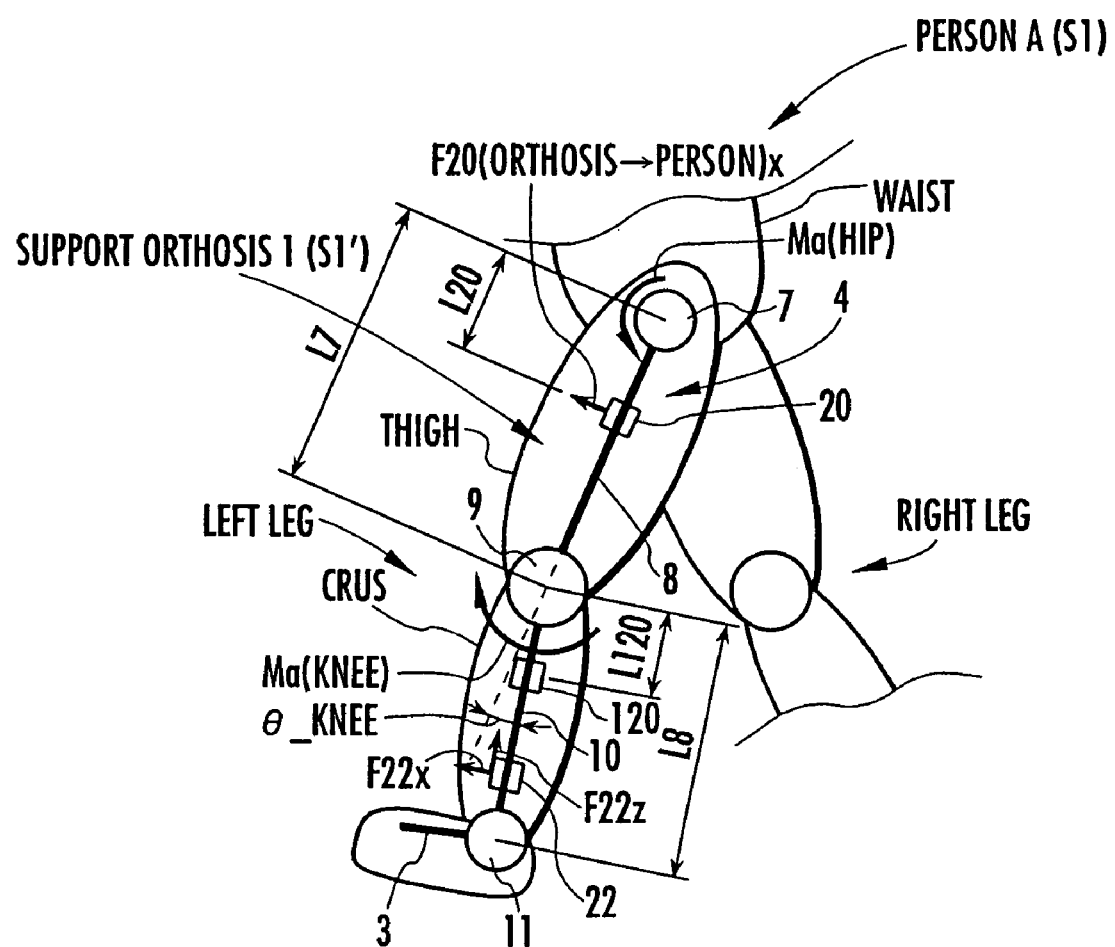
FIG. 27 is a diagram for explaining a method of estimating an actual joint support moment according to a modification of the embodiment of the present invention.

In the embodiments, the support orthosis 1 has been fixed to the person A at the waist and the foot of the person A and the each leg link portion 4 has been coupled to the thigh of the person A. It is also possible, however, to couple the thigh link member 8 of the each leg link portion 4 with the thigh of the person A similarly to the embodiments and to couple the crus link member 10 of the leg link portion 4 to the upper portion or the intermediate portion of the crus of the person A similarly to the thigh, for example. In this case, in order to estimate the actual joint support moments appropriately, there is a need to provide the force sensor 120 also at the coupled place to the crus of the person A in the leg link portion 4, as shown in FIG. 27. FIG. 27 typically shows the lower part of the body of the person A and the lower essential part of the body of the support orthosis 1.

Moreover, in this case, the estimated values of the actual joint support moments Ma(knee) and Ma(hip) can be obtained by the formulas (152c) and (152d) below, for example, instead of the aforementioned formulas (152a) and (152b). In this example, it is assumed that the crus link member 10 of the support orthosis 1 is coupled to the crus of the person A by using a belt member or the like, not shown, via the force sensor 120, that the force sensor 120 is attached to the crus link member 10 so as to be free to move in the central axis direction of the crus link member 10 similarly to the force sensor 20, and that the moving position of the force sensor 120 to the crus link member 10 (the moving position in the central axis direction of the crus link member 10) is detected by the displacement sensor, which is not shown.

$$Ma(\text{knee}) = \qquad (152c)$$
$$L8 \times F22(\text{orthosis} \rightarrow \text{person})x + L120 \times F120(\text{orthosis} \rightarrow \text{person})x$$

$$Ma(\text{hip}) = (L8 + L7 \times \cos\theta\_\text{knee}) \times F22(\text{orthosis} \rightarrow \text{person})x + \qquad (152d)$$
$$L7 \times \sin\theta\_\text{knee}) \times F22(\text{orthosis} \rightarrow \text{person})z +$$
$$L20 \times F20(\text{orthosis} \rightarrow \text{person})x + (L120 + L7 \times \cos\theta\_\text{knee}) \times$$
$$F120(\text{orthosis} \rightarrow \text{person})x$$

In the above, L120 is a distance (a distance on the XZ plane (on the leg plane PL) of the leg coordinate system LC) from the knee joint of the person A to the force sensor 120 as shown in FIG. 27 and is calculated based on the output of the displacement sensor for detecting the moving position of the force sensor 120 to the crus link member 10. Furthermore, F120(orthosis→person)x is a component in the perpendicular direction (in the perpendicular direction on the XZ plane (on the leg plane PL) of the leg coordinate system LC) to the central axis of the crus of the person A in the applied force (translational force) applied from the support orthosis 1 to the each leg of the person A at the place of the force sensor 120 (at the coupled place between the crus link member 10 and the crus of the person A). The component is detected from the output of the force sensor 120 in the same manner as for the force sensor 20. Variables other than the above necessary for the calculations of the formulas (152c) and (152d) are the same as those for use in the calculations of the aforementioned formulas (152a) and (152b).

The arithmetic operations of the calculations of the actual joint support moments may be the same as those of the above embodiments.

As additional information, in the above embodiments, it is assumed that the force sensor 120 is free to move in the central axis direction of the crus link member 10 and that no applied force (translational force) is generated from the support orthosis 1 to the person A in the central axis direction of the crus of the person A at the place of the force sensor 120 or it is almost zero. Unless the central axis direction of the crus link member 10 is coincident with the central axis direction of the crus of the person A, however, an applied force F120 (person→orthosis)z is generated from the support orthosis 1 to the person A in the central axis direction of the crus of the person A at the place of the force sensor 120 in the strict sense. In addition, if the force sensor 120 is fixed to the crus link member 10, the applied force F120(person→orthosis)z is generated in general. Then, the applied force F120 (person→orthosis)z is to generate a moment at the hip joint of the person A. Therefore, when finding the actual joint support moment Ma(hip), consideration may be give to the F120 (person→orthosis)z. If so, L7×sin θ\_knee×F120 (person→orthosis)z may be added to the right-hand side of the formula (152d), further. Incidentally, F120 (person→orthosis)z can be detected from the output of the force sensor 120.

While the thigh link member 8 of the support orthosis 1 has been coupled to the thigh of the person A in the embodiments, they need not be coupled necessarily. If they are not coupled to each other, it is simply necessary to calculate Ma(hip) by a formula without the third term (the term including F20 (orthosis→person)x) in the right-hand side of the formula (152b) when calculating the estimated value of the Ma(hip) out of the actual joint support moments Ma(knee) and Ma(hip). Others may be the same as those of the embodiment.

If only the crus link member 10 of the support orthosis 1 is coupled to the crus of the person A, it is simply necessary to calculate Ma(knee) by the formula (152c) and to calculate Ma(hip) by the formula without the term including F20 (orthosis→person)x in the formula (152d) (or the formula in which consideration is given to the aforementioned F120 (person→orthosis)z).

Moreover, while no unit for giving a torque is provided in the ankle joint region 11 of the support orthosis 1 in the embodiments, it is also possible to provide a torque generation unit for applying a torque such as, for example, an electric motor in the ankle joint region 11. In this case, the force sensor 22 for detecting the applied force F22 is provided in the foot link member 12 of the leg link portion 4, for example. Then, the actual joint support moments Ma(ankle), Ma(knee), and Ma(hip) actually applied to the ankle joint, the knee joint, and the hip joint of the person A, respectively, by the operation of the each electric motor of the support orthosis are estimated based on the outputs of the force sensors 22 and 20 or the like by the same mechanical calculation method as the embodiments. Moreover, similarly to the embodiments, the target joint support moments Mat(ankle), Mat(knee), and mat(hip) of the ankle joint, the knee joint, and the hip joint of the person A are determined according to the joint moments M(P\_foot), M(P\_crus), and M(P\_thigh) of these joints estimated by the human-side joint moment estimation unit 41. They may be determined in the same manner as for determining Mat(knee) and Mat(hip) by using the target joint support moment determination unit 43 in the embodiments. Then, the each electric motor may be controlled in the same manner as for the embodiments in such a way that the actual joint support moments Ma(ankle), Ma(knee), and Ma(hip) are coincident with the determined target joint support moments Mat (ankle), Mat(knee), and Mat(hip), respectively. In this case, among the joint moments M(P\_foot orthosis) (=M(ankle orthosis)), M(P\_crus orthosis) (=M(knee orthosis)), and M(P\_thigh orthosis) (=M(hip orthosis)) for use in determining the feedforward target values Tff(hip), Tff(knee), and Tff(ankle) for generating torques at the electric motors, M(P\_foot orthosis) may be found by the following formula (115d'), instead of the formula (115d):

$$M(\text{P\_foot orthosis}) = \qquad (115d')$$
$$\text{I\_foot orthosis} \times (\omega(\text{foot orthosis})' + \omega(BCO/LC)y') -$$
$$\{(U(\text{orthosis } COP/LC) - U(\text{G\_foot orthosis}/LC)) \times$$
$$Frf(\text{leg orthosis}/LC)\}y -$$
$$\{(U(\text{P\_foot orthosis}/LC) - U(\text{G\_foot orthosis}/LC)) \times$$
$$F(\text{P\_foot orthosis}/LC)\}y$$

In the above, I\_foot orthosis is a moment of inertia around the center of gravity of the foot element S9 of the orthosis rigid link model S1' and is stored in the memory of the arithmetic processing unit 25. Moreover, ω(foot orthosis)' is calculated from the time series data of the tilt angle θ\_foot orthosis as a second derivative of the tilt angle θ\_foot orthosis calculated by the two-dimensional leg posture and element center-of-gravity location calculation unit 61 (or the tilt angle θ\_foot calculated by the two-dimensional leg posture and element center-of-gravity location calculation unit 52). Furthermore, U(P\_foot/LC) (=U(D\_crus/LC) is U(J\_ankle orthosis/LC) calculated by the two-dimensional leg posture and element center-of-gravity location calculation unit 61.

Still further, U(G_foot orthosis/LC) is a position vector (more accurately, a pair of the X-axis component and the Z-axis component of the position vector) of the G_foot orthosis on the leg coordinate system LC calculated by the two-dimensional leg posture and element center-of-gravity location calculation unit 61. Variables other than these in the formula (115d') are as described in the embodiments.

In addition, while the floor reaction force Frf(leg) of the person A and the floor reaction force Frf(leg orthosis) of the support orthosis 1 have been calculated in consideration of the total rate of change of angular momentum in the embodiments, it is also possible to calculate them by using the method in Japanese Patent Laid-Open No. 2003-89083 or No. 2003-112893 suggested by the applicant, for example. Moreover, the floor reaction force application point COP may also be estimated by using the method suggested in Japanese Patent Laid-Open No. 2003-89083 or No. 2003-112893.

What is claimed is:

1. A support moment control method for a leg motion support orthosis, which controls torques generated by a torque generation unit for the leg motion support orthosis having at least a waist attachment portion fixed to the waist of a person, a pair of foot attachment portions fixed to the feet of the person and provided in such a way as to be put in contact with the ground with bearing the weight of the person during a landing period of the feet, and a pair of leg link portions extending substantially along the legs of the person between the waist attachment portion and the foot attachment portions by coupling the waist attachment portion and each of the foot attachment portions, wherein each of the leg link portions has a plurality of joint regions including at least three joint regions corresponding to the person's hip joint, knee joint, and ankle joint, respectively, and the torque generation unit capable of generating torques at the joint regions corresponding to at least the hip joint and the knee joint of the plurality of joint regions, the method comprising:

during the motion of both legs of the person wearing the leg motion support orthosis, a first step of sequentially estimating human-side joint moments, which are moments to be generated at the knee joint and the hip joint of the each leg, respectively, supposing that the person is making the motion of the both legs with the leg motion support orthosis removed from the person;

a second step of sequentially estimating floor reaction forces acting on the foot attachment portions of the leg motion support orthosis, supporting that the leg motion support orthosis is independently making a motion of the leg motion support orthosis following the motion of the person's legs;

a third step of sequentially measuring reaction forces each of a resultant force between a force applied from the person via the foot attachment portion coupled to the leg link portion of each leg link portion of the leg motion support orthosis and the floor reaction force applied to the foot attachment portion, supposing that the leg motion support orthosis is independently making the motion of the leg motion support orthosis following the motion of the person's legs, on the basis of an output of a force sensor provided in the leg link portion in the area closer to the foot attachment portion than to the knee joint region of the each leg link portion so that the resultant force can be detected;

a fourth step of measuring at least the amount of rotation of the knee joint of the joints of the person's each leg;

a fifth step of sequentially calculating estimated values of actual joint support moments, which are support moments actually generated at the knee joint and the hip joint of the person's each leg due to the torques generated by the torque generation unit by using at least the amount of rotation of the knee joint measured in the fourth step, the reaction forces of the resultant forces measured in the third step, and the floor reaction forces estimated in the second step;

a sixth step of sequentially determining target joint support moments, each of which is a target support moment to be generated at each of the knee joint and the hip joint of the person's each leg by means of the torque generated by the torque generation unit according to at least the human-side joint moments of the knee joint and the hip joint of the each leg estimated in the first step; and a seventh step of controlling the torques generated by the torque generation unit in such a way that the estimated values of the actual joint support moments of the knee joint and the hip joint of the person's each leg calculated in the fifth step are substantially coincident with the respective target joint support moments of the knee joint and the hip joint determined in the sixth step.

2. The support moment control method for the leg motion support orthosis according to claim 1, wherein the first step includes the steps of: estimating a floor reaction force applied to the each leg, supposing that the motion of the person's legs is being made with the leg motion support orthosis removed from the person, by using at least an output of an acceleration sensor provided in the leg motion support orthosis, an output of a joint displacement sensor provided in the each joint region in such a way as to be capable of detecting the amount of rotation of the each joint region of the each leg link portion of the leg motion support orthosis, and a rigid link model in which the person is represented by a link body made of a plurality of rigid elements and a plurality of joint elements; and estimating the human-side joint moments in arithmetic processing of an inverse dynamics model by using the estimated floor reaction force.

3. The support moment control method for the leg motion support orthosis according to claim 1, wherein the second step includes estimating a floor reaction force applied to the each foot attachment portion of the leg motion support orthosis, supposing that the leg motion support orthosis is independently making the motion of the leg motion support orthosis following the motion of the person's legs, by using at least an output of an acceleration sensor provided in the leg motion support orthosis, an output of a joint displacement sensor provided in the joint region in such a way as to be capable of detecting the amount of rotation of the each joint region of the each leg link portion of the leg motion support orthosis, and a rigid link model in which the leg motion support orthosis is represented by a link body made of a plurality of rigid elements and a plurality of joint elements.

4. The support moment control method for the leg motion support orthosis according to claim 1, wherein:

the each leg link portion of the leg motion support orthosis is coupled to the person's leg corresponding to the leg link portion in at least one or more places;

the method includes an eighth step of measuring the reaction forces of the forces applied from the person to the leg motion support orthosis in the coupled places on the basis of the output of the force sensor provided in the leg motion support orthosis in such a way as to be capable of detecting the force; and the fifth step includes calculating estimated values of the actual joint support moments by using at least the reaction forces of the forces measured in the eighth step, the amount of rotation of the knee joint measured in the fourth step, the reaction forces of the resultant forces measured in the third step, and the floor reaction forces estimated in the second step.

5. The support moment control method for the leg motion support orthosis according to claim 1, further comprising a ninth step of sequentially estimating orthosis-side joint moments, which are moments to be generated in the knee joint region and the hip joint region of the each leg link portion of the leg motion support orthosis, supposing that the leg motion support orthosis is independently making the motion of the leg motion support orthosis following the motion of the person's legs, by performing arithmetic processing of the inverse dynamics model using the floor reaction forces estimated in the second step, wherein the seventh step includes the steps of: determining a feedback control input of the torques generated by the torque generation unit according to a feedback control law in such a way as to approximate the difference between the estimated value of each of the actual joint support moments of the knee joint and the hip joint of the person's each leg calculated in the fifth step and each of the target joint support moments of the knee joint and the hip joint determined in the sixth step to zero; and determining a feedforward control input of the torques generated by the torque generation unit at least according to each of the orthosis-side joint moments of the knee joint region and the hip joint region of the each leg link portion of the leg motion support orthosis estimated in the ninth step, to control the torques generated by the torque generation unit according to the determined feedback control input and the feedforward control input.

* * * * *